(12) United States Patent
Ernst et al.

(10) Patent No.: US 8,921,328 B2
(45) Date of Patent: Dec. 30, 2014

(54) E-SELECTIN ANTAGONISTS

(75) Inventors: Beat Ernst, Magden (CH); Céline E. Weckerle, Basel (CH); Jonas K. Egger, Basel (CH)

(73) Assignee: GlycoMimetics, Inc., Gaithersburg, MD (US)

( * ) Notice: Subject to any disclaimer, the term of this patent is extended or adjusted under 35 U.S.C. 154(b) by 0 days.

(21) Appl. No.: 13/822,573

(22) PCT Filed: Sep. 12, 2011

(86) PCT No.: PCT/US2011/051234
§ 371 (c)(1),
(2), (4) Date: May 24, 2013

(87) PCT Pub. No.: WO2012/037034
PCT Pub. Date: Mar. 22, 2012

(65) Prior Publication Data
US 2013/0331350 A1 Dec. 12, 2013

Related U.S. Application Data

(60) Provisional application No. 61/382,716, filed on Sep. 14, 2010.

(51) Int. Cl.
*A61K 31/70* (2006.01)
*C07H 17/02* (2006.01)
*C07H 15/26* (2006.01)

(52) U.S. Cl.
CPC ............... *C07H 17/02* (2013.01); *C07H 15/26* (2013.01)
USPC ............................................ 514/35; 536/17.4

(58) Field of Classification Search
None
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methdos 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Arakaki. R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Arshad, S. et al., "Primary prevention of asthma and allergy," J. Allergy Clin. Immunol., 116: 3-14 (2005).

(Continued)

*Primary Examiner* — Traviss C McIntosh, III
(74) *Attorney, Agent, or Firm* — Finnegan, Henderson, Farabow, Garrett & Dunner, LLP

(57) ABSTRACT

Compounds, compositions and methods are provided for inhibiting in vitro and in vivo processes mediated by E-selectin binding. More specifically, particular glycomimetic compounds are described, wherein the compounds are E-selectin antagonists.

9 Claims, 7 Drawing Sheets

(56) References Cited

U.S. PATENT DOCUMENTS

| | | | |
|---|---|---|---|
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Kogan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A * | 11/1999 | Nagy et al. ............. 514/54 |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 12/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,175 B2 | 1/2005 | Bistrup et al. |
| 6,872,714 B1 | 3/2005 | Schols |
| 6,875,738 B1 | 4/2005 | Clark-Lewis et al. |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 2001/0046970 A1 | 11/2001 | Nagy et al. |
| 2002/0031508 A1 | 3/2002 | Wagner et al. |
| 2002/0040008 A1 | 4/2002 | Wagner et al. |
| 2002/0128225 A1 | 9/2002 | Liu et al. |
| 2002/0132220 A1 | 9/2002 | Berens et al. |
| 2002/0164336 A1 | 11/2002 | Harrison et al. |
| 2002/0164748 A1 | 11/2002 | Bistrup et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0039683 A1 | 2/2003 | Cantrell et al. |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0187171 A1 | 8/2005 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2009/0253646 A1 | 10/2009 | Magnani |
| 2009/0312278 A1 | 12/2009 | Magnani et al. |
| 2010/0215575 A1 | 8/2010 | O'Neill et al. |
| 2010/0311105 A1 | 12/2010 | Lu et al. |
| 2011/0142856 A1 | 6/2011 | Kokubo et al. |
| 2011/0229409 A1 | 9/2011 | Ranganathan et al. |
| 2012/0258043 A1 | 10/2012 | Ranganathan et al. |
| 2014/0178303 A1 | 6/2014 | Magnani et al. |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| JP | 2009-507031 | 2/2009 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |

(56) References Cited

FOREIGN PATENT DOCUMENTS

| WO | WO 94/29477 | 12/1994 |
|---|---|---|
| WO | WO 95/00527 | 1/1995 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 99/42130 | 8/1999 |
| WO | WO 99/43353 | 9/1999 |
| WO | WO 99/43356 | 9/1999 |
| WO | WO 00/02870 | 1/2000 |
| WO | WO 01/89564 | 11/2001 |
| WO | WO 02/22820 | 3/2002 |
| WO | WO 02/062810 | 8/2002 |
| WO | WO 03/055876 | 7/2003 |
| WO | WO 03/088980 | 10/2003 |
| WO | WO 03/097658 | 11/2003 |
| WO | WO 2004/004636 | 1/2004 |
| WO | WO 2004/033663 | 4/2004 |
| WO | WO 2004/058304 | 7/2004 |
| WO | WO 2005/016349 | 2/2005 |
| WO | WO 2005/051920 | 6/2005 |
| WO | WO 2005/054264 | 6/2005 |
| WO | WO 2005/058934 | 6/2005 |
| WO | WO 2005/085219 | 9/2005 |
| WO | WO 2005/116088 | 12/2005 |
| WO | WO 2006/017180 | 2/2006 |
| WO | WO 2006/022454 | 3/2006 |
| WO | WO 2006/074426 | 7/2006 |
| WO | WO 2006/074428 | 7/2006 |
| WO | WO 2006/127906 | 11/2006 |
| WO | WO 2007/021721 | 2/2007 |
| WO | WO 2007/022089 | 2/2007 |
| WO | WO 2007/022385 | 2/2007 |
| WO | WO 2007/028050 | 3/2007 |
| WO | WO 2007/033329 | 3/2007 |
| WO | WO 2008/008852 | 1/2008 |
| WO | WO 2008/008854 | 1/2008 |
| WO | WO 2008/060378 | 5/2008 |
| WO | WO 2008/100453 | 8/2008 |
| WO | WO 2008/109154 | 9/2008 |
| WO | WO 2009/152245 | 12/2009 |
| WO | WO 2010/126888 | 11/2010 |
| WO | WO 2012/037034 | 3/2012 |
| WO | WO 2012/061662 | 5/2012 |
| WO | WO 2013/096926 | 6/2013 |

OTHER PUBLICATIONS

Arshad, S. et al., "Primary prevention of asthma and atopy during childhood by allergen avoidance in infacny: a randomised controlled study," Thorax., 58:489-493 (2003).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem, 266(32)21537-21547, 1991.
Banteii et al., "Synthesis of sialyl lewisx mimics. Modifications of the 6-position of galactose," Bioorganic & Medicinal Chemistry Letters, 11(4): 459-462 (2001).
Banteli, R. et al. "Potent E-Selectin Antagonists," Helvetica Chimica Acta 83(11): 2893-2907, 2000.
Barnes, P. et al., "How do corticosteroids work in asthma?" Ann. Intern. Med., 139: 359-370 (2003).
Bastin, R.. et al, "Salt Selection and Optimisation Procedures for Pharmaceutical New Chemical Entities" Organic Process Research & Development (2000), vol. 4, pp. 427-435.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Berg et al., "A Carbohydrate Domain Common to Both Sialyl Le.sup.a and Sialyl Le.sup.x is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Bhaskar, V. et al. "E-selectin Up-regulation Allows for Targeted Drug Delivery in Prostrate Cancer," Cancer Research, 63: 6387-6394 (Oct. 2003).
Bird and Kimber, "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke, "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bowen et al., "Characterization of a Human Homologue of the Murine Peripheral Lymph Node Homing Receptor," Journal of Cell Biology, 109:421-427, 1989.
Brandley et al., "Carbohydrate Ligands of LEC Cell Adhesion Molecules," Cell, 63:861-863, 1990.
Bridger, GJ et al. "Synthesis and Structure—Activity Relationships of Phenylenebis(methylene)-Linked Bis-Tetraazamacrocycles That Inhibit HIV Replication. Effects of Macrocyclic Ring Size and Substituents on the Aromatic Linker," J. Med. Chem., 38: 366-378 (1995).
Broquet et al., "Effect of Desipramine on a Glycoprotein Sialytransferase Activity in C6 Cultured Glioma Cells," J. Neurochem., 54:388-394, 1990.
Calarese, D. A. et al., "Antibody Domain Exchange is and Immunolgical Solution to Carbohydrate Cluster Recognition," Science 300:2065-2071, Jun. 2003.
Calarese, D. A. et al., "Dissection fo the Carbohydrate Specificity of the Broadly Netralizing Anti-HIV-1 Antibody 2G12," Proceedings of the National Academy of Sciences 102(38)13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of3-Cyclohexene-I-carboxylic Acid," Acta Chemica Scandivavica, 24(8):2693-2698, 1970.
Chang, J. et al. "GMI-1070, a novel pan-selectin antagonist, reverses acute vascular occlusions in sickle cell mice," Blood, 116(10): 1779-1786 (Sep. 2010).
Chemical Abstracts (STN), Accession No. 1997:584307, Jul. 8, 1997.
Childs et al. , "High-molecular-weight glycoproteins are the major carriers of the carbohydrate differentiation antigens I, I and SSEA-1 of mouse teratocarcinoma cells," Biochem. J., 215:491-503 (1983).
Christianson, S.W. et al., "Enhanced Human CD4+ T Cell Engraftment in β2-Microglobulin-Deficient NOD-scid Mice," The Journal of Immunology, 158:3578-3586 (1997).

(56) References Cited

OTHER PUBLICATIONS

Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine-Arene Interactions," Angew Chem., 117:5240-5242 (2005).
Daoudil, Jean-Michel et al., "New bicyclam-GalCer analogue conjugates: synthesis and in vitro anti-HIV activity," Bioorg. & Med. Chem. Letters 14:495-498, 2004.
Datta and Takayama, "Isolation and purification of trehalose 6-mono- and 6,6'-di-corynomycolates from *Cornyebacterium matruchotii*. Structural characterization of .sup 1H NMR," Carbohydrate Research 245:151-158, 1993.
De Clercq, Erik, "The bicyclam AMD3100 story," Nat. Rev. Drug Disc. 2:581-587, Jul. 2003.
Devine: "Rapid Mobilization of CD34+ Cells Following Administration of the CXCR4 Antagonist AMD 3100 to patients With Multiple Myeloma and Non-Hodgkin's Lymphoma," Journal of Clinical Oncology, 22(6): 1095-1102 (Feb. 23, 2004).
Dittmar, Thomas et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz, B.J. et al., "Safe Use of the CSCR4 Inhibitor ALX40-4C in Humans," AIDS Research and Human Retroviruses 17(6):475-486, 2001.
Duijvestijn et al., "High Endothelial Differentiation in Human Lymphoid and Inflammatory Tissues Defined by Monoclonal Antibody HECA-452," Am. J. Path. 130:147-155, 1988.
Dupre, B. et al., "Glycomimetic Selectin Inhibitors: (.alpha.-D-Mannopyranosyloxy)methylbiphenyls," Bioorganic & Medicinal Chemistry Letters 6(5): 569-572, 1996.
Edgington, "How Sweet it is: Selectin-Mediating Drugs," Biotechnology 10: 383-389, 1992.
Edwards, W. Barry et al., "Generally Applicable, Convenient Solid-Phase Synthesis and Receptor Affinities of Octreotide Analogs," J. Med. Chem. 37:3749-3757, 1994.
Egberink, H. et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger, J. et al. "Nanomolar E-Selectin Antagonists with Prolonged Half-Lives by a Fragment-Based Approach," JACS, 135(26): 9820-9828 (Jul. 2013).
Embury, S.H. et al., "The contribution of endothelial cell P-selectin to the microvascular flow of mouse sickle erythrocytes in vivo," Blood 104(10):3378-3385, Nov. 15, 2004.

English Abstract for DE 2434953, Feb. 6, 1975.
English Abstract for JP 9-176047, published Jul. 8, 1997.
English Abstract for WO 96/20204, published Jul. 4, 1996.
English Translation of JP 06-0306092, dated Nov. 1, 1994.
Ernst and Oehrlien, "Substrate and donor specificity of glycosyl transferases," Glycoconjugate Journal 16: 161-170, 1999.
Ernst B. et al., "Design and Synthesis of E-Selectin Antagonists," Chimia 55:268-274, 2001.
Ernst, B. et al., "From carbohydrate leads to glycomimetic drugs," Nature Reviews 8:661-667, Aug. 2009.
European Search Report for EP 11010157 dated Mar. 27, 2012.
Faber et al., "The Many Facets of SDF-1a, CXCR4 Agonist and Antagonists on Hematopoietic Progenitor Cells," J. Biomed. & Biotech. Article ID 26065:1-10, 2007.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embyogenesis," Differentiation 38:124-133, 1988.
Filser, C. et al., "Synthetic glycopeptides from the E-selectin ligand 1 with varied sialyl Lewis (x) structure as cell-adhesion inhibitors of E-selecting," Angewandte Chemie—International Edition, 46(12): 2108-2111 (2007).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocyctes," Nature 304:30-34, 1983.
Garber, N. et al., "On the specificity of the D-galactose-binding lectin (PA-I) of *Pseudomonas aeruginosa* and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-yilum chlorides: potential precursors to meso-ionic 1,2,3,5-dithiadiazolium-4-thiolate," Arkivoc, (vi): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree *Erythrina corallodendron*. Comparison with *Glycine max* (soybean) and *Pseudomonas aeruginosa* lectins," Canadian Journal of Biochemistry, 59(5):315-320 (1981).
Goodman and Gillman's "Pharmacological Basis of Therapeutics," 10th edition, p. 54 (2001).
Gooi et al., "Stage-specific embryonic antigen involves alpha 1-3 fucosylated type 2 blood group chains," Nature 292:156-158, 1981.
Hakomori et al., "Novel Fucolipids Accumulating in Human Adenocarcinoma. I. Glycolipids With Di- or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.

(56) References Cited

OTHER PUBLICATIONS

Hakomori S., "Aberrant Glycosylation in Cancer Cell Membranes as Focused on Glycolipids: Overview and Perspectives," Cancer Res. 45:2405-2414, 1985.
Halloran, M. et al., "Ley/H: An endothelial-selective cytokine-inducible angiogenic mediator," Journal of Immunology, 164(9): 4868-4877 (May 1, 2000).
Handa et al., "Selecting GMP-140 (CD62; PADGEM) Binds to Sialosyl-Le.sup.a and Sialosyl-Le.sup.x, and Sulfated Glycans Modulate this Binding," Biochemical and Biophysical Research Communication 181(3):1223-1230. 1991.
Hansson and Zopf, "Biosynthesis of the Cancer-associated Sialyl-Le.sup.a Antigen," Journal of Biological Chemistry 260(16):9388-9392, 1985.
Harlan, J.M., "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.
Hebbel, P.R., "Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonists of the CXCR-4 Chemokine Receptor, in Human Volunteers," Antimicrobial Agents and Chemotherapy 44(6):1667-1673, Jun. 2000.
Hilal et al., "Electronic structure of orotic acid I. Geometry, conformational preference and tautomerism., Journal of Molecular Structure (Theochem)" 685 (2004) 35-42.
Hilgenbrink, A. et al., "Folate receptor-mediated drug targeting: from therapeutics to diagnostics," J. Pharm. Sci., 94(10): 2135-2146 (2005).
Holgate, ST et al., "Epithelium dysfunction in asthma," Current Reviews of Allergy and Clinical Immunology, 120: 1233-1234 (2007).
Holmes et al., "Enzymatic Basis for the Accumuation of Glycolipids with X and Dimeric X Determinants in Human Lung Cancer Cells (NCI-H69)," J. Biol. Chem. 260(12):7619-7627, 1985.
Hong, P. W.-P. et al., "Identification of the Optimal DC-SIGN Binding Site on Human Immunodeficiency Virus Type 1 gp120," Journal of Virology 18(15):8325-8336, Aug. 2007.
Huse et al., "Generation of a Large Combinatiorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared Via Crossmetathesis of C-Fucopeptides," Biological & Medicinal Chemistry 7:773-788, 1999.
Hynes, R., "Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report for PCT/US2003/19429 dated Dec. 18, 2003.
International Search Report for PCT/US2003/40881 dated Apr. 26, 2004.
International Search Report for PCT/US2004/038782 dated Jun. 3, 2005.
International Search Report for PCT/US2004/038783 dated May 31, 2005.
International Search Report for PCT/US2006/020249 dated Sep. 27, 2006.
International Search Report for PCT/US2006/030993 dated Feb. 22, 2007.
International Search Report for PCT/US2007/012867 dated Nov. 16, 2007.
International Search Report for PCT/US2007/014457 dated Jul. 15, 2008.
International Search Report for PCT/US2007/021541 dated Jul. 18, 2008.
International Search Report for PCT/US2008/001762 dated Jun. 17, 2008.
International Search Report for PCT/US2010/032568 dated Jul. 30, 2010.
International Search Report for PCT/US2011/031428 dated Jun. 30, 2011.
International Search Report for PCT/US2011/059243 dated Feb. 20, 2012.
International Search Report for PCT/US2012/071519 dated Mar. 8, 2013.
International Search Report for PCT/US2013/067711 dated Jun. 2, 2014.
Inwald, D. P. et al, "Platelet and leucocyte activation in childhood sickle cell disease: association with nocturnal hypoxaemia," British Journal of Haematolgyl 11:474-481, Nov. 2000.
Ishikawa, F. et al., "Chemotherapy-resistant human AML stem cells home to and engraft within the bone-marrow endosteal region," Nature Biotechnology 25(11):1315-1321, Nov. 2007.
Issekutz, T., "Inhibition of In Vivo Lymnphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Kaila, N. et al., "Design and synthesis of sialyl Lewis(x) mimics as E-and P-selectin inhibitors," Med Res Rev 22(6):566-601, Nov. 2002.
Kaila, N. et al.. "β-C-Mannosides as Selecting Inhibitors," Journal of Medicinal Chemistry 45(8): 1563-1566, 2002.
Kannagi et al., "New Globoseries Glycoshingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kannagi, R. et al. "Carbohydrate-mediated cell adhesion in cancer metastasis and angiogenesis," Cancer Sci., 95(5): 377-384 (2004).
Kansas, G., "Selectins and Their Ligands: Current Concepts and Controversies," Blood, 88(9): 3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Kaul, D.K. et al., "Hypoxia/reoxygenation causes inflammatory response in transgenic sickle mice but not in normal mice," The Journal of Clincal Investigation 106(3):411-420, Aug. 2000.
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al., "Immunoaffinity Isolated of a Sialyl-Le.sup.a Oligosaccharide from Human Milk," J. Biochem. 104:591-594, 1988.
Kneuer et al: "Selectins—potential pharmacological targets?" Drug Discovery Today vol. 11, No. 21-22, pp. 1034-1040, Oct. 2006.

(56) References Cited

OTHER PUBLICATIONS

Ko, HL et al. "In Vitro and In Vivo Inhibition of Lectin Mediated Adhesion of *Pseudomonas aeruginosa* by Receptor Blocking Carbohydrates," Infection, 15(4):21-24 (1987).
Koch, Alisa E et al., "Angiogenesis mediated by soluble forms of E-selectin and vascular cell adhesion molecule-1," Nature, 376(6540): 517-519 (1995).
Kogan, T.P. et al., "Novel Synthetic Inhibitors of Selectin-Mediated Cell Adhesion: Synthesis of 1,6-Bis[3-(3-carboxymethlphenyl)-r-(2-alpha.-.sub.D-monopyranosyloxy)p-henyl]hexane (TBC1269)," J Med. Chem 41:1099-1111, 1998.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kogan, T.P. et al., "Rational Design and Synthesis of Small Molecule, Non-oligosaccharide Selectin Inhibitors: (.alpha.D-Mannopyranosyloxy)biphenyl-Substituted Corboxylic Acids," J. Med. Chem. 38: 4976-4984, Dec. 22, 1995.
Kohler and Milstein, "Continuous cultures of fused cells secreting antibody of predefined specificity," Nature 256:495-497, 1975.
Kohler and Milstein, "Derivation of specific antibody-producing tissue culture and tumor lines by cell fusion," Eur. J. Immunol. 6:511-519, 1976.
Kojima and Hakomori, "Specific Interaction between Gangliotriaosylceramide (G.sub.g3) and Sialosyliactosylceramide (G.sub.M3) as a Basis for Specific Cellular Recognition between Lymphoma and Melanoma Cells," J. Biol. Chem. 264(34):20159-20162, 1989.
Kolb, H. C. et al., "Development of Tool for the Design of Selectin Antagonists," Chem. Eur. J. 3(10):1571-1578, 1997.
Kolb, H. C. et al., "Recent progress in the glycodrug area," Pure & Applied Chemistry 89(9):1879-1884, 1997.
Koprowski et al., "Colorectal Carcinoma Antigens Detected by Hybridoma Antibodies," Somatic Cell Genetics 5(6):957-972, 1979.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific *Pseudomonas aeruginose* lectin, PA-I, to glycosphingolipids and other glycoconjugates," Glycoconjugate Journal, 11:292-298 (1994).
Larsen et al., PADGEM-Dependent Adhesion of Platelets to Monocytes and Neutrophils is Mediated by a Lineage-Specific Carbohydrate, LNF III (CD15), Cell 63:467-474, 1990.
Lee et al., "A new method of sequencing linear oligosaccharides on gels using charged, fluorescent conjugates" Carbohydrate Research, vol. 214, 1991, pp. 155-168, XP000226749.
Leppla, S H et al., "Anthrax Toxin Fusion Proteins for Intracellular Delivery of Macromolecules," Journal of Applied Microbiology., 87(2): p. 284 (Aug. 1, 1999).
Ley, K. "The role of selectins in inflammation and disease," Trends in Molecular Medicine, 9(6): 263-268 (Jun. 2003).
Ley, K. et al. "Selectins in T-cell Recruitment to Non-Lymphoid Tissues and Sites of Inflammation," Nature Reviews, 4: 1-11 (May 2004).
Li, B., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Lingenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, *Pseudomonas auroginosa*," Glycobiology 13(11): 854, Abstract No. 104, Oct. 2003.
Mann, AP et al. "Identification of Thioaptamer Ligand against E-Sectin: Potential Application for Inflamed Vasculature Targeting." PLoS ONE, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "Heparin inhibits the flow adhesion of sickle red blood cells to Pselectin," Blood 100(10):3790-3796, Nov. 15, 2002.
Matsui, N. M. et al., "The Novel Adhesion of Erythrocytes to P-Selecting in Sickle Cell Disease," Blood 96(11)Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Menendez, A., et al., "A Peptide Inhibitor of HIV-1 Neutralizing Antibody 2G12 is not a Structural Mimic of the Natural Carbohydrates Epitope on gp120," The FASEB Journal 22:1380-1382, May 2008.
Moore, P. L. et al., "Evolution of an HIV Glycan-Dependent Broadly Neutralizing Antibody Epitope Through Immune Escape," Nature Medicine doi:10.1038/nm.2985 pp. 1-6, Oct. 2012.
Mosley et al., "Recent Patents Regarding the Discovery of Small Molecule CXCR4 Antagonisits," Expert Opin. Ther. Patents 19(1):23-38, 2009.
Mulligan and Berg, "Selection for animal cells that express the *Escherichia coli* gene coding for xanthine-gunine phosphoribosyltransferase," Proc. Natl. Acad. Sci. USA 78:2072-2076, 1981.
Nagel, R. L., "A Knockout of a Transgenic Mouse-Animal Models of Sickle Cell Anemia," The New England Journal of Medicine 339:194-195, Jul. 16, 1998.
Narita, T. et al. "Corticosteroids and medroxyprogesterone acetalte inhibit the induction of brease cancer cells," Anticancer Research, 15(6B): 2523-2527 (1995)—Abstract.

(56) References Cited

OTHER PUBLICATIONS

Narum, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).
Natarajan, M.M. et al., "Adhesion of sickle red blood cells and damage to interleukinIbeta stimulated endothelial cells under flow in vitro," Blood 87:4845-4852, 1996.
Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).
Nicolaou et al., "Total Synthesis of the Tumor-Associated Le.sup.x Family of Glycosphingolipids," J. Amer. Chem. Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Norman et al., "Sialyl Lewisx(sLex) and an sLex Mimetic, CGP89669A, Disrupt E-Selectin-Dependent Leukocyte Rolling In Vivo," Blood, 91(2):475-483 (Jan. 15, 1998).
Notice of Allowance mailed Dec. 11, 2008 in U.S. Appl. No. 11/501,464.
Notice of Allowance mailed Dec. 3, 2012 in U.S. Appl. No. 12/768,173.
Notice of Allowance mailed Feb. 9, 2011 in U.S. Appl. No. 11/973,891.
Notice of Allowance mailed May 25, 2011 in U.S. Appl. No. 12/069,436.
Notice of Allowance mailed May 9, 2012 in U.S. Appl. No. 12/370,826.
Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495, 1986.
Nutku, E. et al., "Ligation of Siglec-8: a selective mechanism for induction of human eosinophil apoptosis," Blood, 101(12): 5014-5020 (2003).
Obermajer, N. et al., "Design, synthesis and activity evaluation of mannose-based DC-SIGN antagonists," Molecular Diversity 15:347-360, May 2011.
Office Action mailed Apr. 5, 2012 in U.S. Appl. No. 12/418,774.
Office Action mailed Apr. 8, 2010 in U.S. Appl. No. 11/973,891.
Office Action mailed Apr. 8, 2013 in U.S. Appl. No. 13/566,522.
Office Action mailed Aug. 13, 2008 in U.S. Appl. No. 10/992,238.
Office Action mailed Aug. 8, 2006 in U.S. Appl. No. 10/601,080.
Office Action mailed Feb. 11, 2013 in U.S. Appl. No. 13/566,522.
Office Action mailed Feb. 23, 2006 in U.S. Appl. No. 10/742,631.
Office Action mailed Feb. 23, 2011 in U.S. Appl. No. 11/973,891.
Office Action mailed Feb. 23, 2012 in U.S. Appl. No. 12/370,826.
Office Action mailed Feb. 6, 2008 in U.S. Appl. No. 10/992,238.
Office Action mailed Feb. 6, 2014 in U.S. Appl. No. 14/057,729 (Reissue Application of U.S. Patent No. 8039442).
Office Action mailed Jan. 31, 2014 in U.S. Appl. No. 12/418,774.
Office Action mailed Jul. 14, 2010 in U.S. Appl. No. 12/069,436.
Office Action mailed Jul. 16, 2014 in U.S. Appl. No. 13/877,633.
Office Action mailed Jul. 8, 2011 in U.S. Appl. No. 12/370,826.
Office Action mailed Jun. 14, 2007 in U.S. Appl. No. 10/992,480.
Office Action mailed Jun. 19, 2012 in U.S. Appl. No. 12/768,173.
Office Action mailed Jun. 2, 2006 in U.S. Appl. No. 10/601,080.
Office Action mailed Jun. 20, 2013 in U.S. Appl. No. 13/224,847.
Office Action mailed Jun. 23, 2010 in U.S. Appl. No. 11/920,499.
Office Action mailed Jun. 6, 2005 in U.S. Appl. No. 10/742,631.
Office Action mailed Mar. 18, 2013 in U.S. Appl. No. 13/224,847.
Office Action mailed Mar. 20, 2013 in U.S. Appl. No. 13/081,068.
Office Action mailed Mar. 25, 2011 in U.S. Appl. No. 12/370,826.
Office Action mailed May 10, 2011 in U.S. Appl. No. 12/302,092.
Office Action mailed May 15, 2013 in U.S. Appl. No. 13/081,068.
Office Action mailed May 25, 2011 in U.S. Appl. No. 12/304,879.
Office Action mailed May 28, 2008 in U.S. Appl. No. 11/501,464.
Office Action mailed Nov. 2, 2005 in U.S. Appl. No. 10/742,631.
Office Action mailed Nov. 25, 2011 in U.S. Appl. No. 13/093,611.
Office Action mailed Oct. 13, 2010 in U.S. Appl. No. 11/920,499.
Office Action mailed Oct. 13, 2011 in U.S. Appl. No. 12/418,774.
Office Action mailed Oct. 29, 2010 in U.S. Appl. No. 12/069,436.
Office Action mailed Sep. 12, 2008 in U.S. Appl. No. 11/501,464.
Office Action mailed Sep. 20, 2010 in U.S. Appl. No. 11/973,891.
Office Action mailed Sep. 25, 2007 in U.S. Appl. No. 10/992,238.
Office Action mailed Sep. 27, 2011 in U.S. Appl. No. 12/304,879.
Orhlein, R., "Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al., "A Bisubstrate Analog Inhibitor for .alpha.(1.fwdarw.2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Patton, J. T. et al., "GMI-1070: a Small Glycomimetic, Pan-selectin Antagonist that Improves Blood Flow and Inhibits Blood Cell Adhesion in Sickle Mice," Abstract ID: ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Sepcific Substrate for a Sensitive Assay of a-Amylase by Fluorescence Quenching," Angew. Chem. Int. Ed. Engl. 34(11): 1239-1241 (1995).
Pejchal R. et al., "A Potent and Broad Neutralizing Antibody Recognizes and Penetrates the HIV Glycan Shield," Science 334:1097-1103, Nov. 2011.
Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 1 1-16 dissection of protein translocation through the anthrax toxin pore," Angewandte Chemie. 50(10): 2294-2296 (Mar. 1, 2011).
Perret, S. et al., "Structural basis for the interaction between human milk oligosaccharides and the bacterial lectin PA-IIL of *Pseudomonas aeruginosa*," Biochem. J. 389: 325-332, 2005.
Phillips et al., "ELAM-1 Mediates Cell Adhesion by Recognition of a Carbohydrate Ligands, Sialyl-Le.sup.x," Science 250:1130-1132, 1990.
Picker et al., "The Neutrophil Selectin LECAM-1 Presents Carbohydrate Ligands to the Vascular Selectins ELAM-1 and GMP-140," Cell 66:921-933, 1991.
Prokazova et al., "Sialylated lactosylceramides. Possible inducers of non-specific immunosuppression and ahteroscierotic lesions," European Journal of Biochemistry 172:1-6, 1988.
Purton, L. E. et al., "Limiting Factors in Murine Hematopoietic Stem Cell Assays," Cell Stem Cell 1: 263-270, Sep. 2007.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recgnition. I. Extent and Specificity of Cell Adhesion Triggered by Carbohydrate-reactive Proteins (Glycosidases and Lectins) and by Fibronectin," J. Cell Biol. 88:127-137, 1981.
Reina, J. J. et al., "1,2-Mannobioside Mimic: Synthesis, DC-SIGN Interaction by NMR and Docking, and Antiviral Activity," ChemMedChem 2: 1030-1036, 2007.

(56) References Cited

OTHER PUBLICATIONS

Rice and Bevilacqua, "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Ruoslahti and Pierschbacher, "New Perspectives in Cell Adhesion: RGD and Integrins," Science 238:491-497, 1987.
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan, C. N. et al., "Exploiting the Defensive Sugars of HIV-1 for Drug and Vaccine Design," Nature 446:1038-1045, Apr. 2007.
Scanlan, C. N. et al., "The Broadly Neutralizing Anti-Human Immunodeficiency Virus Type 1 Antibody 2G12 Recognizes a Cluster of a 1-2 mannose Residues on the Outer Face of gp120," Journal of Virology 76:7306-7321, Jul. 2002.
Scharfman, A. et al., "*Pseudomonas aeruginosa* binds to neoglycoconjugates bearing mucin carbohydrate determinants and predominantly to sialyl-Lewis x conjugates," Glycobiology 9(8): 757-764, 1999.
Scharfman, A. et al., "Recognition of Lewis x Derivatives Present on Mucins by Flagellar Components of *Pseudomonas aeruginosa*," Infection and Immunity 69(9): 5243-5248, Sep. 2001.
Schief, W. R. et al., "Challenges for Structure-Based HIV Vaccine Design," Current Opinion in HIV and AIDS 4:431-440, 2009.
Schwizer, D. et al. "Pre-organization of the Core Structure of E-Selectin Antagonist," Chemistry—A European Journal, 18(5): 1342-1351 (Jan. 2012).
Shan, M. et al., "HIV-1 gp120 Mannoses Induce Immunosuppressive Responses from Dendritic Cells," PLoS Pathogens 3(11):e169 1637-1650, Nov. 2007.
Shitara et al., "Application of Anti-Sialyl Le.sup.a Monoclonal antibody, KM231, for Immunotherapy of Cancer," Anticancer Res. 11:2003-2014, 1991.
Simanek Eric A. et al. "Selectin-carbohydrate interactions: from natural ligands to designed mimics", Chemical Reviews vol. 98, No. 2, pp. 833-862, Jan. 1998.
Singh et al., "Evaluation of a CXCR4 Antagonist in a Xenograft Mouse Model of Inflammatory Breast Cancer," Clin. Exp. Metastasis 27:233-240, Mar. 2010.
Sipkins, Dorothy A. et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey et al., "Circulating Activated Endothelial Cells in Sickle Cell Anemia," The New England Journal of Medicine 337:1584-1590, Nov. 27, 1997.
Solovey, AA et al. "Modulation of endothelial cell activation in sickle cell disease: a pilot study," Blood, 97(7): 1937-1941 (Apr. 2001).
Sprengard, U. et al., "Synthesis and Biological Activity of Novel Sialyl-Lewis.sup.X Conjugates," Bioorganic & Medicinal Chemistry Letters 6(5): 509-514, 1996.
Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23): 11374-11381, 1988.
Stephens and Cockett, "The construction of highly efficient and versatile set of mammalian expression vectors," Nucleic Acids Research. 17:7110, 1989.

Stevenson, J. et al., "Differential metastasis inhibition by clinicially relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al., "Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Supplementary European Search Report in EP 03739223 dated Jan. 16, 2009.
Suzuma, I. et al. "Contribution of E-Selectin to Cellular Infiltration during Endotoxin-Induced Uveitis," Invest. Ophthalmol. Vis. Sci., 39: 1620-1630 (1998).
Svenson and Lindberg, "Coupling of Acid Labile *Salmonella* Specific Oligosaccharides to Macromolecular Carriers," J. Immunol. Meth. 25:323-335, 1979.
Symon, FA et al. "Selectins and their Counter receptors: a bitter sweet attraction," Thorax, 51: 1155-1157 (1996).
Tabarani G. et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis A.sup.1," Biochem. Biophys. Res. Commun. 179(2):713-719, 1991.
Takahashi, Takashi et al., "Design and Synthesis of a Water-Soluble Taxol Analogue: Taxol-Sialyl Conjugate," Bioorg. & Med. Chem. Letters 8:113-116, 1998.
Takeichi, M., "Cadherins: a molecular family essential for selective cell-cell adhesion and animal morphogenesis," Trends Genet. 3(8):213-217, 1987.
Tamamura, H. et al. "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka, T. et al. "Azamacrocyclic Metal Complexes as CXCR4 Antagonists," ChemMedChem, 6: 834-839 (2011).
Tedder, TF et al. "The selectins: vascular adhesion molecules," FASEB J, 9(10): 866-73 (1995).
The Merck Maual of Diagnosis and Therapy, Seventeenth Edition, published 1999 by Merck Research Laboratories, pp. 397, 398, 948, 949, 1916, 1979-1981.
Thoma G. et al., "A readily Available, Highly Potent E-Selectin Antagonists," Angew. Chem. Int. Ed. 40(19): 3644-3647, 2001.
Thoma, G et al., "Nanomoiar E-selectin inhibitors: 700-fold potentiation of affinity by multivalent ligand presentation," Journal of the American Chemical Society, 123(41): 10113-10114 (Oct. 17, 2001).
Thoma, G. et al., "Preorganization of the Bioactive Conformation of Sialyl Lewis.sup.X Analogues Correlates with Their Affinity to E-Selectin," Angew. Che. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz, A. et al., "Probing the carbohydrate recognition domain of E-selectin: The importance of the acid orientation in sLex mimetics," Bioorg. Med. Chem., 18(1): 19-27 (2010).
Toepfer, et al., "Synthesis of novel mimetics of the sialyl Lewis X determinant," Tetrahedron Letter, 36(50): 9161-9164 (1995).
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as

(56) References Cited

OTHER PUBLICATIONS required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
U.S. Appl. No. 10/601,080, filed Jun. 19, 2003.
U.S. Appl. No. 10/742,631, filed Dec. 19, 2003.
U.S. Appl. No. 10/992,238, filed Nov. 18, 2004.
U.S. Appl. No. 11/920,499, filed Nov. 16, 2007.
U.S. Appl. No. 12/302,092, filed Nov. 24, 2008.
U.S. Appl. No. 12/304,879, filed Dec. 15, 2008.
U.S. Appl. No. 12/418,774, filed Apr. 6, 2009.
U.S. Appl. No. 13/081,068, filed Nov. 15, 2013.
U.S. Appl. No. 13/093,611, filed Apr. 25, 2011.
U.S. Appl. No. 13/224,847, filed Sep. 2, 2011.
U.S. Appl. No. 13/566,522, filed Aug. 3, 2012.
U.S. Appl. No. 13/785,439, filed Mar. 5, 2013.
U.S. Appl. No. 13/877,633, filed Jun. 17, 2013.
U.S. Appl. No. 14/057,729, filed Oct. 13, 2013, (Re-Issue Application of U.S. Patent No. 8,039,442).
U.S. Appl. No. 14/080,926, filed Nov. 15, 2013.
U.S. Appl. No. 14/106,662, filed Dec. 13, 2013.
U.S. Appl. No. 14/367,561, filed Jun. 20, 2014.
Ueda et. al., "Structure-Activity Relationships or Cyclic Peptide-Based Chemokine Receptor CXCR4 Antagonists: Disclosing the Importance of Side-Chain and Backbone Functionalities," J. Med. Chem. 50:192-198, 2007.
Venkataraman, Nitya, et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann, H. et al., "Synthesis of 2-Acetamindo-2-Deoxyglucosylasparagine Glyco-Tripeptide and -Pentapeptides by Selective C-and N-Terminal Elongation of the Peptide Chain," Carbohydrate Research 196: 75-93, 1990.
Walker, L. M. et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, GM. "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang, L.X. et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.

Wang, S.K. et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Wang, Y. et al. "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Ward and Mulligan, "Blocking of adhesion molecules in vivo as anti-inflammatory therapy," Immunology 1: 165-171, 1994.
Wesche, Jorgen et al., "Characterization of membrane translocation by anthrax protective antigen," Biochemistry, 37(45): 15737-15746 (Nov. 10, 1998).
Whisler and Yates, "Regulation of Lymphocyte Responses by Human Gangliosides. I. Characteristics of Inhibitory Effects and the Induction of Impaired Activation," Journal of Immunology 125(5):2106-2111, 1980.
Winnard, P. et al., "Real time non-invasive imaging of receptor-ligand interactions in vivo," J. Cell. Biochem., 90: 454-463 (2003).
Winzer, K. et al. "The *Pseudomonas aeruginosa* Lectins PA-IL and PA-IIL are Controlled by Quorom Sensing and by RpoS," J. Bacteriol. 182(22): 6401-6411 (2000).
Wu, B. et al. "Structures of the CXCR4 Chemokine GPCR with Small-Molecule and Cyclic Peptide Antagonists," Science, 330(6007): 1066-1071 (Nov. 2010).
Xu, J. et al., "Molecular insights and therapeutic targets for diabetic endothelial dysfunction," Circulation, 120: 1266-1286 (2009).
Yamazaki, F. et al., "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zheng, CX et al. "The prognostic value of preoperative serum levels of CEA, CA19-9 and CA72-4 in patients with colrectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mcie with severe acute pancreatitis," Chongqing Yixue, 35(7): 624-628 (2006)—Abstract.
Zopf et al., "Affinity Purification of Antibodies Using Oligosaccharide-Phenethylamine Derivatives Coupled to Sepharose." Meth. Enzymol. 50:171-175, 1978.

\* cited by examiner

E-SELECTIN ANTAGONISTS

CROSS REFERENCE TO RELATED APPLICATIONS

This application is a United States national stage application filed under 35 U.S.C. §371 of International Patent Application No. PCT/US2011/051234 accorded an international filing date of Sep. 12, 2011; which application claims the benefit under 35 U.S. §119(e) of U.S. Provisional Patent Application No. 61/382,716 filed Sep. 14, 2010; which applications are incorporated herein by reference in their entirety.

BACKGROUND

1. Technical Field

The present invention relates generally to compounds, compositions and methods for inhibiting E-selectin, and more specifically to particular glycomimetics which are E-selectin antagonists.

2. Description of the Related Art

When a tissue is infected or damaged, the inflammatory process directs leukocytes and other immune system components to the site of infection or injury. Within this process, leukocytes play an important role in the engulfment and digestion of microorganisms. Thus, the recruitment of leukocytes to infected or damaged tissue is critical for mounting an effective immune defense.

Selectins are a group of structurally similar cell surface receptors that are important for mediating leukocyte binding to endothelial cells. These proteins are type 1 membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin and L-selectin. E-selectin is found on the surface of activated endothelial cells, which line the interior wall of capillaries. E-selectin binds to the carbohydrate sialyl-Lewis$^x$ (SLe$^x$), which is presented as a glycoprotein or glycolipid on the surface of certain leukocytes (monocytes and neutrophils) and helps these cells adhere to capillary walls in areas where surrounding tissue is infected or damaged; and E-selectin also binds to sialyl-Lewis$^a$ (SLe$^a$), which is expressed on many tumor cells. P-selectin is expressed on inflamed endothelium and platelets, and also recognizes SLe$^x$ and SLe$^a$, but also contains a second site that interacts with sulfated tyrosine. The expression of E-selectin and P-selectin is generally increased when the tissue adjacent to a capillary is infected or damaged. L-selectin is expressed on leukocytes. Selectin-mediated intercellular adhesion is an example of a selectin-mediated function.

Modulators of selectin-mediated function include the PSGL-1 protein (and smaller peptide fragments), fucoidan, glycyrrhizin (and derivatives), anti-selectin antibodies, sulfated lactose derivatives, and heparin. All have shown to be unsuitable for drug development due to insufficient activity, toxicity, lack of specificity, poor ADME characteristics and/or availability of material.

Although selectin-mediated cell adhesion is required for fighting infection and destroying foreign material, there are situations in which such cell adhesion is undesirable or excessive, resulting in tissue damage instead of repair. For example, many pathologies (such as autoimmune and inflammatory diseases, shock and reperfusion injuries) involve abnormal adhesion of white blood cells. Such abnormal cell adhesion may also play a role in transplant and graft rejection. In addition, some circulating cancer cells appear to take advantage of the inflammatory mechanism to bind to activated endothelium. In such circumstances, modulation of selectin-mediated intercellular adhesion may be desirable.

Accordingly, there is a need in the art for identifying inhibitors of selectin-mediated function, e.g., of selectin-dependent cell adhesion, and for the development of methods employing such compounds to inhibit conditions associated with excessive selectin activity. The present invention fulfills these needs and further provides other related advantages.

BRIEF SUMMARY

Briefly stated, this invention provides compounds, compositions and methods for inhibiting E-selectin. The compounds are particular E-selectin antagonists. Such compounds may be combined with a pharmaceutically acceptable carrier or diluent to form a pharmaceutical composition. The compounds or compositions may be used in a method to inhibit an E-selectin-mediated function, such as inhibiting an E-selectin-mediated intercellular adhesion.

In one aspect of the present invention, a compound is provided having one of the following formulae:

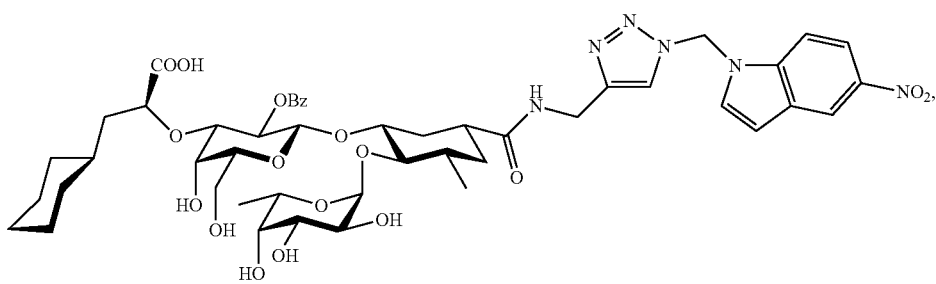

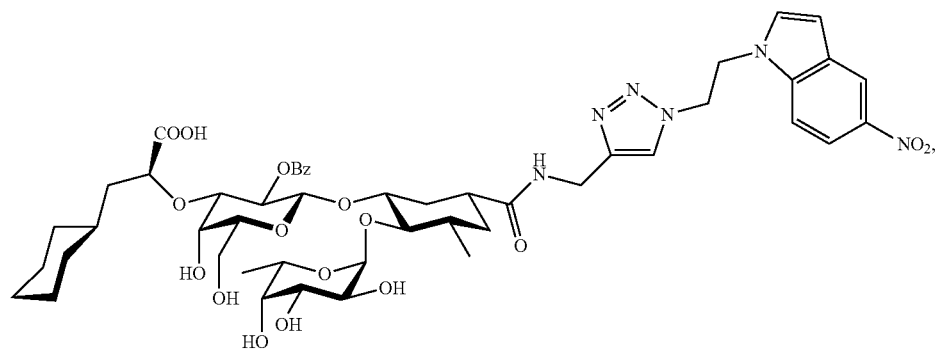
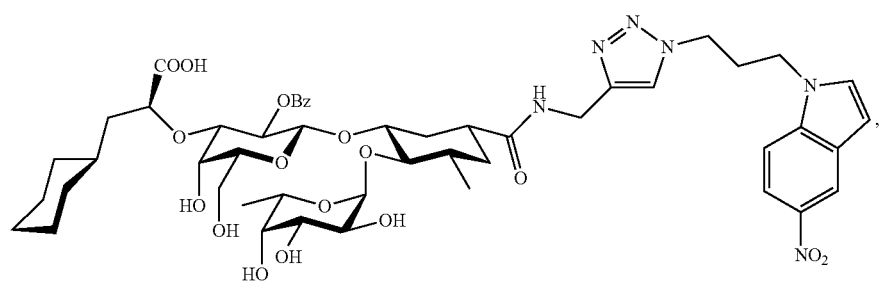
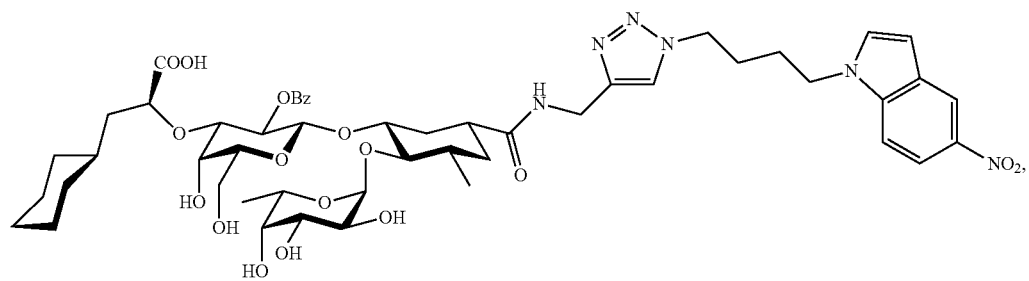
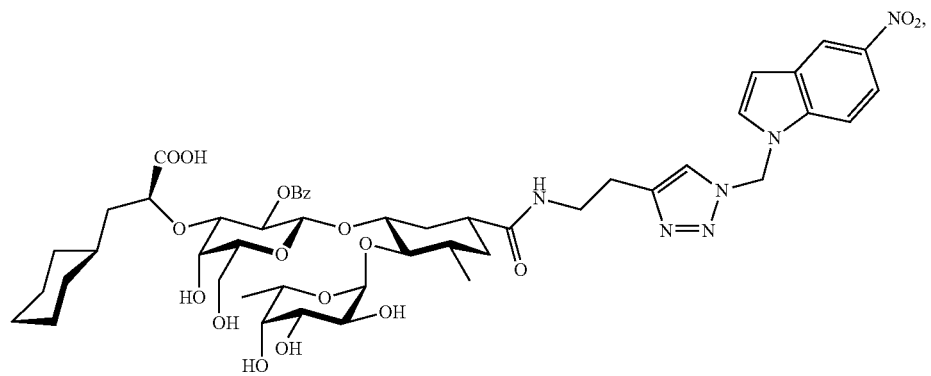
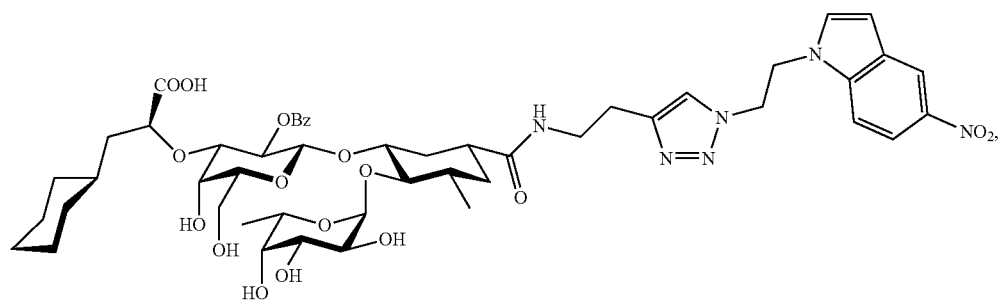

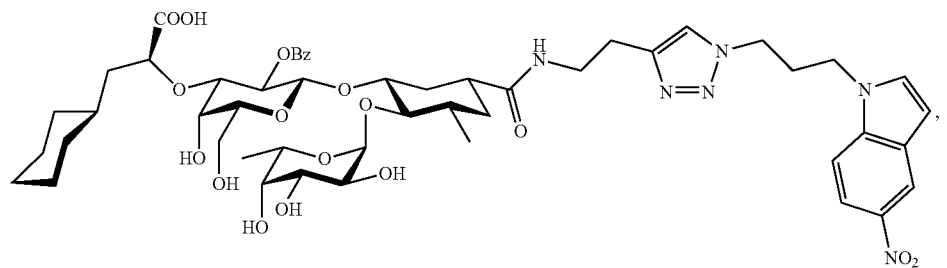
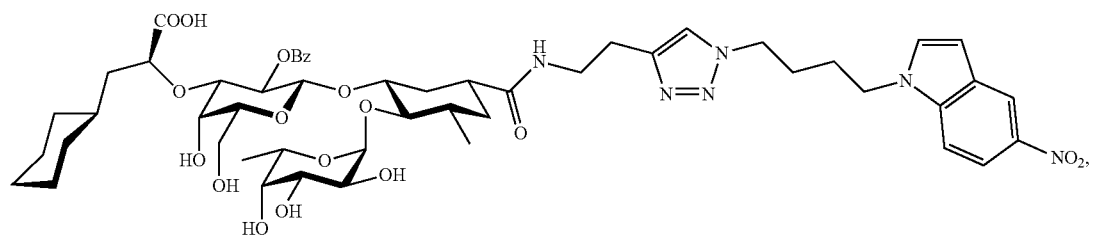
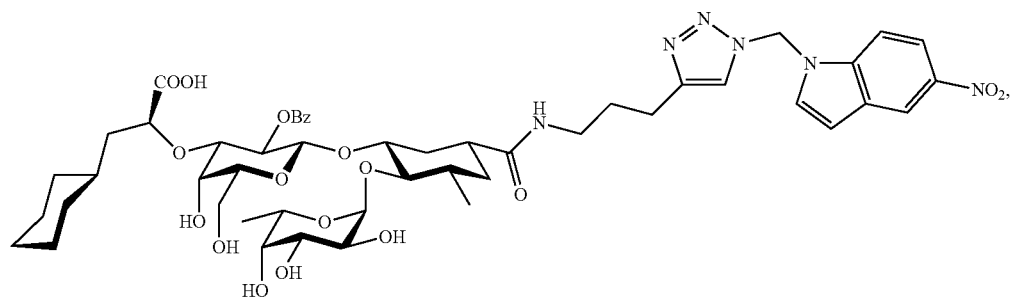
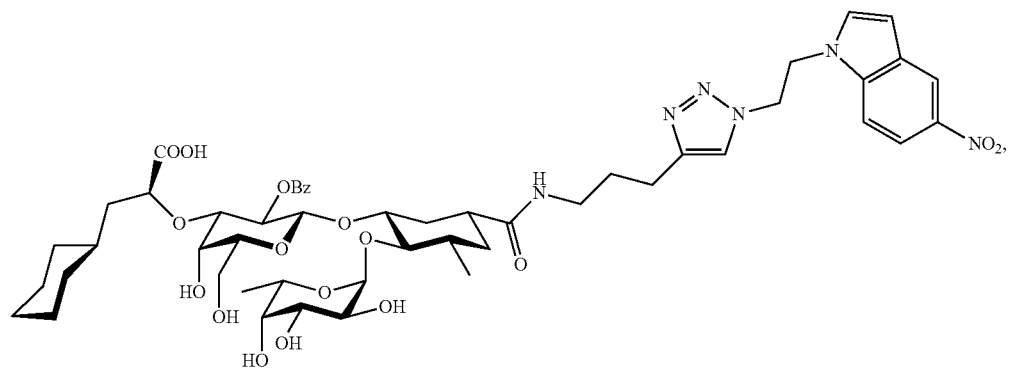
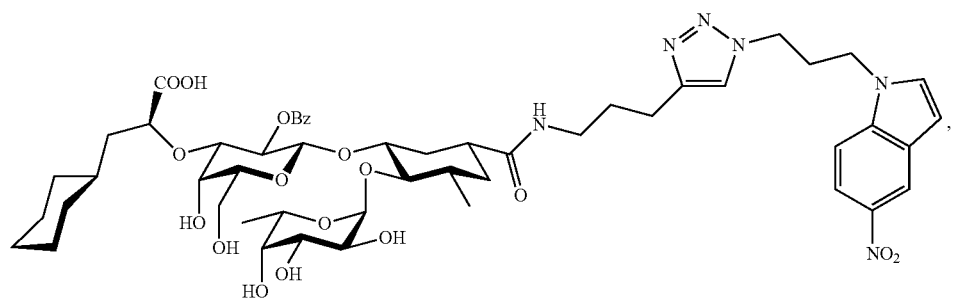

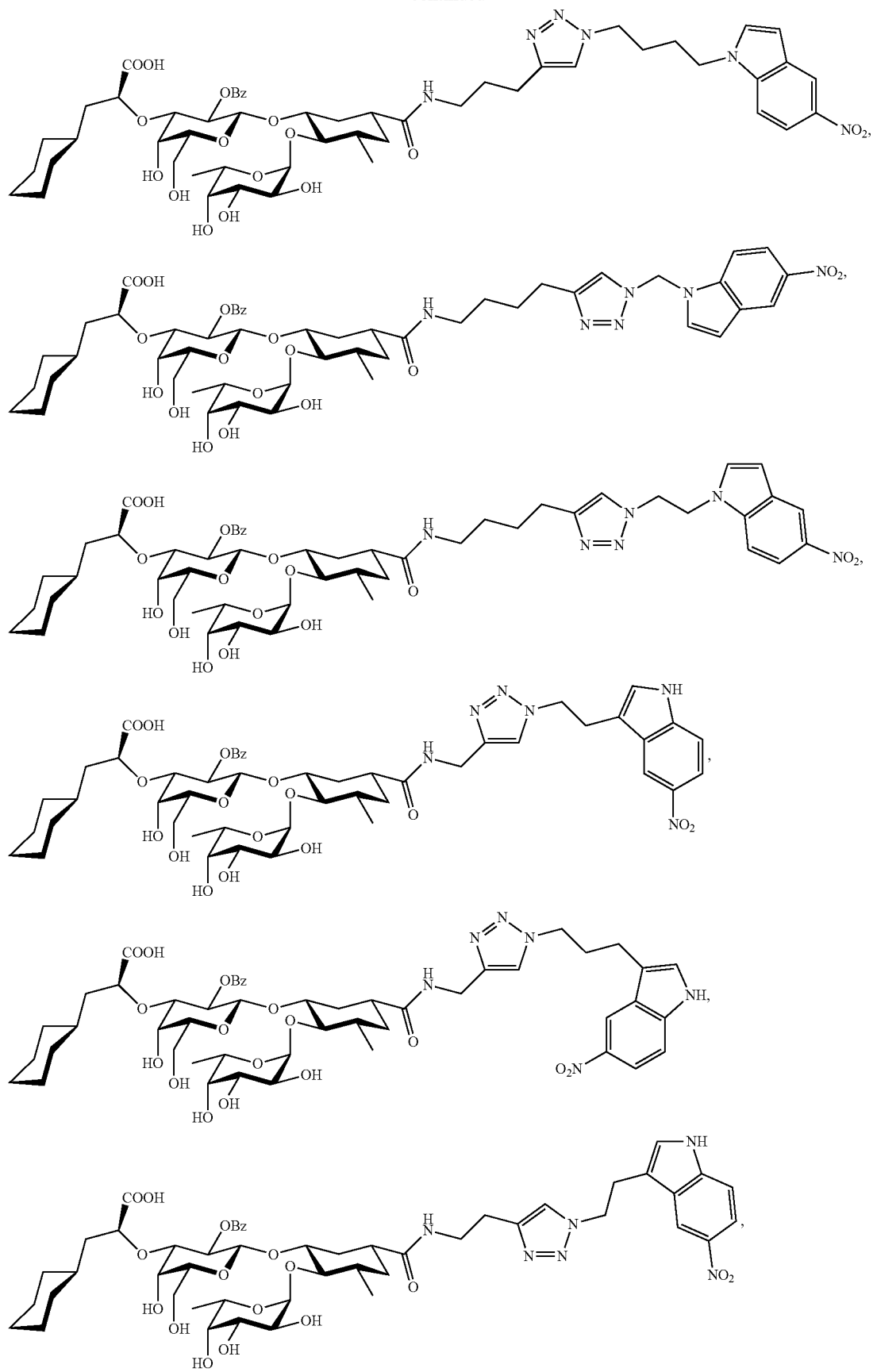

-continued
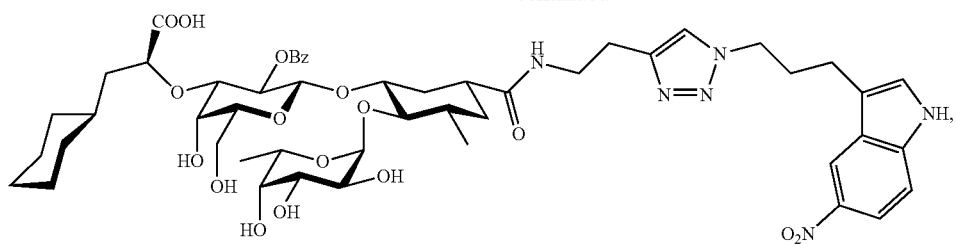
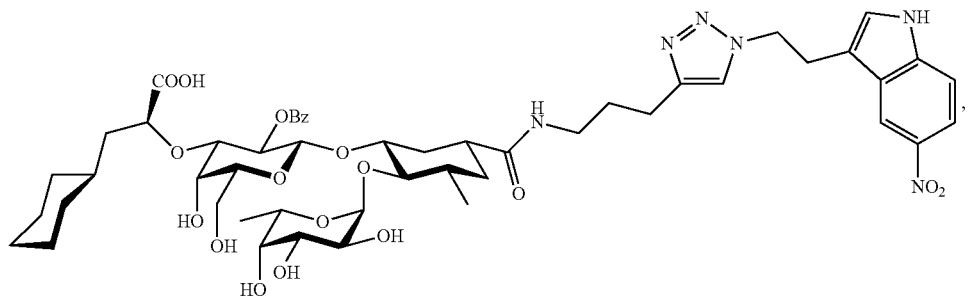
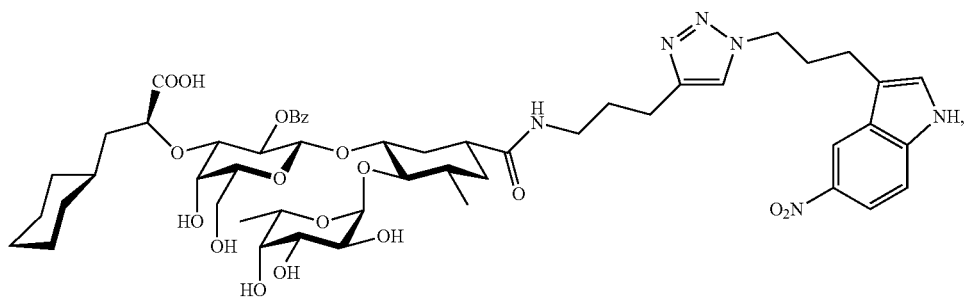
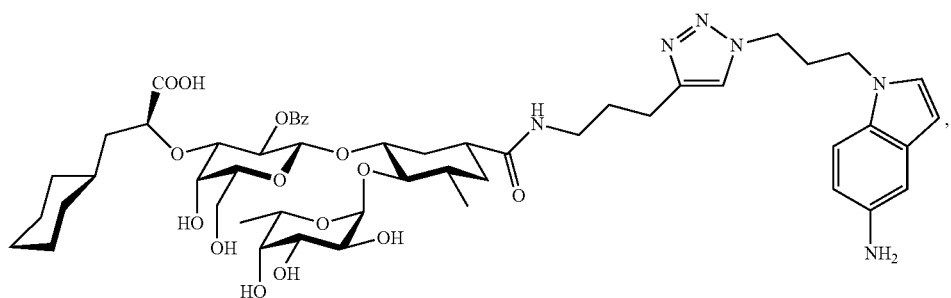
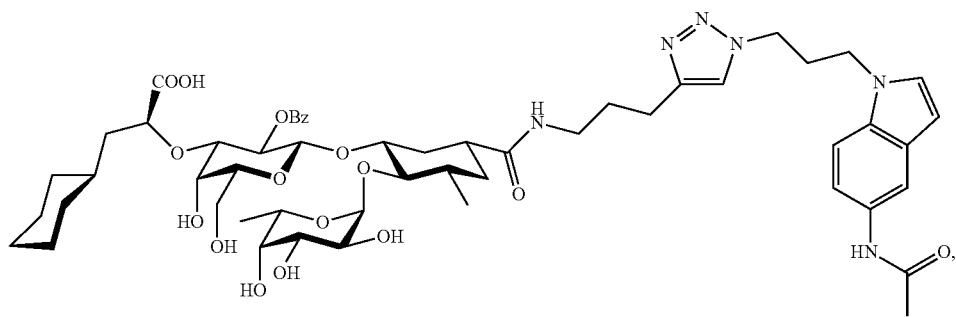

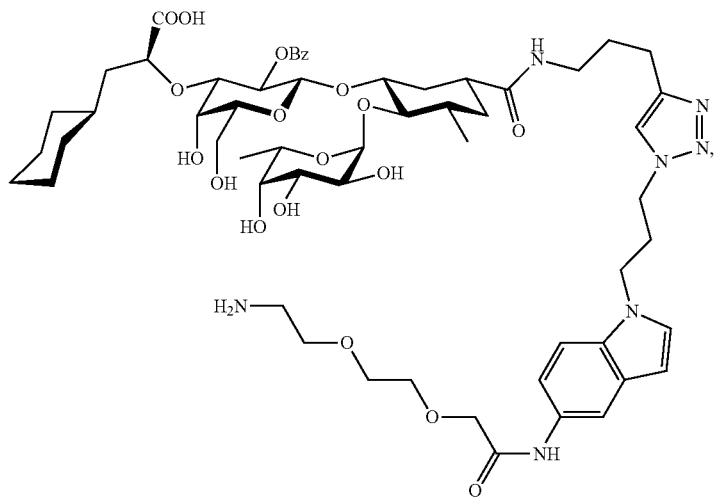

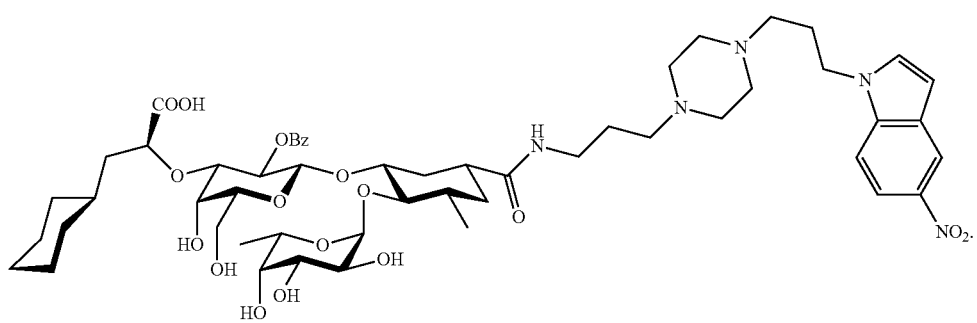

A compound of the present invention includes physiologically acceptable salts thereof. A compound of the present invention in combination with a pharmaceutically acceptable carrier or diluent provides a composition of the present invention. In the chemical formula herein, the abbreviation "Me" or a single line extending from a carbon implied by the intersection of two other lines, represents a methyl group.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1:
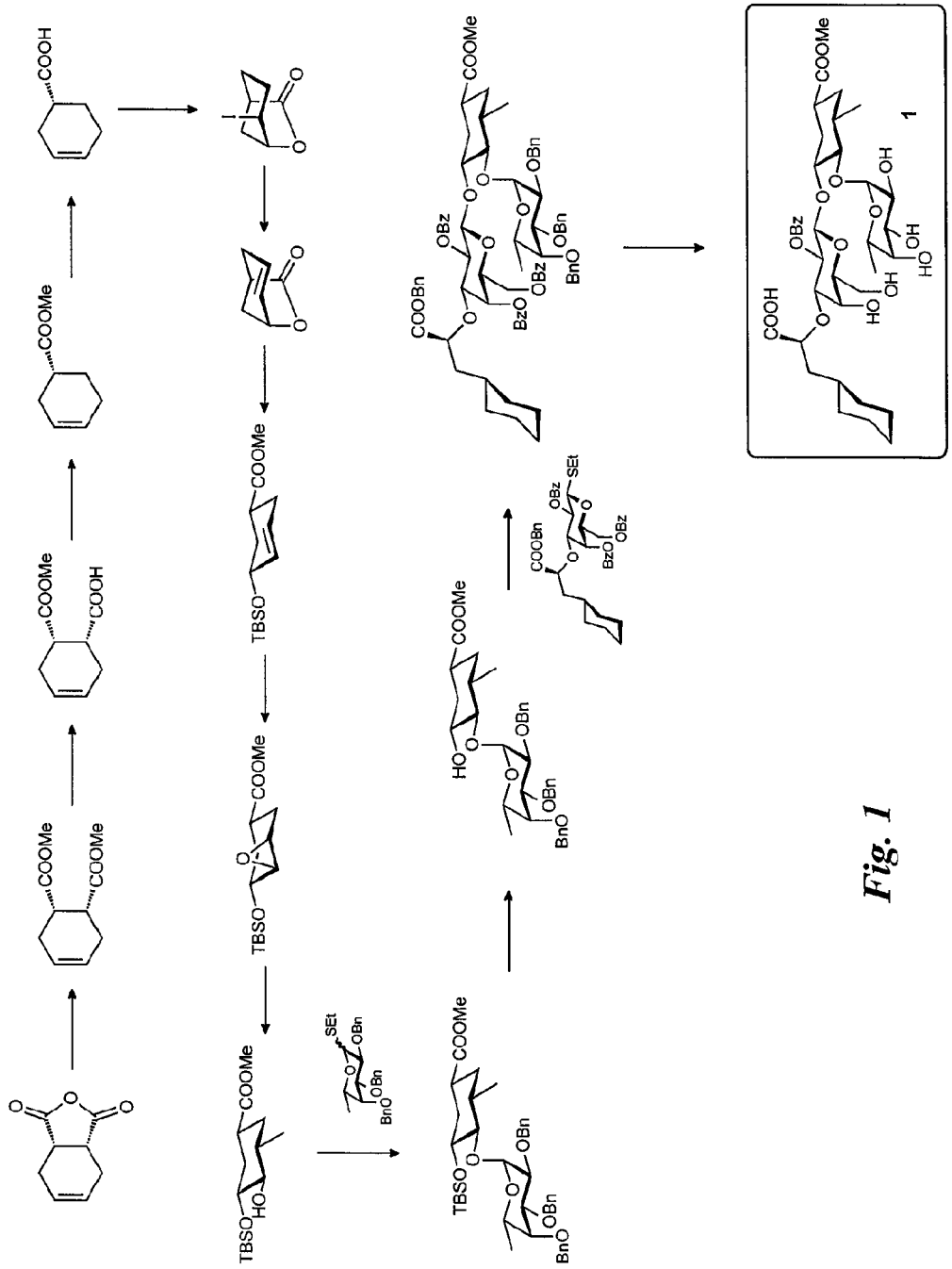
FIG. 1 is a diagram illustrating the synthesis of the precursor glycomimetic ligand 1. Glycomimetic ligand 1 was synthesized according to International Application Publication No. WO 2008/060378 (e.g., Example 1 and FIG. 1).
Figure 2:
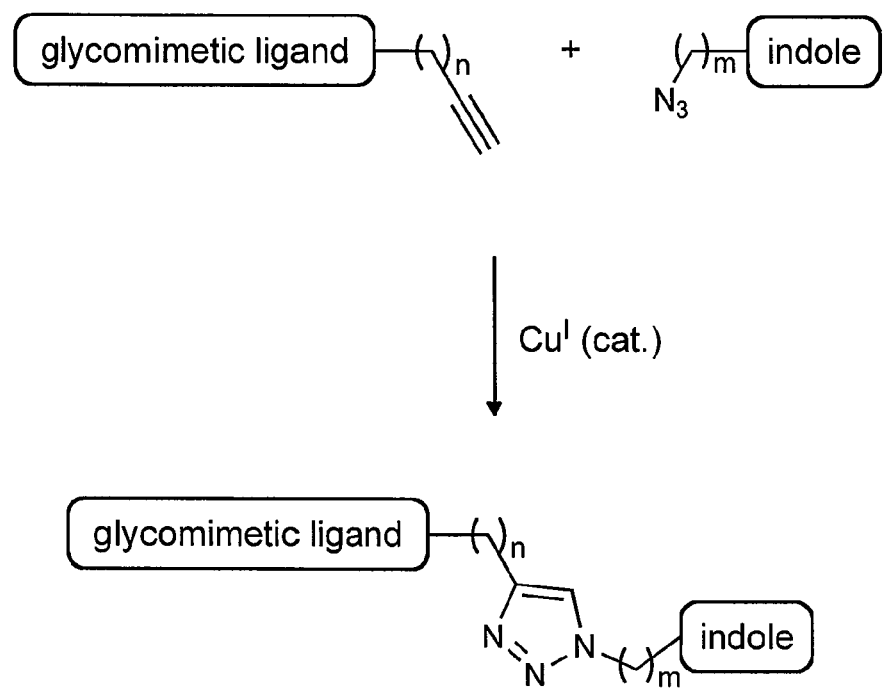
FIG. 2 is a diagram of a general description of the synthesis of selectin antagonists with triazole linker.

As noted above, the present invention provides compounds which are E-selectin antagonists, compositions thereof and methods for inhibiting E-selectin-mediated functions. Such antagonists may be used in vitro or in vivo, to inhibit E-selectin-mediated functions in a variety of contexts. Examples of E-selectin-mediated functions include intracellular adhesion.

The E-selectin antagonists of the present invention are particular compounds that surprisingly show significant inhibitory activity at nanomolar concentrations. The compounds include physiologically acceptable salts thereof. The compounds have the following formulae:

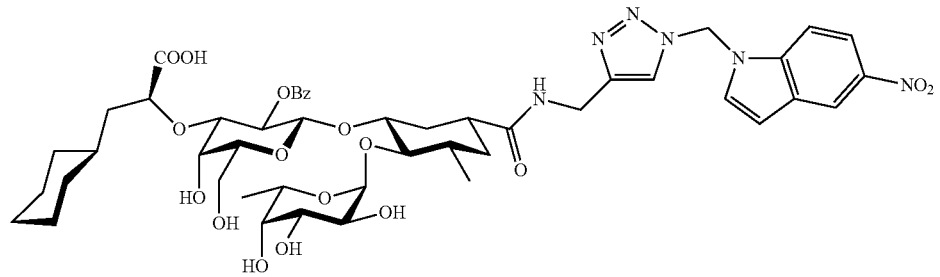
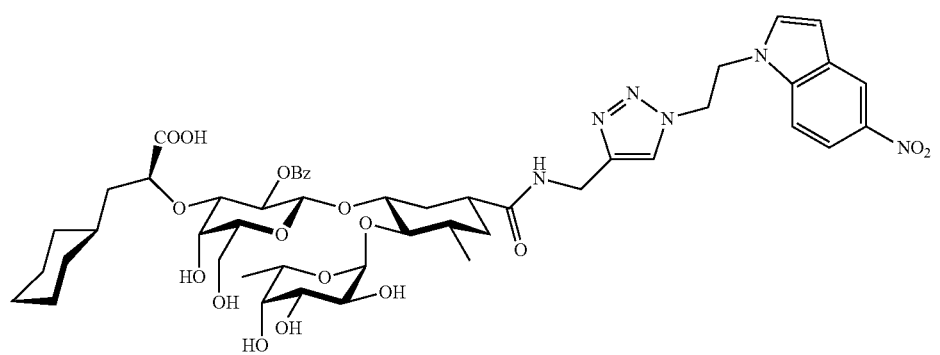
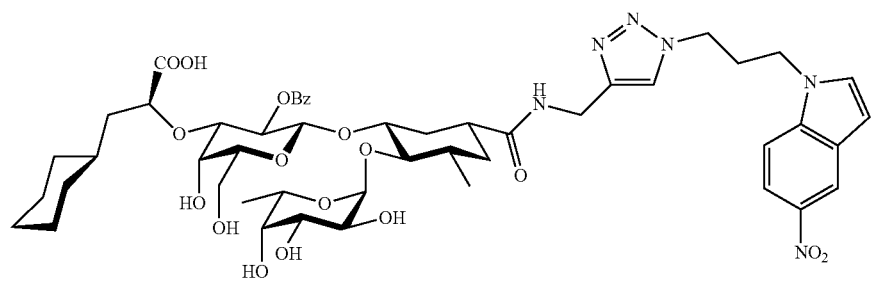
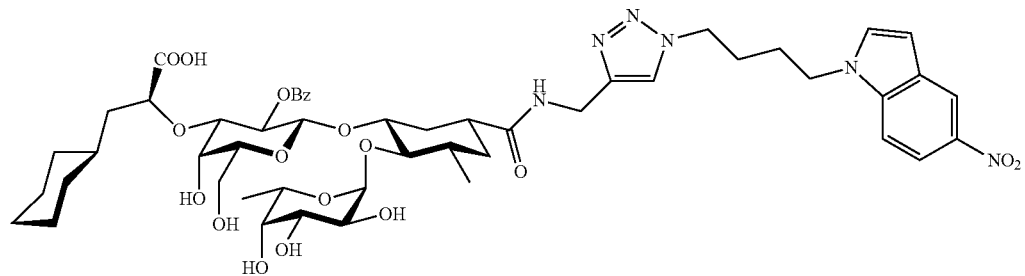
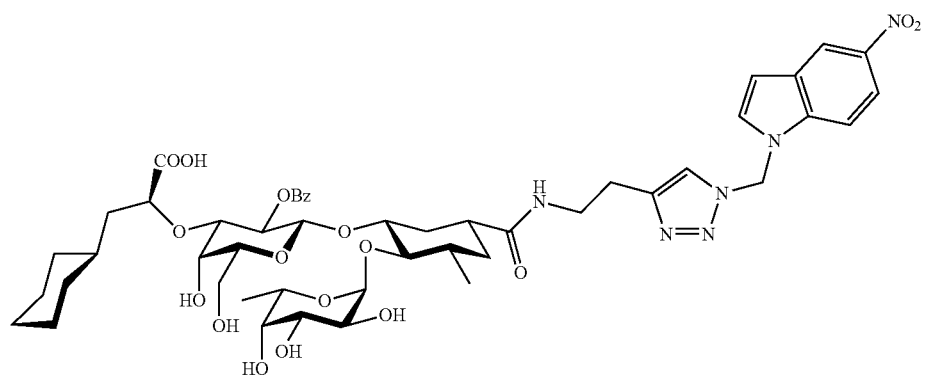

-continued
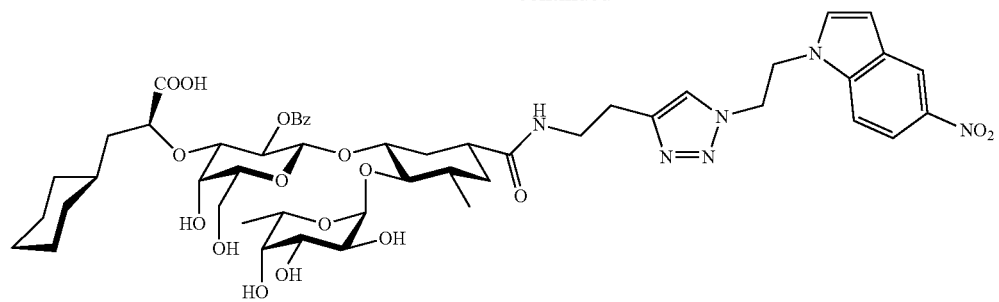
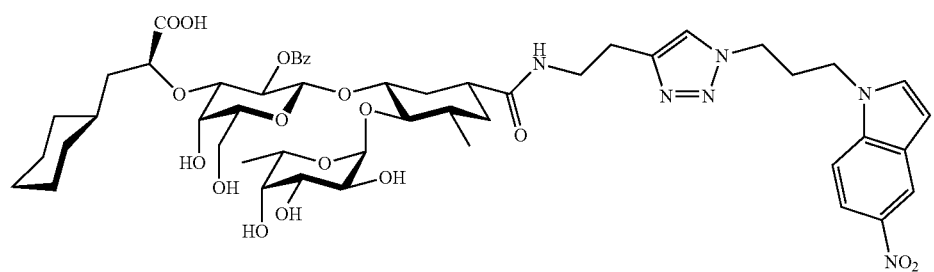
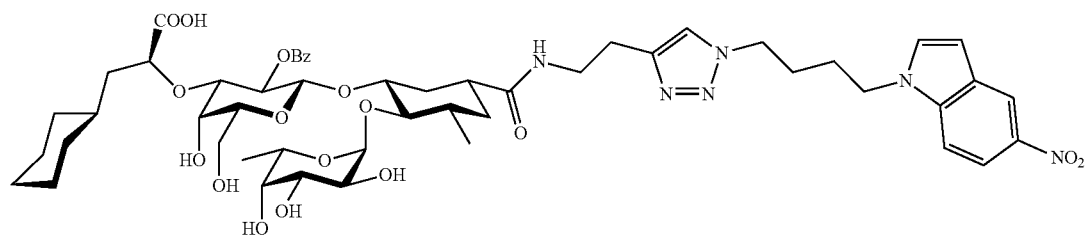
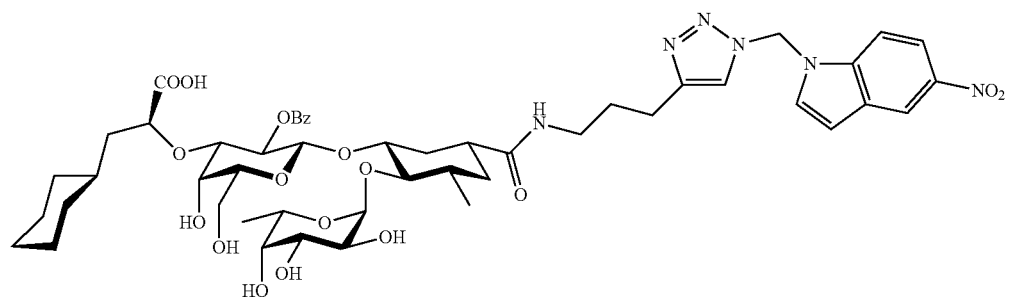
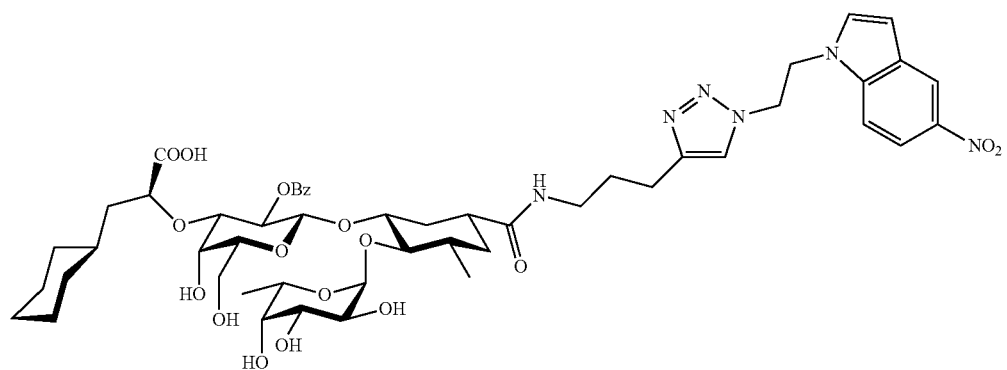

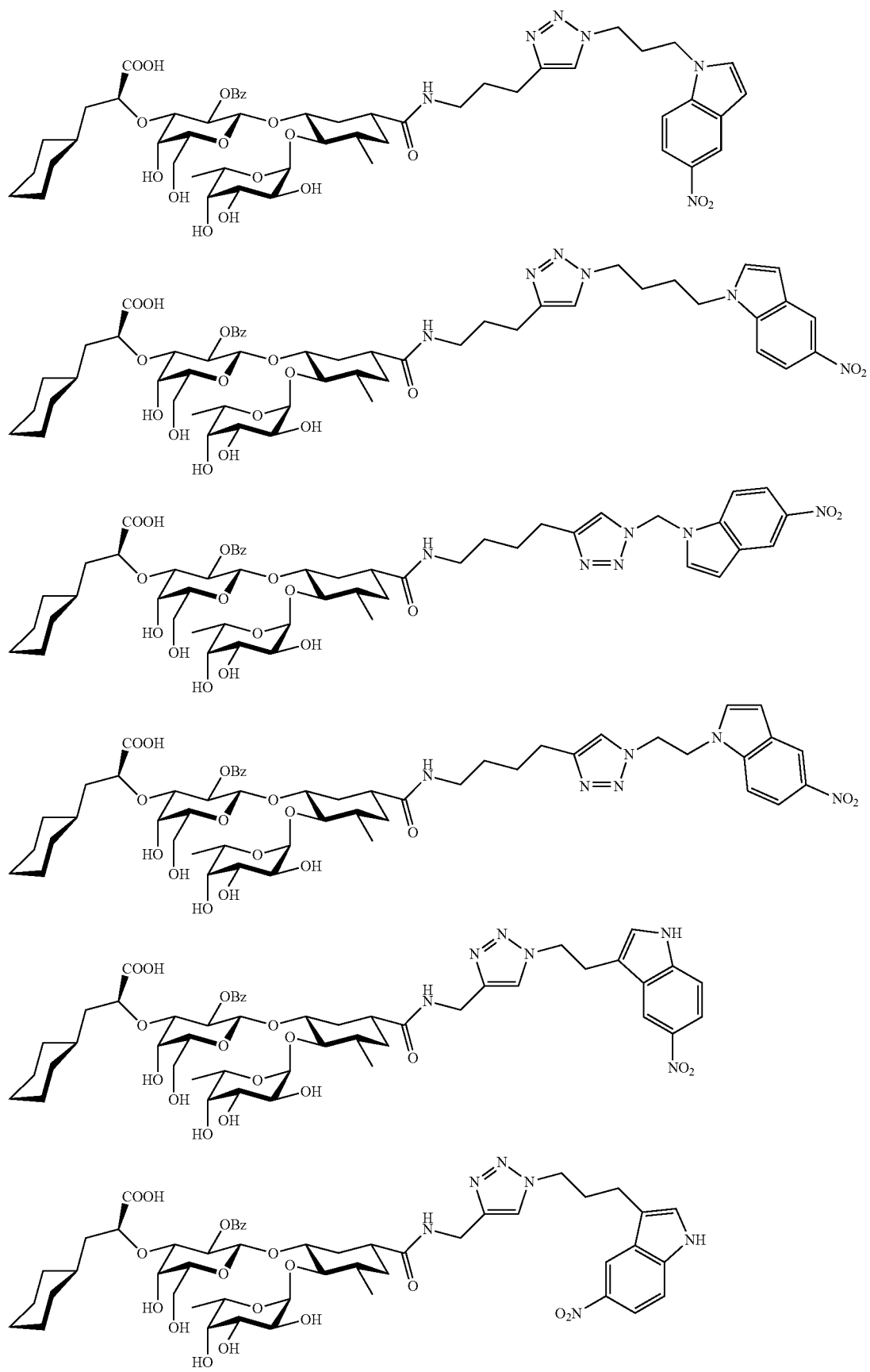

-continued
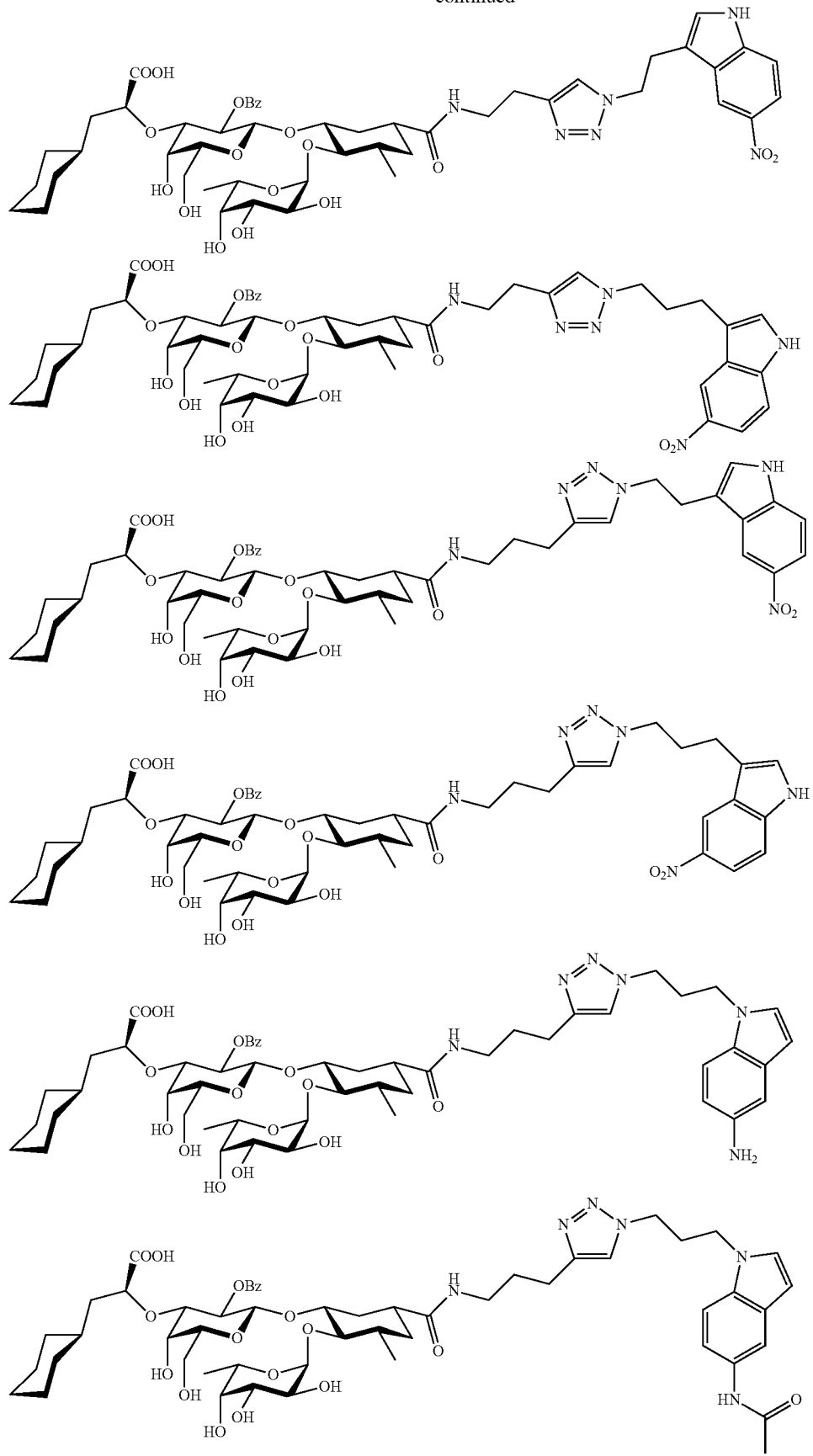

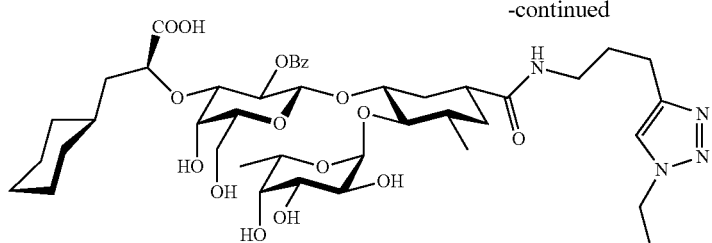

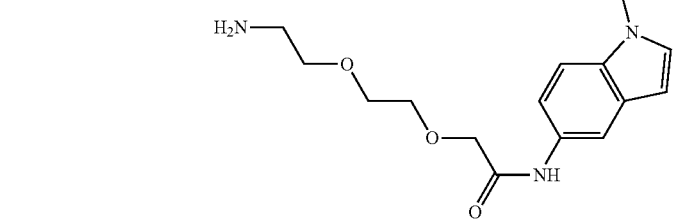

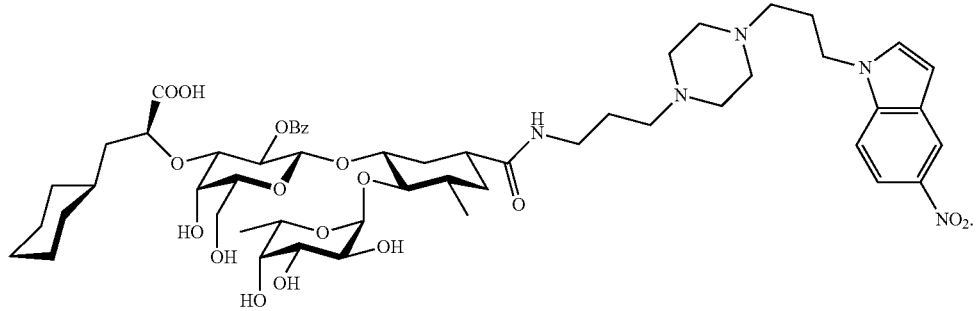

Binding affinities of the compounds are set forth in Table 1 below.

All compounds of the present invention or useful thereto (e.g., for pharmaceutical compositions or methods of treating), include physiologically acceptable salts thereof. Examples of such salts are Na, K, Li, Mg, Ca and Cl.

Compounds as described herein may be present within a pharmaceutical composition. A pharmaceutical composition comprises one or more compounds in combination with (i.e., not covalently bonded to) one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of compound release. The amount of compound contained within a sustained release formulation depends upon the site of implantation, the rate and expected duration of release and the nature of the condition to be treated.

The above described compounds including equivalents thereof are useful in methods of the present invention to treat individuals in need thereof. As used herein, such individuals include humans, as well as non-human warm-blooded animals such as non-human mammals. A preferred individual for treatment is a human. Typically a compound will be administered to an individual as a pharmaceutical composition, i.e., in combination with a pharmaceutically acceptable carrier or diluent.

The above described compounds may be administered in a manner appropriate to the disease to be treated. Appropriate dosages and a suitable duration and frequency of administration may be determined by such factors as the condition of the patient, the type and severity of the patient's disease and the method of administration. In general, an appropriate dosage and treatment regimen provides the compound(s) in an amount sufficient to provide therapeutic and/or prophylactic benefit.

Within particularly preferred embodiments of the invention, a compound may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated, which will be familiar to those of ordinary skill in the art.

In an embodiment, an individual who is in need of treatment of a disease (or complication associated therewith) in which an E-selectin-mediated function is involved is administered at least one (i.e., one or more) of the above described compounds in an amount effective for the treatment.

A variety of conditions are associated with a selectin-mediated function. Such conditions include, for example, tissue transplant rejection, platelet-mediated diseases (e.g., atherosclerosis and clotting), hyperactive coronary circulation, acute leukocyte-mediated lung injury (e.g., adult respiratory distress syndrome (ARDS)), Crohn's disease, inflammatory diseases (e.g., inflammatory bowel disease), autoimmune diseases (MS, myasthenia gravis), infection, cancer (and metastasis), thrombosis, wounds (and wound-associated sepsis), burns, spinal cord damage, digestive tract mucous membrane disorders (gastritis, ulcers), osteoporosis, rheumatoid arthritis, osteoarthritis, asthma, allergy, psoriasis, septic shock, traumatic shock, stroke, nephritis, atopic dermatitis, frostbite injury, adult dyspnoea syndrome, ulcerative colitis, systemic lupus erythematosus, diabetes and reperfusion injury following ischaemic episodes. Compounds may also be administered to a patient prior to heart surgery to enhance recovery. Other uses include pain management, prevention of restinosis associated with vascular stenting, and for undesirable angiogenesis, e.g., associated with cancer.

The term "treatment," as set forth above, refers to any of a variety of positive effects from the treatment including, for example, eradicating a complication associated with the disease, relieving to some extent a complication, slowing or stopping progression of the disease, and prolonging the survival time of the recipient. The treatment may be used in conjunction with one or more other therapies for any of the illnesses (or complications associated therewith) described above.

Compounds as described above are capable, for example, of inhibiting selectin-mediated cell adhesion. This ability may generally be evaluated using any of a variety of in vitro assays designed to measure the effect on adhesion between selectin-expressing cells (e.g., adhesion between leukocytes or tumor cells and platelets or endothelial cells). For example, such cells may be plated under standard conditions that, in the absence of compound, permit cell adhesion. In general, a compound is an inhibitor of selectin-mediated cell adhesion if contact of the test cells with the compound results in a discernible inhibition of cell adhesion. For example, in the presence of compounds (e.g., micromolar levels), disruption of adhesion between leukocytes or tumor cells and platelets or endothelial cells may be determined visually within approximately several minutes, by observing the reduction of cells interacting with one another.

The following Examples are offered by way of illustration and not by way of limitation.

EXAMPLES

Example 1

Figure 3:
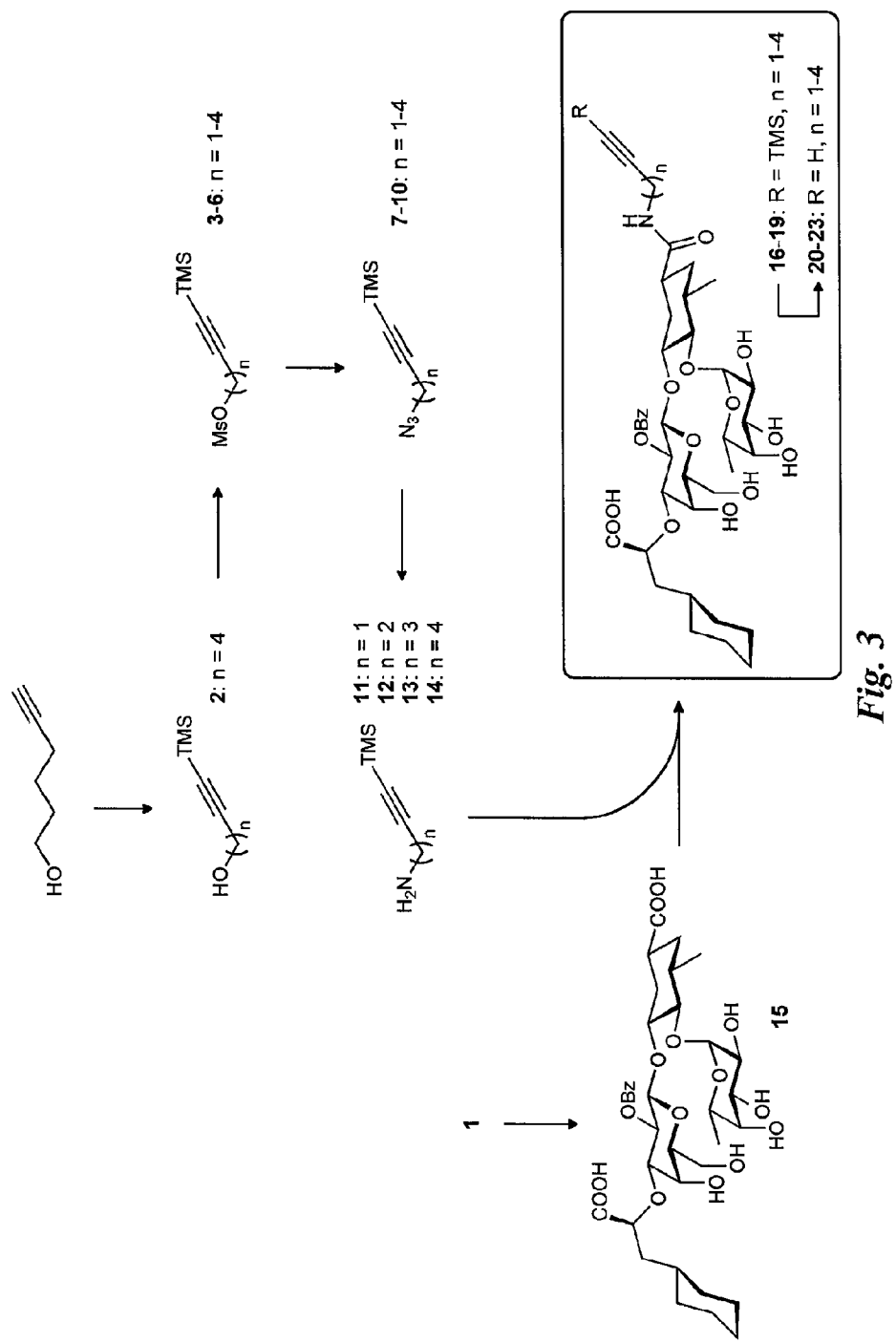
FIG. 3 is a diagram illustrating the synthesis of the alkynyl glycomimetic ligands.

Synthesis of the Alkynyl Glycomimetic Ligands (FIG. 3)

Synthesis of Intermediate 2

6-(Trimethylsilyl)-hex-5-yn-1-ol

Under argon, hex-5-yn-1-ol (1.03 g, 10.5 mmol) was dissolved in anhydrous THF (10 mL) and cooled to −90° C. $^t$BuLi (1.6 M in pentane; 14.4 mL, 23.1 mmol) was added over a period of 10 minutes, which lead to refreezing of the reaction mixture. Gradual warming to −10° C. over 15 min led to liquefaction, and after 2 h of stirring, Me$_3$SiCl (3.0 mL, 23.1 mmol) was added. After 2 h, 1 M aq. HCl (3 mL) was added and stirring was continued for another hour. The reaction mixture was extracted with Et$_2$O (3×40 mL), the combined organic layers were washed with satd. aq. NaHCO$_3$ (20 mL) and brine (20 mL). The dried (Na$_2$SO$_4$) organic phases were concentrated in vacuo, and alcohol 2 was obtained as a colorless oil (2.10 g), which was used without further purification.

Synthesis of Intermediate 3

3-(Trimethylsilyl)prop-2-ynyl methanesulfonate 3-(trimethylsilyl)prop-2-yn-1-ol (1.56 g, 12.2 mmol) was dissolved in anhydrous CH$_2$Cl$_2$ (37 mL) under argon. The solution was cooled to −78° C., followed by addition of Et$_3$N (3.37 mL, 24.3 mmol). MeSO$_2$Cl (0.948 mL, 12.2 mmol) was added to the solution over a period of 10 min, leading to the formation of a white precipitate. After stirring at −78° C. for 30 min, the reaction mixture was washed with 0.5 M aq. HCl (15 mL), satd. aq. NaHCO$_3$ (20 mL), and brine (20 mL). After extraction of the aqueous layers with CH$_2$Cl$_2$ (2×30 mL), the combined organic layers were dried over Na$_2$SO$_4$, and the solvent was removed in vacuo to give the mesylate 3 as a pale yellow liquid (2.46 g) which was used without further purification.

Synthesis of Intermediate 4

4-(Trimethylsilyl)but-3-ynyl methanesulfonate

Following the procedure for 3, MeSO$_2$Cl (2.05 mL, 26.3 mmol) was added to a solution of 4-(trimethylsilyl)but-3-yn-1-ol (3.12 g, 21.9 mmol) and Et$_3$N (6.07 mL, 43.8 mmol) in anhydrous CH$_2$Cl$_2$ (65 mL) at −15° C. After 1.5 h, the reaction mixture was worked up, and the mesylate 4 was obtained as a pale yellow oil (4.88 g), which was used without further purification.

Synthesis of Intermediate 5

5-(Trimethylsilyl)pent-4-ynyl methanesulfonate

Following the procedure for 3, MeSO$_2$Cl (1.37 mL, 17.6 mmol) was added to a solution of 5-(trimethylsilyl)pent-4-yn-1-ol (2.29 g, 14.7 mmol) and Et$_3$N (4.07 mL, 29.4 mmol) in anhydrous CH$_2$Cl$_2$ (50 mL) at −15° C. After 2 h, the reaction mixture was worked up, and the mesylate 5 was obtained as a pale yellow oil (3.56 g), which was used without further purification.

Synthesis of Intermediate 6

6-(Trimethylsilyl)hex-5-ynyl methanesulfonate

MeSO$_2$Cl (0.98 mL, 12.6 mmol) was added to a solution of 2 (2.10 g) and Et$_3$N (2.9 mL, 21.0 mmol) in anhydrous CH$_2$Cl$_2$ (35 mL) at −15° C. The reaction mixture was allowed to warm to r.t., and after 1.5 h, it was washed with 0.5 M aq. HCl (10 mL), satd. aq. NaHCO$_3$ (15 mL), and brine (15 mL). After extraction of the aqueous layers with CH$_2$Cl$_2$ (2×30 mL), the combined organic layers were dried over Na$_2$SO$_4$, and the solvent was removed in vacuo. The residue was purified by silica gel chromatography (petrol ether/$CH_2Cl_2$ linear gradient) to afford mesylate 6 as a colorless liquid (2.26 g).

Synthesis of Intermediate 7

(3-Azidoprop-1-ynyl)trimethylsilane

Mesylate 3 (2.46 g, 11.9 mmol) was dissolved in anhydrous DMF (50 mL) under argon. $NaN_3$ (0.87 g, 13.4 mmol) was added, and the suspension was heated to 65° C. After vigorous stirring of the viscous reaction mixture for 35 min, water (30 mL) was added, and the suspension was filtered through a plug of celite. The celite was washed with diethyl ether (80 mL). The water-DMF mixture was extracted with $Et_2O$ (3×60 mL), and the organic layers were thoroughly washed with water (2×40 mL) and brine (40 mL). The combined organic layers were dried over $Na_2SO_4$, the solvent was removed in vacuo, and azide 7 was obtained as a yellow liquid (1.82 g), which was used without further purification.

Synthesis of Intermediate 8

(4-Azidobut-1-ynyl)trimethylsilane

Following the procedure for 7, mesylate 4 (4.88 g, 22.1 mmol) was reacted with $NaN_3$ (1.57 g, 24.1 mmol) in anhydrous DMF (55 mL). After 3 h, the reaction was filtered and worked up to give azide 8 as a yellow liquid (3.35 g), which was used without further purification.

Synthesis of Intermediate 9

(5-Azidopent-1-ynyl)trimethylsilane

Following the procedure for 7, mesylate 5 (3.56 g, 15.2 mmol) was reacted with $NaN_3$ (1.10 g, 16.9 mmol) in anhydrous DMF (35 mL). After 2.5 h, the reaction was filtered and worked up to give azide 9 as a yellow liquid (2.62 g), which was used without further purification.

Synthesis of Intermediate 10

(5-Azidohex-1-ynyl)trimethylsilane

Following the procedure for 7, mesylate 6 (2.26 g, 9.10 mmol) was reacted with $NaN_3$ (716 mg, 11.0 mmol) in anhydrous DMF (20 mL). After 1 h, the reaction was filtered and worked up to afford azide 10 as a yellow liquid (1.41 g), which was used without further purification.

$^1$H NMR (500 MHz, $CDCl_3$): δ 0.12 (s, 9H, $Me_3Si$), 1.57-1.66 (m, 2H, H-3), 1.81-1.89 (m, 2H, H-2), 2.99 (s, 3H, $MeSO_2$), 4.24 (t, J=6.4 Hz, 2H, H-1); $^{13}$C NMR (125 MHz, $CDCl_3$): δ 0.18 ($Me_3Si$), 19.32 (C-4), 24.49 (C-3), 28.22 (C-2), 37.49 ($MeSO_2$), 69.59 (C-1), 85.52 (C-6), 106.19 (C-5).

Synthesis of Intermediate 11

3-(Trimethylsilyl)-prop-2-yn-1-amine

To a solution of azide 7 (1.82 g, 11.9 mmol) in THF (50 mL) and water (1 mL) was added $PPh_3$ (3.18 g, 12.2 mmol). The solution was stirred at 50° C. for 2 h. After careful removal of the solvent in vacuo (≥200 mbar), the reaction mixture was subjected to vacuum distillation (oil bath temperature: 100° C.; approx. 5 mbar; additional cooling trap with liquid nitrogen) to give amine 11 as a colorless liquid (1.29 g, 83% over 3 steps).

$^1$H-NMR (500 MHz, $CDCl_3$): δ 0.11 (s, 9H, TMS-H), 1.37 (s, 2H, $NH_2$), 3.38 (s, 2H, H-1). $^{13}$C-NMR (125 MHz, $CDCl_3$): δ 0.09 (3C, TMS-C), 32.51 (C-1), 86.72 (C-2), 107.41 (C-3); IR (film on NaCl): ν=3375 (s, $NH_2$), 3295 (s, $NH_2$), 3181 (m, $NH_2$), 2960 (vs), 2900 (s), 2850 (m), 2167 (vs, C≡C), 1599 (w, $NH_2$), 1409 (w), 1379 (w), 1332 (s), 1251 (s, $SiCH_3$), 1074 (m), 998 (s), 955 (m), 908 (m), 842 (m, $Me_3Si$), 760 (m, $Me_3Si$), 734 (m), 699 (m), 642 (m), 584 (m) cm$^{-1}$.

The NMR spectral data were in accordance with previously published values [I. MacInnes, J. C. Walton, *J. Chem. Soc., Perkin Trans.* 2 1987, 8, 1077-1082].

Synthesis of Intermediate 12

4-(Trimethylsilyl)-but-3-yn-1-amine

To a solution of azide 8 (3.35 g, 20.0 mmol) in THF (90 mL) and water (1.8 mL) was added $PPh_3$ (5.76 g, 21.9 mmol). The solution was stirred at 50° C. for 1.5 h. After removal of the solvent in vacuo, the reaction mixture was subjected to vacuum distillation (oil bath temperature: 120° C.; approx. 0.1 mbar; additional cooling trap with liquid nitrogen) to give the amine 12 as a colorless liquid (2.49 g, 80% over 3 steps).

$^1$H NMR (500 MHz, $CDCl_3$): δ 0.12 (s, 9H, $Me_3Si$), 1.40 (s, 2H, $NH_2$), 2.34 (t, 2H, H-1), 2.80 (t, 2H, H-2); $^{13}$C NMR (125 MHz, $CDCl_3$): δ 0.23 ($Me_3Si$), 25.08 (C-2), 41.09 (C-1), 86.29 (C-3), 105.09 (C-4). IR (film on NaCl): ν3373 (m, $NH_2$), 3297 (m, $NH_2$), 2959 (vs), 2896 (s,), 2868 (s, C—H), 2174 (vs, C≡C), 1678 (m, $NH_2$), 1621 (w), 1455 (m), 1425 (m), 1409 (m), 1383 (m), 1355 (m), 1250 (vs, $SiCH_3$), 1179 (vw), 1157 (vw), 1119 (vw), 1085 (w), 1034 (s), 979 (m), 908 (s), 844 (vs, $Me_3Si$), 760 (vs, $Me_3Si$), 734 (vs), 699 (m), 639 (s), 574 (m) cm$^{-1}$.

The $^1$H NMR spectral data were in accordance with previously published values [M. Pullagurla, M. Dukat, B. L. Roth, V. Setola, B. A. Glennon, *Med. Chem. Res.* 2005, 14, 1-18.].

Synthesis of Intermediate 13

5-(Trimethylsilyl)-pent-4-yn-1-amine

To a solution of azide 9 (1.30 g, 7.17 mmol) in THF (100 mL) and water (1 mL) was added $PPh_3$ (2.24 g, 8.5 mmol). The solution was stirred at 50° C. for 4.5 h. After removal of the solvent in vacuo, the reaction mixture was subjected to vacuum distillation (oil bath temperature: 120° C.; approx. 0.1 mbar) to give amine 13 as a colorless oil (0.973 g, 43% over 3 steps).

$^1$H NMR (500 MHz, $CDCl_3$): δ 0.12 (s, 9H, $Me_3Si$), 1.18 (s, 2H, $NH_2$), 1.62 (p, 2H, H-2), 2.27 (t, J=7.0 Hz, 2H, H-3), 2.77 (t, J=6.9 Hz, 2H, H-1); $^{13}$C NMR (125 MHz, $CDCl_3$): δ 0.23 ($Me_3Si$), 17.42 (C-3), 32.42 (C-2), 41.34 (C-1), 84.95 (C-4), 106.92 (C-5). IR (film on NaCl): ν3376 (m, $NH_2$), 3297 (w, $NH_2$), 3181 (w, $NH_2$), 2955 (vs), 2861 (vs), 2173 (vs, C≡C), 1682 (w), 1602 (w, $NH_2$), 1431 (s), 1408 (m), 1324 (m), 1250 (vs, $Me_3Si$), 1087 (s), 1000 (m), 914 (s), 843 (vs, $Me_3Si$), 760 (vs, $Me_3Si$), 734 (vs), 698 (s), 640 (s), 579 (w) cm$^{-1}$.

The spectral data were in accordance with previously published values [Y. W. Li, T. J. Marks, *J. Am. Chem. Soc.* 1996, 118, 9295-9306.], [Y. Li, P.-F. Fu, T. J. Marks, *Organometallics* 1994, 13, 439-440.]

Synthesis of Intermediate 14

6-(Trimethylsilyl)-hex-5-yn-1-amine

To a solution of azide 10 (1.41 g, 7.22 mmol) in THF (100 mL) and water (1 mL) was added PPh$_3$ (2.27 g, 8.65 mmol). The solution was stirred at 50 to 60° C. for 4.5 h. After removal of the solvent in vacuo, the reaction mixture was subjected to vacuum distillation (oil bath temperature: 120° C.; approx. 0.1 mbar) to give the amine 14 as a colorless oil (1.10 g, 62% over 4 steps).

$^1$H NMR (500 MHz, CDCl$_3$): δ 0.43 (s, 9H, Me$_3$Si), 1.39 (s, 2H, NH$_2$), 1.82-1.87 (m, 4H, H-2, H-3), 2.53 (t, J=6.6 Hz, 2H, H-4), 2.98-3.03 (m, 2H, H-1); $^{13}$C NMR (125 MHz, CDCl$_3$): δ 0.06 (Me$_3$Si), 19.62 (C-4), 25.89 (C-3), 32.87 (C-2), 41.65 (C-1), 84.89 (C-6), 107.12 (C-5). IR: ν3371 (s, NH$_2$), 3296 (s, NH$_2$), 3181 (m, NH$_2$), 2957 (vs), 2929 (vs), 2901 (vs), 2860 (vs), 2173 (vs, C≡C), 1596 (m, NH$_2$), 1455 (m), 1431 (m), 1408 (m), 1364 (w), 1326 (m), 1249 (vs, Me$_3$Si), 1051 (m), 1027 (m), 998 (w), 937 (m), 842 (vs, Me$_3$Si), 760 (vs, Me$_3$Si), 698 (s), 639 (s), 619 (vw), 461 (s) cm$^{-1}$.

Synthesis of Intermediate 15

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-cyclohexanecarboxylic acid Ester 1 (268 mg, 0.355 mmol) was dissolved in a 1 M solution of NaOH in H$_2$O/MeOH 1:1 (8 mL) and stirred at r.t. for 3 h. The reaction was stopped by addition of 0.5 M aq. HCl (1.6 mL), and the solvent was removed in vacuo. The residue was purified using preparative HPLC-MS (H$_2$O/MeCN+0.2% HCOOH) yielding diacid 15 as a white powder (207 mg, 79%). The starting material was partially recovered (25 mg, 9%).

$^1$H-NMR (500 MHz, MeOD): δ 0.50-0.75 (m, 4H, Cy), 0.86-0.97 (m, 1H, Cy), 1.11 (d, J=6.4 Hz, 3H, Me), 1.06-1.16 (m, 2H, H-6$_a$, H-2$_a$), 1.33 (d, J=6.5 Hz, 3H, Fuc H-6), 1.19-1.38 (m, 5H, 5Cy), 1.38-1.47 (m, 1H, Lac H-3$_a$), 1.47-1.56 (m, 1H, Lac H-3$_b$), 1.56-1.72 (m, 2H, Cy, H-5), 1.78 (d, J=12.8 Hz, 1H, H-6), 2.29-2.40 (m, 2H, H-2, H-1), 3.11 (t, J=9.5 Hz, 1H, H-4), 3.58 (t, J=5.6 Hz, 1H, Gal H-5), 3.64-3.80 (m, 6H, Gal H-3, H-3, Fuc H-2, 2Gal H-6, Fuc H-4), 3.85 (dd, J=3.0, 10.3 Hz, 1H, Fuc H-3), 3.96 (s, 1H, Gal H-4), 4.03-4.08 (m, 1H, Lac H-2), 4.71 (d, J=8.1 Hz, 1H, Gal H-1), 4.93-4.97 (m, 1H, Fuc H-1), 4.99 (dd, J=6.1, 12.6 Hz, 1H, Fuc H-5), 5.44 (t, J=8.8 Hz, 1H, Gal H-2), 7.46-7.52 (m, 2H, C$_6$H$_5$), 7.58-7.64 (m, 1H, C$_6$H$_5$), 8.04-8.11 (m, 2H, C$_6$H$_5$); $^{13}$C-NMR (125 MHz, MeOD): δ 16.70 (Fuc C-6), 19.20 (Me), 26.53 (Cy), 26.72 (Cy), 27.28 (Cy), 33.08 (Cy), 34.17 (Cy), 35.05, 35.08 (2C, Cy, C-2), 37.10 (C-6), 39.20 (C-5), 41.38 (C-1), 42.78 (Lac C—), 62.68 (Gal C-6), 67.70, 67.75 (2C, Gal C-4, Fuc C-5), 70.32 (Fuc C-2), 71.44 (Fuc C-3), 73.01 (Gal C-2), 73.97 (Fuc C-4), 75.89 (Gal C-5), 77.91 (Lac C-2), 79.95 (C-3), 83.16 (C-4), 83.67 (Gal C-3), 100.49 (Fuc C-1), 100.61 (Gal C-1), 129.68 (C$_6$H$_5$), 130.92 (C$_6$H$_5$), 131.53 (C$_6$H$_5$), 134.35 (C$_6$H$_5$), 166.94 (O(C=O)Ph), 177.88 (cHex COOH), 178.89 (Lac COOH); elemental analysis calcd (%) for C$_{36}$H$_{52}$O$_{16}$·H$_2$O (758.80): C, 56.98; H, 7.14. found: C, 57.09/57.08; H, 6.93/6.97. [a]$_D^{20}$=−67.2 (c=0.40, MeOH); IR (KBr): ν=3433 (vs, OH), 2927 (s), 2854 (m) 1720 (vs, C=O), 1638 (m), 1450 (m), 1339 (m), 1316 (m), 1272 (vs), 1207 (m), 1167 (m), 1111 (vs), 1079 (vs), 999 (m), 967 (w), 846 (w), 806 (vw), 771 (vw) 712 (s), 677 (w), 628 (w), 559 (w) cm$^1$.

General Procedure I for the Synthesis of Intermediates 16-19

The carboxyl group attached to the cyclohexanediole ring (cHex COOH) in 15 can selectively be converted into an active ester using HBTU/HOBt in presence of the lactic acid carboxyl group (Lac COOH). This finding was exploited for the attachment of the alkyne linker to the cyclohexanediole ring as described below.

Dicarboxylic acid 15 (1 equiv.) and HOBt (3 equiv.) were dissolved in anhydrous DMF (approx. 0.025 M) under argon. HBTU (1.1-1.2 equiv.) was added and the solution was stirred at r.t. for 5 min. An excess of alkyne amine (approx. 10% v/v) was added, and stirring was continued until no further consumption of starting material was observed in MS (after 1.5 to 3 h). The solvent was removed in vacuo, and the residue was purified by preparative HPLC-MS (H$_2$O/MeCN+0.2% HCOOH), and the desired monoamide was isolated based on its retention time (t$_{R(cHex\ amide)}$>t$_{R(Lac\ amide)}$). The identity of the amide was verified by 2D HMBC spectra (coupling of linker and cyclohexyl protons to the amide C=O).

General Procedure II for the Synthesis of Products 20-23

To an approx. 0.03 mm solution of TMS-protected alkyne amide (1 equiv.) in anhydrous THF, TBAF (2 equiv.; 1 M solution in THF) was added at r.t. under argon. The solution was stirred for 1 to 2 h, and the solvent was removed in vacuo. The residue was purified by RP-18 chromatography (water/MeOH) or preparative HPLC-MS (H$_2$O/MeCN+0.2% HCOOH).

Synthesis of Intermediate 16

(1R,3R,4R,5 S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-[3-(trimethylsilyl)prop-2-yn-1-yl] cyclohexanecarboxamide Following general procedure I, dicarboxylic acid 15 (100 mg, 0.135 mmol), HOBt (55.2 mg, 0.408 mmol), HBTU (53.6 mg, 0.141 mmol) and alkyne amine 11 (500 μL) were stirred at r.t. for 3 h to afford the desired monoamide 16 as a white solid (41 mg, 35%). The starting material (1S) was partially recovered (28 mg, 28%).

$^1$H-NMR (500 MHz, MeOD): δ 0.15 (s, 9H, TMS-H), 0.52-0.75 (m, 4H, Cy), 0.91 (d, J=12.6 Hz, 1H, Cy), 1.10 (d, J=6.3 Hz, 3H, Me), 1.14-1.39 (m, 10H, H-2$_a$, H-6$_a$, 5Cy, Fuc H-6), 1.39-1.47 (m, 1H, Lac H-3$_a$), 1.47-1.55 (m, 1H, Lac H-3$_b$), 1.55-1.71 (m, 3H, Cy, H-6$_b$, H-5), 2.12-2.18 (m, 1H, H-2$_b$), 2.27 (s, 1H, H-1), 3.14 (t, J=9.5 Hz, 1H, H-4), 3.57 (t, J=5.7 Hz, 1H, Gal H-5), 3.62-3.81 (m, 6H, Gal H-3, H-3, Fuc H-2, Fuc H-4, Gal H-6), 3.83-3.90 (m, 2H, Fuc H-3, H-1'$_a$), 3.92-3.99 (m, 2H, Gal H-4, H-1'$_b$), 4.04 (dd, J=2.7, 9.5 Hz, 1H, Lac H-2), 4.69 (d, J=8.0 Hz, 1H, Gal H-1), 4.94-5.00 (m, 2H, Fuc H-1, Fuc H-5), 5.43 (t, J=8.8 Hz, 1H, Gal H-2), 7.48-7.54 (m, 2H, C$_6$H$_5$), 7.59-7.64 (m, 1H, C$_6$H$_5$), 8.03-8.08 (m, 2H, C$_6$H$_5$). $^{13}$C-NMR (125 MHz, MeOD): δ −0.07 (Me$_3$Si), 16.69 (Fuc C-6), 19.22 (Me), 26.55 (Cy), 26.68 (Cy), 27.24 (Cy), 30.37 (C-1'), 33.12 (Cy), 34.17 (Cy), 35.02 (Cy), 35.31 (C-2), 37.25 (C-6), 39.25 (C-5), 42.73 (Lac C-3), 42.87 (C-1), 62.71 (Gal C-6), 67.68, 67.77 (2C, Fuc C-5, Gal C-4), 70.30 (Fuc C-2), 71.43 (Fuc C-3), 72.99 (Gal C-2), 73.94 (Fuc C-4), 75.94 (Gal 5-C), 77.99 (Lac C-2), 79.89 (C-3), 83.02 (C-4), 83.68 (Gal C-3), 87.81 (C-3'), 100.41 (Fuc C-1), 100.54 (Gal C-1), 103.04 (C-2'), 129.74 (C$_6$H$_5$), 130.87 (C$_6$H$_5$), 131.53 (C$_6$H$_5$), 134.34 (C$_6$H$_5$), 166.84 (O(C=O)

Ph), 176.41 (CONH), 178.81 (COOH); MS: m/z calcd. for $C_{42}H_{63}NO_{15}Si$ [M−H]$^-$: 848.39. found: 848.54.

Synthesis of Intermediate 17

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-[4-(trimethylsilyl)but-3-yn-1-yl]cyclohexanecarboxamide Following general procedure I, dicarboxylic acid 15 (31.7 mg, 0.0428 mmol), HOBt (17.7 mg, 0.135 mmol), HBTU (19.1 mg, 0.0504 mmol) and alkyne amine 12 (200 µL) were stirred at r.t. for 1.5 h to afford the desired monoamide 17 as a white solid (30 mg, 70%). The starting material (1S) was partially recovered (6.5 mg, 18%).

$^1$H NMR (500 MHz, MeOD): δ 0.15 (s, 9H, TMS-H), 0.52-0.73 (m, 4H, Cy), 0.91 (d, J=12.1 Hz, 1H, Cy), 1.11 (d, J=6.4 Hz, 3H, Me), 1.14-1.38 (m, 10H, H-2$_a$, H-6$_a$, 5Cy, Fuc H-6), 1.38-1.46 (m, 1H, Lac H-3$_a$), 1.47-1.71 (m, 4H, Lac H-3$_b$, Cy, H-6$_b$, H-5), 2.09-2.16 (m, 1H, H-2$_b$), 2.23-2.30 (m, 1H, H-1), 2.32-2.38 (m, 2H, H-2'), 3.11-3.20 (m, 2H, H-4, H-1'$_a$), 3.20-3.28 (m, 1H, H-1'$_b$), 3.55 (t, J=5.8 Hz, 1H, Gal H-5), 3.63 (dd, J=2.8, 9.7 Hz, 1H, Gal H-3), 3.66-3.81 (m, 5H, H-3, Fuc H-2, Fuc H-4, Gal H-6), 3.86 (dd, J=3.2, 10.3 Hz, 1H, Fuc H-3), 3.97 (d, J=2.1 Hz, 1H, Gal H-4), 4.05 (dd, J=2.6, 9.7 Hz, 1H, Lac H-2), 4.67 (d, J=8.1 Hz, 1H, Gal H-1), 4.97-5.02 (m, 2H, Fuc H-1, Fuc H-5), 5.44 (dd, J=8.5, 9.3 Hz, 1H, Gal H-2), 7.48-7.53 (m, 2H, $C_6H_5$), 7.60-7.65 (m, 1H, $C_6H_5$), 7.94 (t, J=5.8 Hz, 1H, CONH), 8.04-8.09 (m, 2H, $C_6H_5$). $^{13}$C NMR (125 MHz, MeOD): δ 0.30 (Me$_3$Si), 16.70 (Fuc C-6), 19.26 (Me), 21.02 (C-2'), 26.53 (Cy), 26.68 (Cy), 27.23 (Cy), 33.07 (Cy), 34.14 (Cy), 35.02 (Cy), 35.51 (C-2), 37.33 (C-6), 39.24 (C-5), 39.29 (C-1'), 42.72 (Lac C-3), 43.11 (C-1), 62.69 (Gal C-6), 67.66, 67.73 (2C, Gal C-4, Fuc C-5), 70.26 (Fuc C-2), 71.38 (Fuc C-3), 72.94 (Gal C-2), 73.93 (Fuc C-4), 75.94 (Gal C-5), 77.93 (Lac C-2), 79.86 (C-3), 82.96 (C-4), 83.62 (Gal C-3), 86.23 (C-4'), 100.41 (Fuc C-1), 100.56 (Gal C-1), 105.35 (C-3'), 129.73 ($C_6H_5$), 130.87 ($C_6H_5$), 131.48 ($C_6H_5$), 134.37 ($C_6H_5$), 166.78 (O(C=O)Ph), 177.06 (CONH), 178.71 (COOH); MS: m/z: calcd. for $C_{43}H_{65}NO_{15}Si$ [M−H]$^-$: 862.41. found: 862.38.

Synthesis of Intermediate 18

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-[5-(trimethylsilyl)pent-4-yn-1-yl]cyclohexanecarboxamide Following general procedure I, dicarboxylic acid 15 (120 mg, 0.159 mmol), HOBt (67 mg, 0.496 mmol), HBTU (74 mg, 0.195 mmol) and alkyne amine 13 (520 µL) were stirred at r.t. for 2 h to afford the desired monoamide 18 as a white solid (57 mg, 40%). The starting material (1S) was partially recovered (23 mg, 19%).

$^1$H-NMR (500 MHz, MeOD): δ 0.13 (s, 9H, TMS-H), 0.51-0.62 (m, 1H, Cy), 0.62-0.73 (m, 3H, Cy), 0.85-0.96 (m, 1H, Cy), 1.11 (d, J=6.5 Hz, 3H, Me), 1.15-1.38 (m, 10H, H-2$_a$, H-6$_a$, 5Cy, Fuc H-6), 1.37-1.44 (m, 1H, Lac H-3$_a$), 1.47-1.55 (m, 1H, Lac H-3$_b$), 1.55-1.69 (m, 6H, Cy, H-6$_b$, H-5, H-3', H-1), 2.12 (d, J=11.1 Hz, 1H, H-2), 2.22 (t, J=7.2 Hz, 3H, H-3', H-1), 3.10-3.24 (m, 3H, H-1', H-4), 3.56 (t, J=5.7 Hz, 1H, Gal H-5), 3.62 (dd, J=2.9, 9.7 Hz, 1H, Gal H-3), 3.65-3.81 (m, 5H, H-3, Fuc H-2, Fuc H-4, Gal H-6), 3.87 (dd, J=3.3, 10.3 Hz, 1H, Fuc H-3), 3.96 (d, J=7.1 Hz, 2H, Lac H-2, Gal H-4), 4.68 (d, J=8.1 Hz, 1H, Gal H-1), 4.95-5.02 (m, 2H, Fuc H-1, Fuc H-5), 5.43 (dd, J=8.3, 9.4 Hz, 1H, Gal H-2), 7.48-7.53 (m, 2H, $C_6H_5$), 7.59-7.64 (m, 1H, $C_6H_5$), 7.77 (t, J=5.6 Hz, 1H, CONH), 8.04-8.08 (m, 2H, $C_6H_5$); $^{13}$C-NMR (125 MHz, MeOD): δ 0.23 (TMS-C), 16.72 (Fuc C-6), 18.03 (C-2'), 19.22 (Me), 26.56 (Cy), 26.70 (Cy), 27.26 (Cy), 29.64 (C-3'), 33.09 (Cy), 34.15 (Cy), 35.06 (Cy), v (C-2), 37.35 (C-6), 39.33 (C-5), 39.43 (C-1'), 42.76 (Lac C-3), 43.34 (C-1), 62.70 (Gal C-6), 67.69, 67.72 (Gal H-4, Fuc H-5), 70.28 (Fuc C-2), 71.40 (Fuc C-3), 72.96 (Gal C-2), 73.97 (Fuc C-4), 75.93 (Gal 5-C), 77.77 (Lac C-2), 79.90 (C-3), 83.01 (C-4), 83.67 (Gal C-3), 85.42 (C-5'), 100.49 (Fuc C-1), 100.56 (Gal C-1), 107.62 (C-4'), 129.79 ($C_6H_5$), 130.87 ($C_6H_5$), 131.56 ($C_6H_5$), 134.41 ($C_6H_5$), 166.77 (O(C=O)Ph), 177.12 (CONH), 178.75 (COOH); MS: calcd for $C_{44}H_{67}NO_{15}Si$ [M−H]$^-$: 876.42. found: 862.63. [a]$_D^{20}$=−61.5 (c=0.79, MeOH); IR (KBr): ν=3430 (vs, OH), 2927 (s), 2854 (m), 2175 (vw), 1726 (s, C=O), 1650 (m, C=O), 1542 (vw), 1535 (vw), 1450 (w), 1369 (w), 1338 (w), 1315 (w), 1271 (s), 1250 (m), 1166 (w), 1140 (vs), 1079 (vs) 1036 (s), 1001 (w), 969 (vw), 844 (m, Me$_3$Si), 760 (vw), 709 (w) cm$^{-1}$.

Synthesis of Intermediate 19

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-[6-(trimethylsilyl)hex-5-yn-1-yl]cyclohexanecarboxamide Following general procedure I, dicarboxylic acid 15 (47 mg, 0.0634 mmol), HOBt (26 mg, 0.192 mmol), HBTU (29 mg, 0.0765 mmol) and alkyne amine 14 (200 µL) were stirred at r.t. for 2 h to afford the desired monoamide 19 as a white solid (25 mg, 44%). The starting material (1S) was partially recovered (5.5 mg, 12%).

$^1$H-NMR (500 MHz, MeOD): δ 0.12 (s, 9H, TMS-H), 0.51-0.75 (m, 4H, Cy), 0.86-0.96 (m, 1H, Cy), 1.11 (d, J=6.4 Hz, 3H, Me), 1.15-1.28 (m, 3H, H-6$_a$, H-2$_a$, Cy), 1.27-1.38 (m, 7H, Fuc H-6, Cy), 1.38-1.45 (m, 1H, Lac H3$_a$), 1.45-1.62 (m, 7H, Lac H3$_b$, H-3', H-2', H-6$_b$, Cy), 1.62-1.71 (m, 1H, H-5), 2.08-2.14 (m, 1H, H-2$_b$), 2.21-2.28 (m, 3H, H-4', H-1), 3.08-3.12 (m, 2H, H-1'), 3.15 (t, J=9.6 Hz, 1H, H-4), 3.56 (t, J=5.9 Hz, 1H, Gal H-5), 3.65 (dd, J=2.7, 9.8 Hz, 1H, Gal H-3), 3.67-3.81 (m, 5H, H-3, Fuc H-2, Gal H-6), 3.86 (dd, J=3.2, 10.3 Hz, 1H, Fuc H-3), 3.96 (d, J=2.3 Hz, 1H, Gal H-4), 4.06 (dd, J=2.7, 9.7 Hz, 1H, Lac H-2), 4.69 (d, J=8.0 Hz, 1H, Gal H-1), 4.95-5.01 (m, 2H, Fuc H-1, Fuc H-5), 5.43 (t, J=8.9 Hz, 1H, Gal H-2), 7.48-7.53 (m, 2H, $C_6H_5$), 7.60-7.65 (m, 1H, $C_6H_5$), 7.77 (t, J=5.6 Hz, 1H, CONH), 8.05-8.08 (m, 2H, $C_6H_5$); $^{13}$C-NMR (125 MHz, MeOD): δ 0.28 (TMS-C), 16.71 (Fuc C-6), 19.25 (Me), 20.07 (C-4'), 26.53 (Cy), 26.68 (Cy), 26.96 (C3'), 27.24 (Cy), 29.54 (C-2'), 33.11 (Cy), 34.15 (Cy), 35.02 (Cy), 35.36 (C-2), 37.51 (C-6), 39.33 (C-5), 39.70 (C-1'), 42.72 (Lac C-3), 43.31 (C-1), 62.71 (Gal C-6), 67.69 (Gal C-4), 67.74 (Fuc C-5), 70.27 (Fuc C-2), 71.39 (Fuc C-3), 72.99 (Gal C-2), 73.95 (Fuc C-4), 75.92 (Gal C-5), 77.85 (Lac C-2), 79.84 (C-3), 83.00 (C-4), 83.63 (Gal C-3), 85.22 (C-6'), 100.44 (Fuc C-1), 100.52 (Gal C-1), 108.17 (C-5'), 129.76 ($C_6H_5$), 130.85 ($C_6H_5$), 131.53 ($C_6H_5$), 134.40 ($C_6H_5$), 166.78 (O(C=O)Ph), 176.96 (CONH), 178.72 (COOH).

Synthesis of Product 20

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(prop-2-yn-1-yl)cyclohexanecarboxamide Following general procedure II, 16 (49 mg, 0.0576 mmol) was reacted with TBAF (115 μL, 0.115 mmol) in 2 mL anhydrous THF. After purification with preparative HPLC-MS, 36 mg (80%) of 20 was obtained as a white solid.

$^1$H-NMR (500 MHz, MeOD): δ 0.52-0.75 (m, 4H, Cy), 0.85-0.97 (m, 1H, Cy), 1.11 (d, J=6.4 Hz, 3H, Me), 1.14-1.27 (4 Cy, H-6$_a$, H-2$_a$), 1.27-1.38 (m, 4H, Cy), 1.34 (d, J=6.5 Hz, 3H, Fuc H-6a), 1.38-1.46 (m, 1H, Lac H-3$_a$), 1.51 (ddd, J=3.9, 10.1, 13.7 Hz, 1H, Lac H-3$_b$), 1.54-1.71 (m, 3H, H-6$_b$, Cy, H-5), 2.11-2.18 (m, 1H, H-2$_b$), 2.22-2.31 (m, 1H, H-1), 2.59 (t, J=2.3 Hz, 1H, H-3'), 3.14 (t, J=9.5 Hz, 1H, H-4), 3.57 (t, J=5.9 Hz, Gal H-5), 3.65 (dd, J=2.94, 9.77 Hz, 1H, Gal H-3), 3.67-3.92 (m, 8H, H-3, Fuc H-4, 2 Gal H-6, Fuc H-3, 2 H-1'), 3.96 (d, J=2.2 Hz, 1H, Gal H-4), 4.05 (dd, J=2.7, 9.6 Hz, 1H, Lac H-2), 4.69 (d, J=8.0 Hz, 1H, Gal H-1), 4.96-5.00 (m, 2H, Fuc H-1, Fuc H-5), 5.42-5.45 (m, 1H, Gal H-2), 7.48-7.51 (m, 2H, C$_6$H$_5$), 7.60-7.63 (m, 1H, C$_6$H$_5$), 8.05-8.06 (m, 2H, C$_6$H$_5$); $^{13}$C-NMR (125 MHz, MeOD): δ 16.70 (Fuc C-6), 19.22 (Me), 26.51 (Cy), 26.68 (Cy), 27.25 (Cy), 29.39 (C-1'), 33.12 (Cy), 34.17 (Cy), 35.02 (Cy), 35.25 (C-2), 37.25 (C-6), 39.26 (C-5), 42.72 (Lac C-3), 42.93 (C-1), 62.72 (Gal C-6), 67.69, 67.78 (2C, Fuc C-5, Gal C-4), 70.31 (Fuc C-2), 71.42 (Fuc C-3), 72.17 (C-3'), 72.98 (Gal C-2), 73.95 (Fuc C-4), 75.94 (Gal 5-C), 77.96 (Lac C-2), 79.86 (C-3), 80.67 (C-2'), 83.00 (C-4), 83.65 (Gal C-3), 100.42 (Fuc C-1), 100.55 (Gal C-1), 129.74 ( ), 130.86 ( ), 131.51 ( ), 134.38 (6C, C$_6$H$_5$), 166.85 (O(C=O)Ph), 176.52 (CONH), 178.75 (COOH); [a]$_D^{20}$=−67.5 (c=1.6, MeOH); IR (KBr): ν=3436 (vs, OH), 3308 (s, C≡C), 2927 (s), 2851 (m), 1727 (s, C=O), 1651 (m, C=O), 1534 (w), 1450 (m), 1341 (m), 1314 (m), 1270 (s), 1160 (m), 1111 (vs), 1079 (vs), 1030 (s), 966 (w), 773 (w), 712 (m), 674 (w), 631 (w) cm$^{-1}$.

Synthesis of Product 21

(1R,3R,4R,5S)-3-[2-O-Benzoyl-3-O-((1S)-1-carboxy-2-cyclohexyl-ethyl)-(β-D-galactopyranosyl)oxy]-N-(but-3-yn-1-O-4-[(α-L-fucopyranosyl)oxy]-5-methyl-cyclohexanecarboxamide Following general procedure II, 17 (80 mg, 0.0925 mmol) was reacted with TBAF (185 μL, 0.185 mmol) in 3.5 mL anhydrous THF. After purification with RP-18 chromatography, 68 mg (93%) of 21 was obtained as a white solid.

$^1$H-NMR (500 MHz, MeOD): δ 0.53-0.76 (m, 4H, Cy), 0.86-0.97 (m, 1H, Cy), 1.11 (d, J=6.3 Hz, 3H, Me), 1.14-1.27 (m, 3H, Cy, H-6$_a$, H-2$_a$), 1.27-1.38 (m, 4H, Cy), 1.34 (d, J=6.5 Hz, 3H, Fuc H-6), 1.38-1.46 (m, 1H, Lac H-3$_a$), 1.46-1.54 (m, 1H, Lac H-3$_b$), 1.54-1.73 (m, 3H, H-6$_b$, Cy, H-5), 2.13 (d, J=11.8 Hz, 1H, H-2$_b$), 2.21-2.32 (m, 4H, H-1, 2 H-2', H-4'), 3.15 (t, J=9.5 Hz, 1H, H-4), 3.18-3.27 (m, 2H, H-1'), 3.54-3.59 (m, 1 H, Gal H-5), 3.63-3.82 (m, 6H, Gal H-3, H-3, Fuc H-2, Fuc H-4, 2 Gal H-6), 3.87 (dd, J=3.1, 10.3 Hz, 1H, Fuc H-3), 3.96 (d, J=1.8 Hz, 1H, Gal H-4), 4.05 (dd, J=2.7, 9.6 Hz, 1H, Lac H-1), 4.68 (d, J=8.0 Hz, 1H, Gal H-1), 4.94-5.92 (m, 2H, Fuc H-1, Fuc H-5), 5.41-5.45 (m, 1H, Gal H-2), 7.48-7.51, 7.61-7.64, (2 m, 3H, C$_6$H$_5$), 8.06-8.07 (m, 2H, C$_6$H$_5$); $^{13}$C-NMR (125 MHz, MeOD): δ 16.69 (Fuc C-6), 19.77 (Me), 19.77 (C2'), 26.50 (Cy), 26.67 (Cy), 27.24 (Cy), 33.13 (Cy), 34.16 (Cy), 35.00 (Cy), 35.44 (C-2), 37.36 (C-6), 39.27 (C-5), 39.33 (C-1'), 42.71 (Lac C-3), 43.18 (C-1), 62.72 (Gal C-6), 67.68, 67.77 (2C, Fuc C-5, Gal C-4), 70.31 (Fuc C-2), 70.78 (C-4'), 71.41 (Fuc C-3), 72.99 (Gal C-2), 73.94 (Fuc C-4, 75.93 (Gal C-5), 77.96 (Lac C-2), 79.87 (C-3), 82.22 (C3'), 82.98 (C-4), 83.61 (Gal C-3), 100.40 (Fuc C-1), 100.56 (Gal C-1), 129.71, 130.86, 131.52, 134.36 (6C, C$_6$H$_5$), 166.79 (O(C=O)Ph), 177.12 (CONH), 178.74 (COOH); [a]$_D^{20}$=−72.8 (c=1.15, MeOH); IR (KBr): ν= 3435 (s), 3311 (s, C≡C), 2927 (s), 2853 (m), 2115 (vw), 1727 (s, C=O), 1648 (m, C=O), 1544 (w), 1450 (m), 1364 (m), 1340 (m), 1315 (m), 1270 (s), 1221 (m), 1166 (m), 1111 (vs), 1073 (vs), 1031 (s), 999 (m), 966 (m), 901 (vw), 867 (vw), 806 (vw), 770 (w), 712 (m), 675 (w), 632 (w) cm$^{-1}$.

Synthesis of Product 22

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(pent-4-yn-1-yl)cyclohexanecarboxamide Following general procedure II, 18 (77 mg, 0.0877 mmol) was reacted with TBAF (175 μL, 0.175 mmol) in 3.5 mL anhydrous THF. After purification with RP-18 chromatography, 69 mg (98%) of 22 was obtained as a white solid.

$^1$H-NMR (500 MHz, MeOD): δ 0.50-0.61 (m, 1H, Cy), 0.61-0.75 (m, 3H, Cy), 0.86-0.97 (m, 1 H, Cy), 1.11 (d, J=6.5 Hz, 3 H, Me), 1.15-1.26 (m, 3 H, Cy, H-6$_a$, H-2$_a$), 1.27-1.38 (m, 4H, Cy), 1.34 (d, J=6.5 Hz, 3H, Fuc H-6) 1.39-1.49 (m, 1H, Lac H-3$_b$), 1.51 (ddd, J=3.8, 10.1, 13.7 Hz, 1H, Lac H-3$_a$), 1.55-1.61 (m, 2 H, Cy, H-6$_b$), 1.61-1.71 (m, 3 H, H-2', H-5), 2.08-2.15 (m, 1 H, H-2), 2.18 (td, J=2.6, 7.2 Hz, 2 H, H-3'), 2.20-2.28 (m, 1 H, H-1), 2.29 (t, J=2.6 Hz, 1 H, H-5'), 3.14 (t, J=7.6 Hz, 1H, H-4), 3.14-3.24 (m, 2 H, H-1'), 3.54-3.59 (m, 1 H, Gal H-5), 3.64-3.80 (m, 6 H, Gal H-3, H-3, Fuc H-2, Fuc H-4, 2 Gal H-6), 3.86 (dd, J=3.2, 10.3 Hz, 1 H, Fuc H-3), 3.96 (d, J=2.3 Hz, 1 H, Gal H-4), 4.04 (dd, J=2.6, 9.8 Hz, 1 H, Lac H-2), 4.69 (d, J=8.0 Hz, 1 H, Gal H-1), 4.96 (d, J=4.0 Hz, 1 H, Fuc H-1), 4.98-5.01 (m, 1 H, Fuc H-5), 5.43 (dd, J=8.6, 9.2 Hz, 1 H, Gal H-2), 7.49-7.52, 7.61-7.64 (2 m, 3 H, C$_6$H$_5$), 7.80 (t, J=5.6 Hz, 1H, CONH), 8.05-8.07 (m, 2 H, C$_6$H$_5$); $^{13}$C-NMR (125 MHz, MeOD): δ 16.66, 16.71 (2C, C-3', Fuc C-6), 19.23 (Me), 26.53, 26.70 (2C, Cy), 27.27 (Cy), 29.48 (C-2'), 33.11, 34.17 (2C, Cy), 35.06, 35.47 (2C, Cy, C-2)), 37.39 (C-6), 39.31, 39.39 (2C, C-1', C-5), 42.79 (Lac C-3), 43.31 (C-1), 62.75 (Gal C-6), 67.70, 67.74 (2C, Gal C-4, Fuc C-5), 70.10, 70.29 (2C, Fuc C-2, C-5'), 71.40 (Fuc C-3), 72.99 (Gal C-2), 73.96 (Fuc C-4), 75.95 (Gal C-5), 78.01 (Lac C-2), 79.89 (C-3), 83.00 (C-4), 83.65 (Gal C-3), 84.23 (C-4'), 100.46 (Fuc C-1), 100.57 (Gal C-1), 129.76, 130.85, 131.54, 134.42 (6C, C$_6$H$_5$), 166.8 (O(C=O)Ph), 177.10 (CONH), 179.01 (COOH); [a]$_D^{20}$=−66.4 (c=2.07, MeOH); IR (KBr): ν=3443 (vs, OH), 2928 (s, C≡C), 2115 (vw), 1726 (s, C=O), 1648 (m, C=O), 1544 (w), 1450 (m), 1270 (s), 1166 (m), 1111 (s), 1078 (vs), 1031 (s), 966 (s), 712 (m) cm$^{-1}$.

Synthesis of Product 23

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-N-(hex-5-yn-1-yl)-5-methyl-cyclohexanecarboxamide Following general procedure II, 19 (25 mg, 0.0280 mmol) was reacted with TBAF (84 μL, 0.0840 mmol) in 1 mL anhydrous THF. After purification with preparative HPLC-MS, 20 mg (87%) of 23 was obtained as a white solid.

$^1$H-NMR (500 MHz, MeOD): δ 0.51-0.75 (m, 4H, Cy), 0.86-0.97 (m, 1H, Cy), 1.11 (d, J=6.4 Hz, 3H, Me), 1.16-1.27 (m, 3H, H-6$_a$, H-2$_a$, Cy), 1.27-1.38 (m, 7H, Fuc H-6, Cy), 1.38-1.45 (m, 1H, Lac H3$_a$), 1.46-1.62 (m, 7H, Lac H3$_b$, H-3', H-2', H-6$_b$, Cy), 1.63-1.71 (m, 1H, H-5), 2.08-2.15 (m, 1H, H-2$_b$), 2.16-2.30 (m, 4H, H-4', H-6', H-1), 3.05-3.13 (m, 2H, H-1'), 3.15 (t, J=9.5 Hz, 1H, H-4), 3.57 (t, J=5.8 Hz, 1H, Gal H-5), 3.63-3.82 (m, 6H, Gal H-3, H-3, Fuc H-2, Fuc H-4, Gal H-6), 3.87 (dd, J=2.9, 10.3 Hz, 1H, Fuc H-3), 3.94-3.98 (m, 1H, Gal H-4), 4.02-4.07 (m, 1H, Lac H-2), 4.69 (d, J=8.0 Hz, 1H, Gal H-1), 4.95-5.03 (m, 2H, Fuc H-1, Fuc H-5), 5.44 (t, J=8.9 Hz, 1H, Gal H-2), 7.47-7.53 (m, 2H, C$_6$H$_5$), 7.60-7.65 (m, 1H, C$_6$H$_5$), 8.04-8.09 (m, 2H, C$_6$H$_5$); $^{13}$C-NMR (125 MHz, MeOD): δ 16.71 (Fuc C-6), 18.70 (C-4'), 19.25 (Me), 26.52 (Cy), 26.68 (Cy), 26.90 (C3'), 27.25 (Cy), 29.46 (C-2'), 33.12 (Cy), 34.16 (Cy), 35.04 (Cy), 35.36 (C-2), 37.50 (C-6), 39.33 (C-5), 39.68 (C-1'), 42.77 (Lac C-3), 43.32 (C-1), 62.74 (Gal C-6), 67.69 (Gal C-4), 67.75 (Fuc C-5), 69.85 (C-6'), 70.29 (Fuc C-2), 71.40 (Fuc C-3), 72.98 (Gal C-2), 73.94 (Fuc C-4), 75.94 (Gal C-5), 78.02 (Lac C-2), 79.83 (C-3), 83.00 (C-4), 83.64 (Gal C-3), 84.70 (C-5'), 100.42 (Fuc C-1), 100.51 (Gal C-1), 129.73 (C$_6$H$_5$), 130.85 (C$_6$H$_5$), 131.54 (C$_6$H$_5$), 134.38 (C$_6$H$_5$), 166.79 (O(C=O)Ph), 176.96 (CONH), 178.99 (COOH); IR (KBr): ν=3436 (s, OH), 2928 (s), 2868 (m), 1731 (s, C=O), 1653 (m), 1550 (w), 1451 (m), 1350 (w), 1298 (m), 1270 (s), 1114 (vs), 1078 (vs), 1034 (s), 996 (w), 966 (w), 712 (m) cm$^{-1}$.

Example 2

Figure 4:
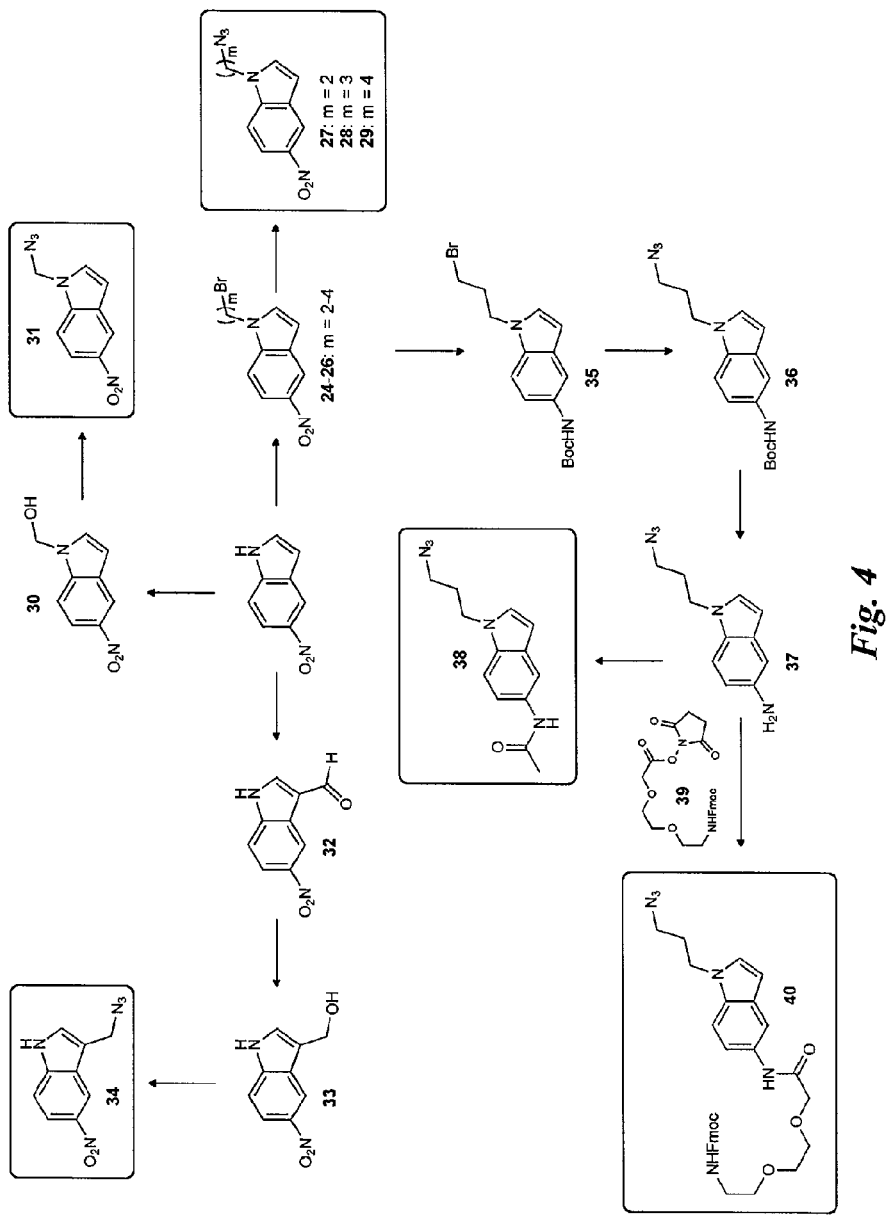
FIG. 4 is a diagram illustrating the synthesis of the indole derivatives starting from 5-nitro-1H-indole.
Figure 5:
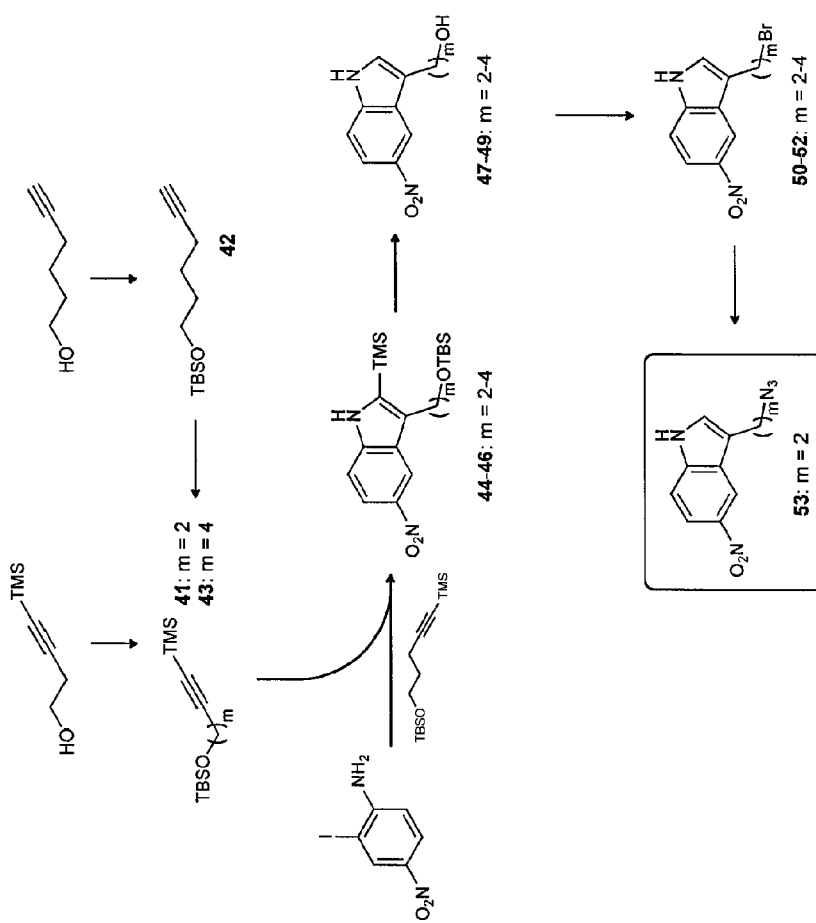
FIG. 5 is a diagram illustrating the synthesis of the indole derivatives starting from 2-iodo-4-nitroaniline (Larock indole synthesis).

Synthesis of the Indole Derivatives
(FIG. 4 and FIG. 5)

Synthesis of Intermediate 24

1-(2-Bromoethyl)-5-nitro-1H-indole 5-nitro-1H-indole (1.00 g, 6.17 mmol) was added to powdered KOH (431 mg, 7.68 mmol) dissolved in DMF (40 mL) at r.t. To this, 1,2-dibromoethane (1.55 mL, 18.5 mmol) was quickly added, and the solution was stirred for 25 h. Water (100 mL) was added to the reaction mixture, and it was extracted with Et$_2$O (3×100 mL). The organic phases were washed with 0.5 M aq. HCl, satd. NaHCO$_3$, and brine (60 mL). The organic layer was dried over Na$_2$SO$_4$, and the solvent was removed under reduced pressure. Silica gel chromatography (EtOAc in petrol ether, gradient 0 to 85%) afforded 24 (198 mg, 19%) as a yellow solid. Approximately 600 mg of the starting material was recovered.

$^1$H-NMR (500 MHz, CDCl$_3$): δ 3.68 (t, J=6.6 Hz, 2H, H-1'), 4.59 (t, J=6.6 Hz, 2H, H-2'), 6.71-6.74 (m, 1H, H-3), 7.29-7.33 (m, 1H, H-2), 7.36-7.40 (m, 1H, H-7), 8.13-8.17 (m, 1H, H-6), 8.59-8.64 (m, 1H, H-4).

Synthesis of Intermediate 25

1-(3-Bromopropyl)-5-nitro-1H-indole 5-nitro-1H-indole (2.01 g, 12.3 mmol) was added to powdered KOH (0.692 g, 12.3 mmol) dissolved in DMF (100 mL) at r.t., leading to a red solution. To this, dibromopropane (3.77 mL, 37.0 mmol) was quickly added, accompanied by a color change to yellow. After 40 min, additional 0.5 mL (4.90 mmol) of dibromopropane was added, whereupon some precipitation occurred. After 17 h of stirring at r.t., water (200 mL) was added to the reaction mixture, and it was extracted with Et$_2$O (3×200 mL). The organic phases were washed with 0.5 M aq. HCl, satd. NaHCO$_3$, and brine (100 mL). The organic layers were dried over Na$_2$SO$_4$, and the solvent was removed under reduced pressure. Silica gel chromatography (EtOAc in petrol ether, gradient 0 to 85%) afforded 25 as a yellow crystals (1.59 g, 46%). 0.565 g (28%) of the starting material was recovered.

$^1$H-NMR (500 MHz, CDCl$_3$): δ 2.35-2.41 (m, 2H, H-2'), 3.30-3.33 (m, 2H, H-3'), 4.40 (t, J=6.5 Hz, 2H, H-1'), 6.70 (m, 1H, H-3), 7.30-7.32 (m, 1H, H-2), 7.40-7.43 (m, 1H, H-7), 8.10-8.13 (m, 1H, H-6), 8.57 (m, 1H, H-4); $^{13}$C-NMR (125 MHz, CDCl$_3$): δ 30.05 (C-3'), 32.70 (C-2'), 44.53 (C-1'), 104.54 (C-3), 109.33 (C-7), 117.52 (C-6), 118.42 (C-4), 127.92 (C-9), 131.22 (C-2), 138.84 (C-8), 141.79 (C-5); elemental analysis calcd (%) for C$_{11}$H$_{11}$BrN$_2$O$_2$ (283.12): C, 53.87; H, 4.52; N, 28.56. found: C, 53.86/53.77; H, 4.71/4.65; N, 28.29/28.32. IR (KBr): ν=1606 (vw), 1577 (vw), 1511 (s, NO$_2$), 1480 (m), 1459 (m), 1431 (vw), 1404 (w), 1331 (vs, NO$_2$), 1296 (s), 1253 (m), 1226 (m), 1183 (w), 1157 (w), 1068 (m), 975 (vw), 934 (vw), 902 (w), 816 (w), 768 (w), 749 (s) cm$^{-1}$.

Synthesis of Intermediate 26

1-(4-Bromobutyl)-5-nitro-1H-indole

To a solution of 5-nitro-1H-indole (2.00 g, 12.3 mmol) in anhydrous
EtOAc (20 mL) was added K$_2$CO$_3$ (3.39 g, 24.5 mmol) and TBAB (4.76 g, 14.8 mmol). The suspension was stirred at 50° C. for 30 min followed by the addition of 1,4-dibromobutane (1.74 mL, 14.8 mmol). Stirring was continued under reflux for 21 h. Upon completion of the reaction, water (20 mL) was added to the reaction mixture, the phases were separated, and the aqueous phase was further extracted with EtOAc (2×40 mL). The organic layers were washed with 0.5 M aq. HCl, satd. NaHCO$_3$, and brine (20 mL), subsequently dried over Na$_2$SO$_4$ and concentrated. The residue was purified using silica gel chromatography (EtOAc in petrol ether) to afford bromide 26 as a yellow solid (1.67 g, 46%).

$^1$H-NMR (500 MHz, CDCl$_3$): δ 1.83-1.90 (m, 2H, H-2'), 2.02-2.09 (m, 2H, H-3'), 3.40 (t, J=6.4 Hz, 2H, H-4'), 4.22 (t, J=7.0 Hz, 2H, H-1'), 6.68-6.71 (m, 1H, H-3), 7.24-7.25 (m, 1H, H-2), 7.34-7.38 (m, 1H, H-7), 8.11-8.15 (m, 1H, H-6), 8.58-8.61 (m, 1H, H-4).

Synthesis of Product 27

1-(2-Azidoethyl)-5-nitro-1H-indole

NaN$_3$ (69.6 mg, 1.07 mmol) was added to a solution of bromide 24 (198 mg, 0.736 mmol) in DMF (2 mL), and the resulting suspension was stirred at 60° C. After 12 h, water (10 mL) was added, and the reaction mixture was extracted with EtOAc (3×20 mL). The organic layers were washed with water and brine (10 mL) and subsequently dried over Na$_2$SO$_4$. Silica gel chromatography (EtOAc in petrol ether) afforded azide 27 (90 mg, 52%) as a yellow solid.

$^1$H-NMR (500 MHz, DMSO-d6): δ 3.76 (t, J=5.6 Hz, 2H, H-2'), 4.48 (t, J=5.6 Hz, 2H, H-1'), 6.77-6.83 (m, 1H, H-3), 7.66-7.70 (m, 1H, H-2), 7.74-7.80 (m, 1H, H-7), 8.02-8.08 (m, 1H, H-6)), 8.54-8.62 (m, 1H, H-4); $^{13}$C-NMR (125 MHz, DMSO-d6): δ 45.32 (C-1'), 50.66 (C-2'), 104.18 (C-3), 110.51 (C-7), 116.53 (C-6), 117.59 (C-4), 127.50 (C-9), 132.56 (C-2), 138.95 (C-8), 140.86 (C-5).

Synthesis of Product 28

1-(3-Azidopropyl)-5-nitro-1H-indole

NaN$_3$ (434 mg, 6.68 mmol) was added to a solution of bromide 25 (1.34 g, 4.73 mmol) in DMF (10 mL), and the resulting suspension was stirred at 55° C. After 12 h, water (20 mL) was added, and the reaction mixture was extracted with EtOAc (3×30 mL). The organic layers were washed with water and brine (20 mL) and subsequently dried over Na$_2$SO$_4$. Silica gel chromatography (EtOAc in petrol ether) afforded azide 28 (950 mg, 82%) as a yellow solid.

$^1$H-NMR (500 MHz, DMSO-d6): δ 2.03 (p, J=6.8 Hz, 2H, H-2'), 3.32 (t, J=6.7 Hz, 2H, H-3'), 4.34 (t, J=7.0 Hz, 2H, H-1'), 6.76-6.79 (m, 1H, H-3), 7.65-7.69 (m, 1H, H-2), 7.69-7.75 (m, 1H, H-7), 8.01-8.07 (m, 1H, H-6), 8.58 (s, 1H, H-4); $^{13}$C-NMR (125 MHz, DMSO-d6): δ 28.97 (C-2'), 43.30 (C-1'), 48.00 (C-3'), 103.91 (C-3), 110.32 (C-7), 116.46 (C-6), 117.64 (C-4), 127.36 (C-9), 132.50 (C-2), 138.68 (C-5), 140.73 (C-5).

Synthesis of Product 29

1-(4-Azidobutyl)-5-nitro-1H-indole

NaN$_3$ (531 mg, 8.17 mmol) was added to a solution of bromide 26 (1.60 g, 5.38 mmol) in DMF (5 mL), and the resulting suspension was stirred at 55° C. After 14 h, water (10 mL) was added, and the reaction mixture was extracted with EtOAc (3×20 mL). The organic layers were washed with water and brine (10 mL) and subsequently dried over Na$_2$SO$_4$. Silica gel chromatography (EtOAc in petrol ether) afforded azide 29 (1.10 g, 79%) as a yellow solid.

$^1$H-NMR (500 MHz, DMSO-d6): δ 1.43-1.50 (m, 2H, H-3'), 1.78-1.85 (m, 2H, H-2'), 3.31-3.38 (m, 2H, H-4'), 4.30 (t, J=7.0 Hz, 2H, H-1'), 6.74-6.77 (m, 1H, H-3), 7.66-7.68 (m, 1H, H-2), 7.71-7.75 (m, 1H, H-7), 8.00-8.05 (m, 1H, H-6), 8.56-8.58 (m, 1H, H-4); $^{13}$C-NMR (125 MHz, DMSO-d6): δ 25.63 (C-3'), 27.10 (C-2'), 45.44 (C-1'), 50.15 (C-4'), 103.70 (C-3), 110.40 (C-7), 116.37 (C-6), 117.64 (C-4), 127.32 (C-9), 132.55 (C-2), 138.67 (C-8), 140.66 (C-5); elemental analysis calcd (%) for C$_{12}$H$_{13}$N$_5$O$_2$ (259.26): C, 55.59; H, 5.05; N, 27.01. found C, 55.66/55.64; H, 5.20/5.21; N, 26.81/26.79.

Synthesis of Intermediate 30

(5-Nitro-1H-indol-1-yl)methanol 5-nitro-1H-indole (995 mg, 6.14 mmol) and K$_2$CO$_3$ (396 mg, 2.87 mmol) were dissolved in EtOH in a bomb tube. The solution was stirred at 60° C. for 5 min, and 8 mL of freshly prepared ~30% aq. methanal (preparation: 3.00 g paraformaldehyde and 0.901 g of K$_2$CO$_3$ were suspended in 10 mL H$_2$O and stirred at 60° C. until complete dissolution of the paraformaldehyde) were added. Stirring was continued at 60° C. for another 20 min. After removal of the solvent, the crude mixture was redissolved in EtOAc and adsorbed on silica gel. The adsorbed material was subjected to silica gel chromatography (EtOAc in petrol ether, gradient 30 to 70%) to afford alcohol 30 as a yellow solid (784 mg, 66%).

$^1$H-NMR (500 MHz, MeOD): δ 5.62 (s, 2H, H-1'), 6.67-6.72 (m, 1H, H-3), 7.48-7.52 (m, 1H, H-2), 7.60-7.65 (m, 1H, H-7), 8.05-8.10 (m, 1H, H-6), 8.50-8.54 (m, 1H, H-4); $^{13}$C-NMR (125 MHz, MeOD): δ 70.45 (C-1'), 105.21 (C-3), 111.17 (C-7), 117.95 (C-6), 118.54 (C-4), 129.92 (C-9), 132.41 (C-2), 140.12 (C-8), 143.16 (C-5); elemental analysis calcd (%) for C$_9$H$_8$N$_2$O$_3$ (192.17): C, 56.25; HH, 4.20; N, 14.58. found: C, 56.14/56.35; HH, 4.21/4.20; N, 14.60/14.72. IR (KBr): ν=3486 (vs, OH), 1609 (w), 1580 (vw), 1512 (s, NO$_2$), 1466 (m), 1399 (w), 1331 (vs, NO$_2$), 1279 (s), 1206 (w), 1147 (vw), 1100 (w), 1073 (w), 1040 (s), 988 (vw), 894 (vw), 814 (vw), 763 (vw), 744 (s), 722 (vw) cm$^{-1}$.

Synthesis of Product 31

1-(Azidomethyl)-5-nitro-1H-indole

Alcohol 30 (770 mg, 4.01 mmol) was dissolved in anhydrous THF (13 mL) under argon. At −15° C. (ice-salt bath), MeSO$_2$Cl (0.312 mL, 4.01 mmol) and Et$_3$N (1.1 mL, 8.02 mmol) were added. After 10 min, the ice bath was removed and stirring was continued for 1 h, when 15-Crown-5 (0.397 mL, 2.01 mmol) and NaN$_3$ (521 mg, 8.02 mmol) were added to the solution. After another 5 h, the solvent was removed. The crude mixture was dissolved in EtOAc (75 mL) and H$_2$O (50 mL). The two phases were separated, and the organic phase was washed with brine (50 mL). The aqueous phase was extracted with EtOAc (2×50 mL). The combined organic layers were dried over Na$_2$SO$_4$, and the solvent was removed under reduced pressure. After silica gel chromatography (EtOAc in petrol ether, gradient 20 to 70%), the azide 31 was obtained as yellow crystals (297 mg, 34%). Furthermore, 30 mg of 5-nitro-1H-indole and 42 mg (5%) of the starting material were isolated.

$^1$H-NMR (500 MHz, CDCl$_3$): δ 5.51 (s, 2H, H-1'), 6.75-6.79 (m, 1H, H-3), 7.33-7.35 (m, 1H, H-2), 7.47-7.50 (m, 1H, H-7), 8.18-8.21 (m, 1H, H-6), 8.60-8.62 (m, 1H, H-4); $^{13}$C-NMR (125 MHz, CDCl$_3$): δ 61.56 (C-1'), 106.03 (C-3), 109.68 (C-7), 118.43 (C-6), 118.50 (C-4), 128.73 (C-9), 130.71 (C-2), 138.88 (C-8), 142.84 (C-5); elemental analysis calcd (%) for C$_9$H$_7$N$_5$O$_2$ (217.18): C, 49.77; H, 3.25; N, 32.25. found: C, 49.83/49.59; H, 3.28/3.28; N, 32.56/32.46. IR (KBr): ν=3101 (vw), 2924 (vw), 2118 (m, N$_3$), 2092 (m, N$_3$), 1612 (w), 1583 (vw), 1509 (s, NO$_2$), 1480 (m), 1451 (m), 1401 (vw), 1336 (vs, NO$_2$/N$_3$), 1287 (vs, N$_3$), 1266 (m), 1231 (m), 1208 (w), 1179 (m), 1147 (w), 1076 (w), 1065 (w), 1029 (vw), 934 (vw), 906 (w), 876 (w), 821 (w), 745 (s) cm$^{-1}$.

Synthesis of Intermediate 32

5-Nitro-1H-indole-3-carbaldehyde

Intermediate 32 was synthesized according to the procedure described in [S. Shelke, B. Cutting, X. Jiang, H. Koliwer-Brandl, D. S. Strasser, S. Kelm, O, Schwardt, B. Ernst, Angew. Chem. Int. Ed. 2010, 49, 5721-5725.].

$^1$H-NMR (500 MHz, DMSO-d6): δ 7.71-7.74 (m, 1H, H-7), 8.14-8.17 (m, 1H, H-6), 8.57 (s, 1H, H-2), 8.94-8.96 (m, 1H, H-4), 10.03 (s, 1H, H-1'); $^{13}$C-NMR (125 MHz, CDCl$_3$): δ 113.29 (C-7), 117.07 (C-4), 118.83 (C-3), 119.07 (C-6), 123.55 (C-9), 140.17 (C-2), 141.51 (C-5), 142.91 (C-2), 185.59 (C-1').

Synthesis of Intermediate 33

(5-Nitro-1H-indol-3-yl)methanol

Intermediate 33 was synthesized according to the procedure described in [S. Shelke, B. Cutting, X. Jiang, H. Koliwer-Brandi, D. S. Strasser, S. Kelm, O. Schwardt, B. Ernst, Angew. Chem. Int. Ed. 2010, 49, 5721-5725.].

$^1$H-NMR (500 MHz, MeOD): δ 4.84 (s, 2H, H-1'), 7.43 (s, 1H, H-2), 7.45-7.49 (m, 1H, H-7), 8.03-8.07 (m, 1H, H-6), 8.66-8.69 (m, 1H, H-4); $^{13}$C-NMR (125 MHz, MeOD): δ 56.74 (C-1'), 112.46 (C-7), 117.20 (C-4), 118.02 (C-6), 119.29 (C-3), 127.53 (C-9), 128.04 (C-2), 141.38 (C-8), 142.56 (C-5); elemental analysis calcd (%) for $C_9H_8N_2O_3$ (192.17): C, 56.25; H, 4.20; N, 14.58. found: C, 56.18/56.00; H, 4.41/4.45; N, 14.65/14.60.

Synthesis of Product 34

3-(Azidomethyl)-5-nitro-1H-indole

To alcohol 33 (752 mg, 3.91 mmol) suspended in toluene (10 mL) under argon were added diphenyl phosphoryl azide (1.0 mL, 4.69 mmol) and dropwise at −10° C. DBU (0.7 mL, 4.69 mmol). The suspension was allowed to warm to r.t., and 5 mL THF were added leading to the formation of two phases. The reaction was continued under vigorous stirring for 18 h. After removal of the THF in vacuo, EtOAc (80 mL) was added to the reaction mixture, and the organic phases were washed with satd. aq. $NaHCO_3$ (2×40 mL), 0.5 M aq. HCl (40 mL), satd. aq. $NaHCO_3$ (40 mL) and brine (40 mL). The aqueous layers were extracted with EtOAc (2×80 mL), and the organic phase was dried over $Na_2SO_4$. Silica gel chromatography (1. $CH_2Cl_2$/MeOH 10:1 in $CH_2Cl_2$, gradient 0 to 100%; 2. $CH_2Cl_2$) afforded only impure product. Subsequent crystallization from $CH_2Cl_2$ afforded pure azide 34 as yellow crystals (658 mg, 78%). 140 mg (19%) of the starting material was recovered.

$^1$H-NMR (500 MHz, DMSO-d6): δ 4.70 (s, 2H, H-1'), 7.56-7.62 (m, 1H, H-7), 7.75 (s, 1H, H-2), 8.01-8.08 (m, 1H, H-6), 8.65 (s, 1H, H-4), 11.90 (s, 1H, NH); $^{13}$C-NMR (125 MHz, DMSO-d6): δ 45.16 (C-1'), 111.57 (C-3), 112.38 (C-7), 115.76 (C-4), 117.07 (C-6), 125.88 (C-9), 129.50 C-2), 139.53 (C-8), 140.88 (C-5); elemental analysis calcd (%) for $C_9H_7N_5O_2$ (217.18): C, 49.77; H, 3.25; N, 32.25. found: C, 49.61/49.73; H, 3.31/3.27; N, 32.07/32.14. IR (KBr): ν=3257 (m, NH), 2117 (vs, $N_3$), 1625 (w), 1580 (w), 1551 (m), 1515 (s, $NO_2$), 1472 (m), 1456 (m), 1436 (m), 1376 (w), 1331 (vs, $N_3/NO_2$), 1261 (m), 1224 (m), 1196 (m), 1128 (w), 1113 (m), 1102 (m), 1045 (w), 976 (w), 939 (vw), 920 (vw), 894 (m), 863 (w), 836 (m), 816 (m), 782 (w), 769 (w), 751 (m), 735 (m), 686 (m), 631 (m), 613 (w), 563 (m), 559 (m) $cm^{-1}$.

Synthesis of Intermediate 35 tert-Butyl N-[1-(3-bromopropyl)-1H-indol-5-yl]carbamate

Nitroindole 25 (700 mg, 2.50 mmol) and $PtO_2$ (35 mg, 5% w/w) were suspended in a solution of $Boc_2O$ (1.76 g, 8.06 mmol) in EtOH (23 mL) under argon. The flask was flushed with $H_2$, and the solution was stirred under $H_2$ (atm. press.) at r.t. for 45 min (color change from yellow to green), when another 35 mg of $PtO_2$ was added. After stirring for additional 30 min, the now colorless mixture was filtrated (PTFE membrane filter) and the solvent was removed in vacuo. The residue was dissolved in EtOAc (100 mL) and washed with 0.5 M aq. HCl (50 mL), satd. aq. $NaHCO_3$ (50 mL), and brine (50 mL). The organic layer was dried over $Na_2SO_4$, and the solvent was removed under reduced pressure. After purification by silica gel chromatography (EtOAc in petrol ether, gradient 0 to 25%), 35 (637 mg, 72%) was obtained as a pale yellow oil, which eventually crystallized and turned pink after 24 h at −18° C.

$^1$H-NMR (500 MHz, MeOD): δ 1.50 (s, 9H, $^t$Bu-H), 2.28 (p, J=6.4 Hz, 2H, H-2'), 3.28 (m, 2H, H-3'), 4.27 (t, J=6.5 Hz, 2H, H-1'), 6.35 (m, 1H, H-3), 7.10 (m, 1H, H-6), 7.16 (m, 1H, H-2), 7.30 (m, 1H, H-7), 7.57 (s, 1H, H-4); $^{13}$C-NMR (125 MHz, MeOD): δ 28.80 ($^t$Bu-$CH_3$), 31.16 (C-3'), 34.31 (C-2'), 45.05 (C-1'), 80.44 ($^t$Bu-$CCH_3$), 102.08 (H-3), 110.37 (C-7), 112.84 (C-6), 116.67 (C-4), 129.81 (C-2), 130.26 (C-9), 132.41 (C-8), 134.36 (C-5), 156.27 (OCONH); elemental analysis calcd (%) for $C_{16}H_{21}BrN_2O_2$ (353.25): C, 54.40; H, 5.99; N, 7.93. found: C, 54.29/54.35; H, 5.97/5.96; N, 7.86/7.76. IR (KBr): ν=2972 (w) 2932 (w), 1695 (vs, C=O), 1625 (vw), 1584 (m), 1532 (s), 1509 (m), 1490 (s), 1447 (m), 1441 (m), 1392 (m), 1367 (s), 1334 (m), 1312 (vw), 1295 (m), 1287 (m), 1261 (m), 1232 (s), 1163 (vs), 1092 (vw), 1053 (m), 1027 (vw), 889 (vw), 863 (vw), 825 (vw), 802 (vw), 756 (w), 726 (w), 623 (vw), 563 (vw) $cm^{-1}$.

Synthesis of Intermediate 36 tert-Butyl N-[1-(3-azidopropyl)-1H-indol-5-yl]carbamate

To a solution of 35 (570 mg, 1.61 mmol) in anhydrous DMF (15 mL), $NaN_3$ (528 mg, 8.12 mmol) was added at r.t. After 2 h, $H_2O$ (50 mL) was added to the reaction mixture, and the aqueous layers were extracted with EtOAc (100 mL). The organic layers were washed with satd. $NaHCO_3$, brine, and dried over $Na_2SO_4$. After removal of the solvent under reduced pressure, the crude product was purified by silica gel chromatography (EtOAc in petrol ether, gradient 0 to 25%) to afford 36 (458 mg, 90%) as slightly yellowish crystals.

$^1$H-NMR (500 MHz, MeOD): δ 1.52 (s, 9H, $^t$Bu-H), 2.02 (p, J=6.6 Hz, 2H, H-2'), 3.22 (t, J=6.5 Hz, 2H, H-3'), 4.22 (t, J=6.7 Hz, 2H, H-1'), 6.36-6.39 (m, 1H, H-3), 7.10-7.15 (m, 1H, H-6), 7.15-7.17 (m, 1H, H-2), 7.28-7.32 (m, 1H, H-7), 7.59 (s, 1H, H-4). $^{13}$C-NMR (125 MHz, MeOD): δ 28.80 ($^t$Bu-$CH_3$), 30.51 (C-2'), 44.02 (C-1'), 49.54 (C-3'), 80.40 ($^t$Bu-$CCH_3$), 102.01 (H-3), 110.27 (C-7), 112.79 (C-6), 116.63 (C-4), 129.72 (C-2), 130.20 (C-9), 132.32 (C-8), 134.38 (C-5), 156.24 (OCONH); elemental analysis calcd (%) for $C_{16}H_{21}N_5O_2$ (315.37): C, 60.94; H, 6.71; N, 22.21. found: 61.07/61.04; H, 6.69/6.70; N, 22.18/22.17. IR (KBr): ν=2976 (w), 2930 (w), 2873 (vw), 2099 (vs, $N_3$), 1697 (s, C=O), 1625 (vw), 1584 (w), 1529 (m), 1510 (m), 1489 (s), 1450 (m), 1440 (m), 1392 (w), 1366 (m), 1334 (w), 1286 (m), 1236 (m), 1159 (s), 1096 (vw), 1085 (vw), 1051 (w), 1051 (m), 1026 (w) $cm^{-1}$.

Synthesis of Intermediate 37

1-(3-Azidopropyl)-1H-indol-5-amine

Carbamate 36 (408 mg, 1.29 mmol) was dissolved in $CH_2Cl_2$ (40 mL), and trifluoroacetic acid (3 mL) was added. After stirring at r.t. for 30 min, the solvent was removed in vacuo, and the mixture was co-evaporated with toluene. The residue was dissolved in EtOAc (50 mL), the organic layer was washed with satd. aq. $NaHCO_3$ and brine (30 mL), and the aqueous layers were extracted with EtOAc (50 mL). The crude product obtained after drying the combined organic phase over $Na_2SO_4$ and removal of the solvent under reduced pressure was subjected to silica gel chromatography (MeOH in $CH_2Cl_2$ 10:1). The amine 37 (239 mg, 86%) was obtained as a mixture of inseparable products (brownish oil).

$^1$H-NMR (500 MHz, MeOD): δ 1.52 (s, 9H, $^t$Bu-H), 2.02 (p, J=6.6 Hz, 2H, H-2'), 3.22 (t, J=6.5 Hz, 2H, H-3'), 4.22 (t, J=6.7 Hz, 2H, H-1'), 6.37 (m, 1H, H-3), 7.13 (m, 1H, H-6), 7.16 (m, 1H, H-2), 7.30 (m, 1H, H-7), 7.59 (s, 1H, H-4).

Synthesis of Product 38

N-[1-(3-Azidopropyl)-1H-indol-5-yl]acetamide

To a solution of amine 37 (43 mg, 0.200 mmol) was added Et$_3$N (28 µL, 0.200 mmol) and Ac$_2$O (18 µL, 0.200 mmol), and the solution was stirred for 3 h. The solvent was removed in vacuo and the residue purified using silica gel chromatography (EtOAc in CH$_2$Cl$_2$). 38 (44 mg, 86%) was obtained as a mixture of inseparable products (brownish oil).

$^1$H-NMR (500 MHz, CDCl$_3$): δ 1.92-1.96 (m, 2H, H-2'), 2.07 (s, 3H, Ac-Me), 3.12 (t, J=6.3 Hz, 2H, H-3'), 4.09 (t, J=6.6 Hz, 2H, H-1'), 6.34-6.35 (m, 1H, H-3), 6.97-6.99 (m, 1H, H-2), 7.14-7.16 (m, 2H, H-6, Ind H-7), 7.70 (s, 1H, H-4); $^{13}$C-NMR (125 MHz, CDCl$_3$): δ 24.38 (Ac-Me), 29.35 (C-2'), 43.14 (C-1'), 48.33 (C-3'), 101.72 (C-3), 109.33 (C-7), 113.41 (C-4), 116.48 (C-6), 128.71, 128.72 (2C, C-2, C-9), 130.38 (C-8), 133.42 (C-5), 168.85 (MeCONH). MS: m/z calcd for C$_{13}$H$_{15}$N$_5$O [M+Na]$^+$: 280.12. found: 280.20.

Synthesis of Intermediate 39

2,5-Dioxopyrrolidin-1-yl 2-[2-(2-{[(9H-fluoren-9-ylmethoxy)carbonyl]amino}ethoxy)ethoxy]acetate 2-[2-(2-{[(9H-fluoren-9-ylmethoxy)carbonyl]amino}ethoxy)ethoxy]acetic acid (185 mg, 0.480 mmol) and N-hydroxysuccinimide (110 mg, 0.956 mmol) were dissolved in anhydrous THF (1.5 mL). DIC was added dropwise to the solution at r.t., leading to the precipitation of a white solid. After 2 h, the reaction mixture was filtrated through a PTFE membrane filter (0.2 µm), and the solvent was removed. The crude product was redissolved in Et$_2$O. The organic phase was washed with aq. NaHCO$_3$ and 0.5 M aq. HCl. The organic layer was dried over Na$_2$SO$_4$, and the solvent was removed. The crude product was dissolved in CH$_2$Cl$_2$, and the solution was filtrated. After removal of the solvent, the crude product 39 (210 mg) was used in the synthesis of 40 without further purification.

Synthesis of Product 40

9H-Fluoren-9-ylmethyl-N-{2-[2-({[1-(3-azidopropyl)-1H-indol-5-yl]carbamoyl}methoxy)ethoxy]ethyl}carbamate Amine 37 (50 mg, 0.232 mmol) and succinimide ester 39 (120 mg, 0.249 mmol) were dissolved in anhydrous DMF (1 mL) and stirred at r.t. for 15 h. The solvent was removed in vacuo, and the residue was purified using silica gel chromatography (EtOAc in CH$_2$Cl$_2$, gradient 0 to 80%). 70 mg (52%) of 40 was obtained as mixture of inseparable products (green-yellow oil).

$^1$H-NMR (500 MHz, CDCl$_3$): δ 1.88-1.96 (m, 2H, H-2'), 3.10 (t, J=6.3 Hz, 2H, H-3'), 3.32-3.38 (m, 2H, H-6"), 3.56 (t, J=5.0 Hz, 2H, H-5"), 3.64 (d, J=4.2 Hz, 2H, H-4"), 3.73 (d, J=4.4 Hz, 2H, H-3"), 4.02-4.11 (m, 5H, H-9", H-2". H-1'), 4.25 (d, J=7.0 Hz, 2H, H-8"), 6.36-6.40 (m, 1H, Ind H-3), 6.96-6.99 (m, 1H, Ind H-2), 7.15-7.25 (m, 4H, Ind H-6. Ind H-7, B), 7.27-7.34 (m, 2H, C), 7.42-7.48 (m, 2H, A), 7.64-7.71 (m, 2H, D), 7.79-7.82 (m, J=1.4 Hz, 1H, Ind H-4), 8.56 (s, 1H, CONH); $^{13}$C-NMR (125 MHz, CDCl$_3$): δ 29.43 (C-2'), 40.82 (C-6"), 43.23 (C-1'), 47.31 (C-9"), 48.40 (C-3'), 66.83 (C-8"), 70.23, 70.43, 70.90, 71.28, 101.91 (C-3), 109.60 (C-7), 113.11 (C-4), 115.99 (C-6), 120.11 (Fmoc-C), 125.22 (Fmoc-C), 127.19 (Fmoc-C), 127.83 (Fmoc-C), 128.91 (Fmoc-C), 128.93 (Fmoc-C), 129.62 (C-8), 133.63 (C-5), 141.41 (Fmoc-C), 144.06 (Fmoc-C), 156.60 (OCONH), 167.97 (CH$_2$CONH); MS: m/z calcd for C$_{32}$H$_{34}$N$_6$O$_5$ [M+Na]$^+$: 605.25. found: 605.22.

Synthesis of Intermediate 41 tert-Butyldimethyl[(4-(trimethylsilyl)but-3-yn-1-yl)oxy]silane

To a solution of 4-trimethylsilyl-3-butyne-1-ol (854 mg, 6.0 mmol) in DMF (4 mL) was added imidazole (816 mg, 12.0 mmol), followed by tert-butyldimethylsilyl chloride (1.05 g, 7.2 mmol). After stirring at r.t. overnight, the reaction mixture was poured into 10% aq. NaHCO$_3$ and extracted with hexane (3×10 mL). The combined organic phases were washed with brine, dried over Na$_2$SO$_4$ and concentrated to give 41 (1.53 g, quant.) as a colorless oil.

$^1$H NMR (500 MHz, CDCl$_3$): δ 0.09 (s, 6H, 2 CH$_3$), 0.14 (s, 9H, Si(CH$_3$)$_3$), 0.88 (s, 9H, C(CH$_3$)$_3$), 2.44 (t, J=7.0 Hz, 2H, CH$_2$), 3.72 (t, J=7.0 Hz, 2H, CH$_2$).

Synthesis of Intermediate 42 tert-Butyl(hex-5-yn-1-yloxy)dimethylsilane

Hex-5-yn-1-ol (1.25 g, 12.7 mmol) was dissolved in anhydrous CH$_2$Cl$_2$ under argon. At 0° C., Et$_3$N (2.6 mL, 19.1 mmol) and tert-butyldimethylsilyl chloride (2.29 g, 15.2 mmol) were added via a syringe. After 30 min of stirring, the solution was allowed to warm to r.t., which led to precipitation of a white solid. After another 4 h of stirring, the reaction mixture was washed with 0.5 M aq. HCl, satd. aq. NaHCO$_3$, and brine (5 mL). The aqueous layers were washed with CH$_2$Cl$_2$ (2×10 mL), and the combined organic phases were dried over Na$_2$SO$_4$, filtrated through a silica plug and again dried over Na$_2$SO$_4$. The solvent was removed in vacuo yielding 42 (2.31 g, 85%) as a colorless liquid, which was used without further purification.

$^1$H-NMR (500 MHz, MeOD): δ 0.04 (d, J=2.7 Hz, 6H, Si—CH$_3$), 0.89 (s, 9H, $^t$Bu-CH$_3$), 1.54-1.67 (m, 4H, H-3, H-2), 1.93 (t, J=2.6 Hz, 1H, H-6), 2.21 (td, J=2.5, 6.8 Hz, 2H, H-4), 3.63 (t, J=6.0 Hz, 2H, H-1); $^{13}$C-NMR (125 MHz, MeOD): δ 5.24 (2C, Si—CH$_3$), 18.29 (C-4), 18.41 ($^t$Bu-C) 25.04 (C-3), 26.03 (3C, $^t$Bu-CH$_3$), 31.89 (C-2), 62.66 (C-1), 68.33 (C-6), 84.59 (C-5).

Synthesis of Intermediate 43 tert-Butyldimethyl[(6-(trimethylsilyl)hex-5-yn-1-yl)oxy]silane

Under argon, intermediate 42 (2.3 g, 10.9 mmol) was dissolved in anhydrous THF (10 mL) at 0° C., and 1.6 M tert-butyllithium in pentane (8.12 mL, 13.0 mmol) was added over a period of 25 min via a syringe, followed by the addition of trimethylsilyl chloride (1.64 mL, 13.0 mmol). The resulting suspension was allowed to warm to r.t. and stirred for 14 h. Et$_2$O (5 mL) and 0.5 M HCl (2 mL) were added to the reaction mixture, which was then washed with H$_2$O, 0.5 M HCl, aq. NaHCO$_3$, and brine (10 mL). The aqueous layers were extracted with Et$_2$O (2×30 mL), the combined organic layers were dried over Na$_2$SO$_4$ and concentrated in vacuo. 43 (2.99 g, 97%) was obtained as a yellow oil, which was used without further purification.

$^1$H-NMR (500 MHz, CDCl$_3$): δ 0.04 (s, 6H, TBS-CH$_3$), 0.13 (s, 9H, TMS-CH$_3$), 0.88 (s, 9H, $^t$Bu-CH$_3$), 1.51-1.64 (m, 4H, H-3, H-2), 2.23 (t, J=6.8 Hz, 2H, H-4), 3.62 (t, J=6.1 Hz,

2H, H-1); $^{13}$C-NMR (125 MHz, CDCl$_3$): δ -5.14 (TBS-CH$_3$), 0.31 (TMS-CH$_3$), 18.47 ($^t$Bu-C—CH$_3$), 19.78 (C-4), 25.19 (C-3), 26.10 ($^t$Bu-CH$_3$), 32.03 (C-2), 62.83 (C-1), 84.59 (C-6), 107.52 (C-5).

Synthesis of Intermediate 44

3-[2-(tert-Butyldimethylsilyloxy)ethyl]-5-nitro-2-(trimethylsilyl)-1H-indole A mixture of 2-iodo-4-nitroaniline (792 mg, 3.00 mmol), 41 (1.54 g, 6.00 mmol), KOAc (1.47 g, 15.0 mmol), LiCl (127 mg, 3.00 mmol) and Pd(OAc)$_2$ (68 mg, 0.3 mmol) in dry DMF (10 mL) was heated at 70-75° C. for 2.5 h. The cooled reaction mixture was diluted with ether (20 mL) and ice-water (20 mL), the aqueous phase was separated and extracted with ethyl acetate (3×20 mL). The combined organic phases were washed with water and brine, dried over Na$_2$SO$_4$ and concentrated in vacuo. Purification of the residue by chromatography on silica gel (petrol ether/EtOAc 8:1) gave 44 (731 mg, 62%) as a yellow solid.

$^1$H NMR (500 MHz, CDCl$_3$): δ -0.01 (s, 6H, 2 CH$_3$), 0.42 (s, 9H, Si(CH$_3$)$_3$), 0.85 (s, 9H, C(CH$_3$)$_3$), 3.09 (t, J=7.0 Hz, 2H, CH$_2$), 3.84 (t, J=7.0 Hz, 2H, CH$_2$), 7.36 (d, J=9.0 Hz, 1H, Ar—H), 8.07 (dd, J=2.0, 9.0 Hz, 1H, Ar—H), 8.28 (br s, 1H, Ar—H), 8.62 (d, J=2.5 Hz, 1H, Ar—H); MS: calcd for C$_{19}$H$_{32}$N$_2$NaO$_3$Si$_2$ [M+Na]$^+$: 415.18. found 415.10.

Synthesis of Intermediate 45

3-[3-(tert-Butyldimethylsilyloxy)propyl]-5-nitro-2-(trimethylsilyl)-1H-indole According to the procedure described for 44, a mixture of 2-iodo-4-nitroaniline (1.58 g, 6.00 mmol), tert-butyldimethyl[(5-(trimethylsilyl)pent-4-yn-1-yl)oxy]silane (2.60 g, 9.60 mmol), KOAc (2.94 g, 30.0 mmol), LiCl (254 mg, 6.00 mmol) and Pd(OAc)$_2$ (110 mg, 0.6 mmol) in dry DMF (16 mL) was heated at 70-75° C. for 2.5 h. Work-up and purification gave crude 45 (2.40 g) as a yellow solid.

$^1$H NMR (500 MHz, CDCl$_3$): δ 0.1 (s, 6H, 2 CH$_3$), 0.42 (s, 9H, Si(CH$_3$)$_3$), 0.94 (s, 9H, C(CH$_3$)$_3$), 1.86 (m, 2H, CH$_2$), 2.93 (t, J=8.0 Hz, 2H, CH$_2$), 3.74 (t, J=6.0 Hz, 2H, CH$_2$), 7.35 (d, J=9.0 Hz, 1H, Ar—H), 8.07 (dd, J=2.0, 9.0 Hz, 1H, Ar—H), 8.19 (br s, 1H, Ar—H), 8.57 (d, J=1.5 Hz, 1H, Ar—H); $^{13}$C NMR (125 MHz, CDCl$_3$): δ -5.3 (2C, 2 CH$_3$), -0.8 (3C, Si(CH$_3$)$_3$), 22.4 (3C, C(CH$_3$)$_3$), 26.0 (CH$_2$), 35.2 (CH$_2$), 62.7 (CH$_2$), 110.6, 116.4, 117.8, 128.4, 137.1, 141.0, 141.2 (Ar—C).

Synthesis of Intermediate 46

3-[4-(tert-Butyldimethylsilyloxy)butyl]-5-nitro-2-(trimethylsilyl)-1H-indole According to the procedure described for 44, a mixture of 2-iodo-4-nitroaniline (500 mg, 1.90 mmol), 43 (1.12 g, 3.94 mmol), KOAc (97 mg, 0.988 mmol), LiCl (80 mg, 1.89 mmol) and Pd(OAc)$_2$ (43 mg, 0.200 mmol) in dry DMF (40 mL) was heated at 70-75° C. for 2.5 h. Work-up and purification gave crude 46 (385 mg, 48%) as a yellow solid.

$^1$H-NMR (500 MHz, CDCl$_3$): δ 0.04 (s, 6H, TBS-Me-H), 0.41 (s, 9H, TMS-Me-H), 0.88 (s, 9H, TBS-tBu-H), 1.59-1.68 (m, 2H, H-3'), 1.69-1.75 (m, 2H, H-2'), 2.81-2.88 (m, 2H, H-1'), 3.66 (t, J=6.2 Hz, 2H, H-4'), 7.34-7.37 (m, 1H, H-7), 8.05-8.08 (m, 1H, H-6), 8.31 (s, 1H, NH), 8.55-8.56 (m, 1H, H-4); $^{13}$C-NMR (125 MHz, CDCl$_3$): δ -5.16 (TBS-Me-C), -0.60 (TMS-C), 18.43, 26.04, 26.06 (2C, C-1', TBS-tBu-C), 28.66 (C-2'), 33.33 (C-3'), 63.02 (C-4'), 110.79 (C-7), 116.57 (C-4), 117.87 (C-6), 128.41, 128.50 (2C, C-3, C-9), 137.27 (C-2), 141.21, 141.36 (2C, C-5, C-8); elemental analysis calcd (%) for C$_{21}$H$_{36}$N$_2$O$_3$Si$_2$ (420.69): C, 59.96; H, 8.62; N, 6.66. found: C, 59.85; H, 8.68; N, 6.28.

Synthesis of Intermediate 47

3-(2-Hydroxyethyl)-5-nitro-1H-indole

To a solution of 44 (220 mg, 0.560 mmol) in MeCN (5 mL) was added 48% aq. HF (0.75 mL, 20.7 mmol) in portions. The mixture was stirred at rt for 48 h, then cautiously basified with saturated aq. Na$_2$CO$_3$ and extracted with ethyl acetate. The combined organic phases were washed with brine, dried over Na$_2$SO$_4$ and concentrated. The residue was purified by silica gel chromatography (petrol ether/EtOAc 1:1 to 1:3) to afford 47 (101 mg, 88%) as yellow solid.

$^1$H NMR (500 MHz, CD$_3$OD): δ 3.02 (t, J=7.0 Hz, 2H, CH$_2$), 3.83 (t, J=7.0 Hz, 2H, CH$_2$), 7.30 (s, 1H, Ar—H), 7.43 (d, J=9.0 Hz, 1H, Ar—H), 8.02 (dd, J=2.0, 9.0 Hz, 1H, Ar—H), 8.57 (d, J=2.0 Hz, 1H, Ar—H).

Synthesis of Intermediate 48

3-(3-Hydroxypropyl)-5-nitro-1H-indole

According to the procedure described for 47, to a solution of crude 45 (2.40 g) in MeCN (25 mL) was added 48% aq. HF (2.5 mL) and the mixture was stirred at rt for 48 h. Work-up and purification yielded 48 (820 mg, 62% over two steps) as a yellow solid.

$^1$H NMR (500 MHz, CD$_3$OD): δ 1.93 (m, 2H, CH$_2$), 2.86 (t, J=8.0 Hz, 2H, CH$_2$), 3.64 (t, J=6.0 Hz, 2H, CH$_2$), 7.24 (s, 1H, Ar—H), 7.41 (d, J=9.0 Hz, 1H, Ar—H), 8.00 (dd, J=2.5, 9.0 Hz, 1H, Ar—H), 8.53 (d, J=2.0 Hz, 1H, Ar—H); $^{13}$C NMR (125 MHz, CDCl$_3$): δ 22.0 (CH$_2$), 34.3 (CH$_2$), 62.4 (CH$_2$), 112.2, 116.7, 117.7, 119.1, 126.5, 128.2, 141.2, 142.1 (Ar—C).

Synthesis of Intermediate 49

3-(4-Hydroxybutyl)-5-nitro-1H-indole

To a solution of 46 (371 mg, 0.884 mmol) in anhydrous THF (20 mL) was added TBAF (4.4 mL, 1 M in THF) at 0° C. under Argon. The solution was allowed to warm to r.t., and after 3.5 h, the solvent was removed under reduced pressure. Purification of the residue by silica gel chromatography (CH$_2$Cl$_2$, CH$_2$Cl$_2$/MeOH 5:1, gradient 0 to 75%) gave 49 (109 mg, 53%) as a yellow viscous oil.

$^1$H-NMR (500 MHz, MeOD): δ 1.59-1.67 (m, 2H, H-3'), 1.74-1.83 (m, 2H, H-2'), 2.78-2.84 (m, 2H, H-1'), 3.60 (t, J=6.5 Hz, 2H, H-4'), 7.23 (s, 1H, H-2), 7.38-7.43 (m, 1H, H-7), 7.97-8.02 (m, 1H, H-6), 8.49-8.52 (m, 1H, H-4); $^{13}$C-NMR (125 MHz, MeOD): δ 25.56 (C-1'), 27.78 (C-2'), 33.43 (C-3'), 62.80 (C-4'), 112.21 (C-7), 116.70 (C-4), 117.65 (C-6), 119.57 (C-3), 126.46 (C-2), 128.18 (C-9), 141.19 (C-8), 142.07 (C-5).

Synthesis of Intermediate 50

3-(2-Bromoethyl)-5-nitro-1H-indole

To a solution of 47 (91.5 mg, 0.443 mmol) in dry MeCN (10 mL) was added PPh$_3$ (175 mg, 0.665 mmol) followed by portion-wise addition of CBr$_4$ (221 mg, 0.665 mmol) at 0° C. under argon. The mixture was stirred at rt for 2 h, then diluted with ethyl acetate, washed with H$_2$O and brine and dried over Na$_2$SO$_4$. The solvents were evaporated and the residue was purified by silica gel chromatography (petrol ether/EtOAc 4:1 to 1:1) to give 50 (105 mg, 87%) as a yellow solid.

$^1$H NMR (500 MHz, DMSO-d6): δ 3.33 (t, J=7.0 Hz, 2H, CH$_2$), 3.77 (t, J=7.0 Hz, 2H, CH$_2$), 7.52-7.54 (m, 2H, Ar—H), 7.99 (dd, J=2.5, 9.0 Hz, 1H, Ar—H), 8.60 (d, J=2.0 Hz, 1H, Ar—H), 11.71 (s, 1H, Ar—H).

Synthesis of Intermediate 51

3-(3-Bromopropyl)-5-nitro-1H-indole

According to the procedure described for 50, to a solution of 48 (725 mg, 3.29 mmol) in MeCN (15 mL) was added PPh$_3$ (1.30 g, 4.94 mmol) and CBr$_4$ (1.638 g, 4.94 mmol) at 0° C. under argon. The mixture was stirred at rt for 2 h. Work-up and purification gave 51 (900 mg, 96%) as a yellow solid.

$^1$H NMR (500 MHz, CD$_3$OD): δ 2.23 (m, 2H, CH$_2$), 2.97 (t, J=7.0 Hz, 2H, CH2), 3.48 (t, J=6.5 Hz, 2H, CH$_2$), 7.29 (s, 1H, Ar—H), 7.44 (d, J=9.0 Hz, 1H, Ar—H), 8.03 (dd, J=2.0, 9.0 Hz, 1H, Ar—H), 8.55 (d, J=2.0 Hz, 1H, Ar—H); $^{13}$C NMR (125 MHz, CDCl$_3$): δ 24.0 (CH$_2$), 33.9 (CH$_2$), 34.5 (CH$_2$), 112.4, 116.6, 117.8, 117.8, 127.0, 128.0, 141.2, 142.3 (Ar—C).

Synthesis of Intermediate 52

3-(4-Bromobutyl)-5-nitro-1H-indole

According to the procedure described for 50, to a solution of 49 (100 mg, 0.427 mmol) in MeCN (3 mL) was added PPh$_3$ (135 mg, 0.515 mmol) and CBr$_4$ (180 mg, 0.543 mmol) at 0° C. under argon. The mixture was stirred at rt for 2 h. Work-up and purification gave 52 (108 mg, 85%) as a yellow solid.

$^1$H-NMR (500 MHz, CDCl$_3$): δ 1.85-1.93 (m, 2H, H-2'), 1.93-2.00 (m, 2H, H-3'), 2.83 (t, J=7.4 Hz, 2H, H-1'), 3.46 (t, J=6.6 Hz, 2H, H-4'), 7.14-7.18 (m, 1H, H-2), 7.36-7.42 (m, 1H, H-7), 8.08-8.13 (m, 1H, H-6), 8.44 (s, 1H, NH), 8.54-8.59 (m, 1H, H-4); $^{13}$C-NMR (125 MHz, CDCl$_3$): δ 24.17 (C-1'), 28.64 (C-2'), 32.55 (C-3'), 33.68 (C-4'), 111.20 (C-7), 116.44 (C-4), 117.89 (C-6), 118.96 (C-3), 124.39 (C-2), 127.08 (C-9), 139.45 (C-8), 141.63 (C-5); elemental analysis calcd (%) for C$_{12}$H$_{13}$BrN$_2$O$_2$ (297.15): C, 48.50; H, 4.41; N, 9.43. found C, 48.55/48.45; H, 4.52/4.54; N, 9.28/9.27.

Synthesis of Product 53

3-(2-Azidoethyl)-5-nitro-1H-indole

To a solution of 50 (240 mg, 0.89 mmol) in dry DMF (7 mL) was added NaN$_3$ (145 mg, 2.23 mmol) and 15-crown-5 (50 µl). The reaction mixture was stirred at rt for 16 h. The solvent was evaporated and the residue was purified by silica gel chromatography (petrol ether/EtOAc 3:1) to give 53 as yellow solid (202 mg, 98%).

$^1$H NMR (500 MHz, CDCl$_3$): δ 3.09 (t, J=7.0 Hz, 2H, CH$_2$), 3.62 (t, J=7.0 Hz, 2H, CH$_2$), 7.27 (d, J=2.0 Hz, 1H, Ar—H), 7.42 (d, J=9.0 Hz, 1H, Ar—H), 8.13 (dd, J=2.5, 9.0 Hz, 1H, Ar—H), 8.58 (d, J=2.0 Hz, 1H, Ar—H); $^{13}$C NMR (125 MHz, CDCl$_3$): δ 24.8 (CH$_2$), 51.4 (CH$_2$), 111.3, 115.1, 116.0, 117.9, 125.4, 126.7, 139.2, 141.7 (Ar—C); IR (KBr): 3409, 2101, 1507, 1468, 1326 cm$^{-1}$; HR-MS Calcd for C$_{10}$H$_9$N$_5$NaO$_2$ [M+Na]$^+$: 254.0654. Found 254.0654; elemental analysis calcd (%) for C$_{10}$H$_9$N$_5$O$_2$: C, 51.95; H, 3.92, N, 30.29. found: C, 52.07; H, 4.04; N, 30.15.

Synthesis of Product 54

3-(3-Azidopropyl)-5-nitro-1H-indole

According to the procedure described for 53, to a solution of 51 (900 mg, 3.17 mmol) in DMF (15 mL) was added NaN$_3$ (309 mg, 4.76 mmol) and 15-crown-5 (50 µL). The reaction mixture was stirred at rt for 16 h. Work-up and purification afforded 54 as a yellow solid (725 mg, 93%).

$^1$H NMR (500 MHz, CDCl$_3$): δ 2.98 (m, 2H, CH$_2$), 2.90 (t, J=7.5 Hz, 2H, CH$_2$), 3.36 (t, J=6.5 Hz, 2H, CH$_2$), 7.27 (s, 1H, Ar—H), 7.43 (d, J=9.0 Hz, 1H, Ar—H), 8.03 (dd, J=2.0, 9.0 Hz, 1H, Ar—H), 8.54 (d, J=2.0 Hz, 1H, Ar—H); $^{13}$C NMR (125 MHz, CDCl$_3$): δ 22.7 (CH$_2$), 30.6 (CH$_2$), 51.9 (CH$_2$), 112.4, 116.6, 117.8, 118.2, 126.8, 128.0, 141.2, 142.2 (Ar—C); HR-MS: calcd for C$_{11}$H$_{11}$N$_5$NaO$_2$ [M+Na]$^+$: 268.0810. found 268.0813.

Synthesis of Product 55

3-(4-Azidobutyl)-5-nitro-1H-indole

According to the procedure described for 53, to a solution of 52 (98 mg, 0.330 mmol) in DMF (5 mL) was added NaN$_3$ (108 mg, 1.66 mmol). The reaction mixture was stirred at rt for 16 h. Work-up and purification afforded 55 as a yellow solid (80 mg, 94%).

$^1$H-NMR (500 MHz, CDCl$_3$): δ 1.66-1.74 (m, 2H, H-3'), 1.78-1.87 (m, 2H, H-2'), 2.80-2.90 (m, 2H, H-1'), 3.31-3.38 (m, 2H, H-4'), 7.25-7.29 (m, 1H, H-2), 7.42-7.47 (m, 1H, H-7), 8.02-8.06 (m, 1H, H-6), 8.53-8.56 (m, 1H, H-4); $^{13}$C-NMR (125 MHz, CDCl$_3$): δ 25.26 (C-1'), 28.52 (C-2'), 29.66 (C-3'), 52.31 (C-4'), 112.28 (C-7), 116.65 (C-4), 117.72 (C-6), 119.15 (C-3), 126.56 (C-2), 128.10 (C-9, 141.21 (C-8), 142.14 (C-5); elemental analysis calcd (%) for C$_{12}$H$_{13}$N$_5$O$_2$ (259.26): C, 55.59; H, 5.05; N, 27.01. found: C, 55.68/55.75; H, 5.12/5.20; N 26.71/26.73. IR (KBr): ν=3413 (s), 2959 (vw), 2920 (w), 2858 (vw), 2090 (vs, N$_3$), 1619 (w), 1508 (m, NO$_2$), 1468 (m), 1328 (vs, N$_3$/NO$_2$), 1300 (m), 1262 (m), 1212 (w), 1107 (w), 1087 (m), 1073 (m), 897 (vw), 814 (w), 733 (w), 584 (vw), 541 (vw) cm$^{-1}$.

Example 3

Figure 6:
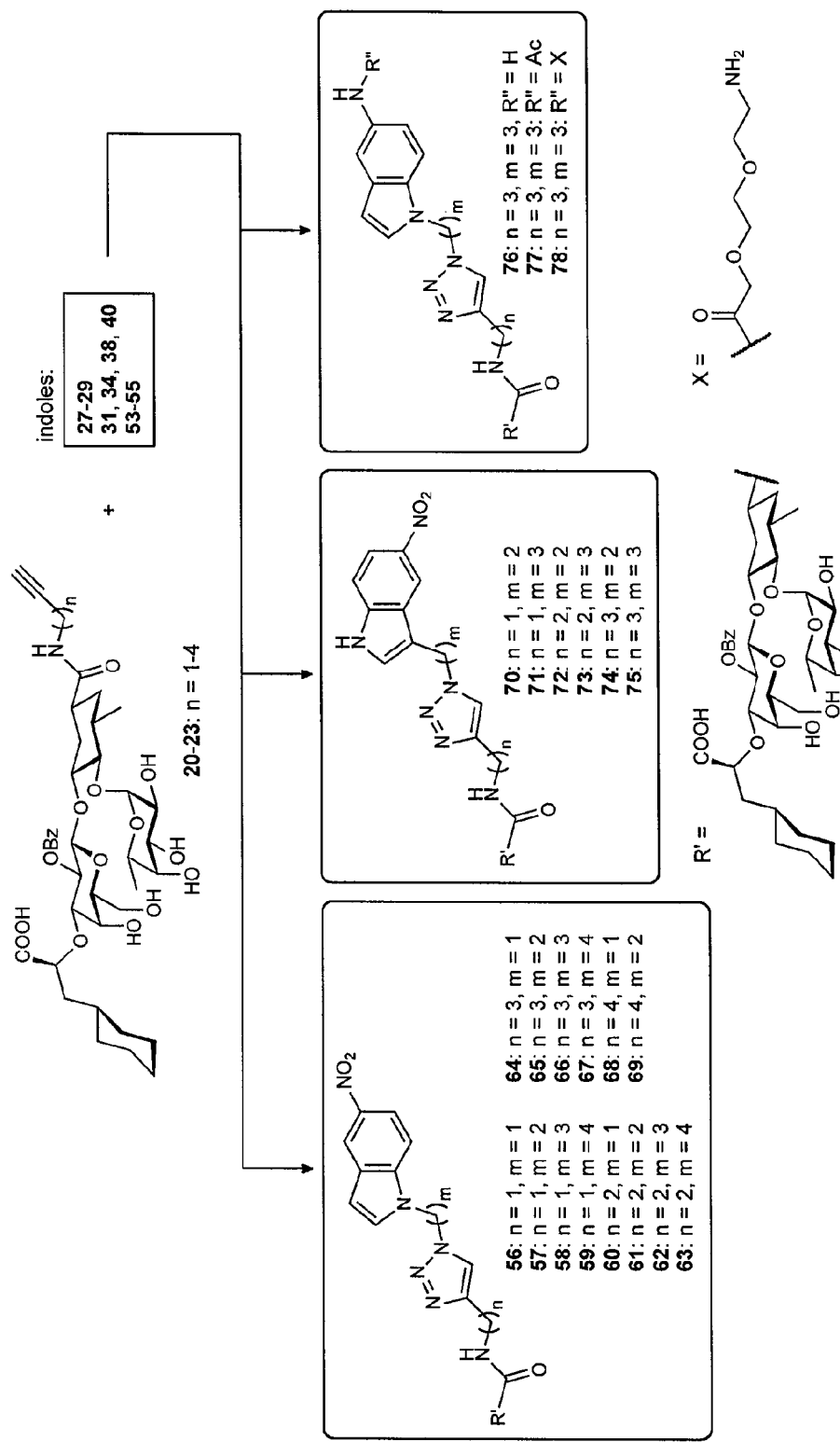
FIG. 6 is a diagram illustrating the synthesis of the selectin antagonists with triazole linker.

Synthesis of the Selectin Antagonists with Triazole Linker (FIG. 6)

General Procedure III for the Synthesis of Antagonists with Triazole Linker

Alkyne (1.0 equiv.) and azide (1.3 equiv.) were dissolved in $^t$BuOH/H$_2$O/THF 1:1:1 (approx. 0.015 M) under argon, and the solution was degassed in an ultrasound bath for 20 min. Degassed 0.1 M aq. Na-L-ascorbate (0.5 equiv.) and 0.1 M aq. CuSO$_4$.5H$_2$O (0.25 equiv.) were added, and the mixture was stirred at r.t. for 1-4 h until full conversion as indicated by MS. The solvent was removed in vacuo, the residue was redissolved in H$_2$O/MeCN 1:1+1-2 drops of Et$_3$N, filtrated (PTFE membrane filter) and purified by preparative HPLC-MS (H$_2$O/MeCN+0.1% HCOOH). All triazole inhibitors were isolated as yellow solids.

‡: chemical shift was obtained from HSQC spectrum
§: chemical shift was obtained from HMBC spectrum

Synthesis of Product 56

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[(6-nitro-1H-indol-3-yl)methyl]-1H-1,2,3-triazol-4-yl}methyl)cyclohexanecarboxamide Following general procedure III, alkyne 20 (8.4 mg, 10.8 µmol), azide 31 (3.6 mg, 16.6 µmol), Na-L-ascorbate (54 µL, 5.40 µmol) and CuSO$_4$.5H$_2$O (27 µL, 2.70 µmol) were dissolved in $^t$BuOH/H$_2$O/THF 1:1:1 (1 mL; no prior degassing). After 3 h, 10.1 mg (94%) of triazole 56 was isolated by preparative HPLC-MS.

$^1$H-NMR (500 MHz, MeOD): δ 0.49-0.60 (m, 1H, Cy), 0.61-0.73 (m, 3H, Cy), 0.85-0.97 (m, 1H, Cy), 1.06 (d, J=6.4 Hz, 3H, Me), 1.10-1.27 (m, 3H, Cy, H-6$_a$, H-2$_a$), 1.26-1.45 (m, 8H, Fuc H-6, 4Cy, Lac H-3$_a$), 1.46-1.65 (m, 4H, Lac H-3$_b$, H-6$_b$, Cy, H-5), 2.07-2.14 (m, 1H, H-2), 2.18-2.26 (m, 1H, H-1), 3.10 (t, J=9.6 Hz, 1H, H-4), 3.54 (t, J=5.8 Hz, 1H, Gal H-5), 3.59-3.68 (m, 2H, Gal H-3, H-3), 3.68-3.80 (m, 4H, Fuc H-2, Fuc H-4, 2Gal H-6), 3.85 (dd, J=3.2, 10.3 Hz, 1H, Fuc H-3), 3.93-3.97 (m, 1H, Gal H-4), 3.99-4.05 (m, 1H, Lac H-2), 4.30 (t, J=5.3 Hz, 2H, H-1'), 4.64 (d, J=8.0 Hz, 1H, Gal H-1), 4.92-5.00 (m, 2H, Fuc H-1, Fuc H-5), 5.42 (t, J=8.9 Hz, 1H, Gal H-2), 6.77-6.80 (m, 1H, Ind H-3), 6.84-6.84 (d, J=14.8 Hz, 1H, H-1"$_a$), 6.88 (d, J=14.8 Hz, 1H, H-1"$_b$), 7.37-7.43 (m, 2H, C$_6$H$_5$), 7.52-7.58 (m, 1H, C$_6$H$_5$), 7.71-7.74 (m, 1H, Ind H-2), 7.86-7.91 (m, 1H, Ind H-7), 8.02 (s, 3H, C$_6$H$_5$, H-3'), 8.11-8.16 (m, 1H, Ind H-6), 8.19 (t, J=5.4 Hz, 1H, CONH), 8.53-8.56 (m, 1H, Ind H-4); $^{13}$C-NMR (125 MHz, MeOD): δ 16.73 (Fuc C-6), 19.22 (Me), 26.55, 26.72, 27.29 (3C, Cy), 33.10, 34.19, 35.00 (3C, Cy), 35.09 (C-2), 35.45 (C-1'), 37.48 (C-6), 39.31 (C-5), 42.84 (Lac C-3), 42.95 (C-1), 59.70 (C-1"), 62.76 (Gal C-6), 67.71 (2C, Gal C-4, Fuc C-5), 70.28 (Fuc C-2), 71.39 (Fuc C-3), 72.98 (Gal C-2), 73.95 (Fuc C-4), 75.95 (Gal C-5), 78.25 (Lac C-2)‡, 79.70 (C-3), 83.00 (C-4), 83.69 (Gal C-3), 100.44 (Fuc C-1), 100.47 (Gal C-1), 106.81 (Ind C-3), 111.48 (Ind C-7), 118.74 (Ind C-6), 118.78 (Ind C-4), 123.94 (C-3'), 129.69 (C$_6$H$_5$), 130.10 (Ind C-9), 130.86 (C$_6$H$_5$), 131.52 (C$_6$H$_5$), 132.58 (Ind C-2), 134.33 (C$_6$H$_5$), 140.07 (Ind C-8), 143.86 (Ind C-5), 146.95 (C-2'), 166.85 (O(C=O)Ph), 176.93 (CONH), 179.38 (COOH); [a]$_D^{20}$=−58.0 (c=0.32, MeOH); HPLC (λ=350 nm): purity=95%, t$_R$=14.150 min; IR (KBr): ν=3430 (vs, OH), 2927 (s), 2846 (w), 1723 (s, C=O), 1648 (m, C=O), 1616 (w), 1584 (vw), 1520 (m), 1476 (vw), 1450 (m), 1403 (w), 1337 (vs, NO$_2$), 1314 (m), 1273 (s), 1226 (w), 1170 (w), 1114 (s), 1092 (s), 1073 (vs), 1040 (s), 999 (w), 966 (vw), 766 (w), 746 (w), 713 (m) cm$^{-1}$. cm$^{-1}$.

Synthesis of Product 57

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[2-(5-nitro-1H-indol-1-yl)ethyl]-1H-1,2,3-triazol-4-yl}methyl)cyclohexanecarboxamide Alkyne 20 (15.0 mg, 19.3 µmol), azide 27 (5.5 mg, 23.8 µmol), Na-L-ascorbate (approx. 1.9 mg, 9.59 µmol), and CuSO$_4$.5H$_2$O (1.9 mg, 7.61 µmol) were dissolved in $^t$BuOH/H$_2$O/THF 1:1:1 (1 mL) under argon (no degassing). After 2 h, triazole 57 (12.9 mg, 66%) was isolated according to general procedure III.

$^1$H-NMR (500 MHz, MeOD): δ 0.49-0.60 (m, 1H, Cy), 0.61-0.72 (m, 3H, Cy), 0.91 (d, J=11.6 Hz, 1H, Me), 1.12-1.25 (m, 3H, Cy, H-6$_a$, H-2$_a$), 1.25-1.37 (m, 7H, Fuc H-6, 4Cy), 1.37-1.45 (m, 1H, Lac H-3$_a$), 1.45-1.61 (m, 3H, Lac H-3$_b$, H-6$_b$, Cy), 1.61-1.71 (m, 1H, H-5), 2.06-2.14 (m, 1H, H-2), 2.20 (tt, J=3.1, 12.8 Hz, 1H, H-1), 3.14 (t, J=9.6 Hz, 1H, H-4), 3.59 (t, J=6.0 Hz, 1H, Gal H-5), 3.64 (dd, J=2.9, 9.7 Hz, 1H, Gal H-3), 3.66-3.82 (m, 5H, H-3, Fuc H-2, Fuc H-4, 2Gal H-6), 3.87 (dd, J=3.3, 10.3 Hz, 1H, Fuc H-3), 3.94-4.01 (m, 2H, Gal H-4, Lac H-2), 4.15-4.18 (m, 2H), 4.70 (d, J=8.1 Hz, 1H, Gal H-1), 4.75 (t, J=5.3 Hz, 2H, H-2"), 4.78-4.83 (m, 2H, H-1"), 4.97 (t, J=5.1 Hz, 2H, Fuc H-1, Fuc H-5), 5.43 (dd, J=8.3, 9.5 Hz, 1H, Gal H-2), 6.67-6.69 (m, 1H, Ind H-3), 7.15-7.21 (m, 1H, Ind H-7), 7.21-7.25 (m, 1H, Ind H-2), 7.37 (s, 1H, H-3'), 7.38-7.44 (m, 2H, C$_6$H$_5$), 7.54-7.60 (m, 1H, C$_6$H$_5$), 7.96-8.03 (m, 3H, Ind H-6, C$_6$H$_5$), 8.06 (t, J=5.3 Hz, 1H, CONH), 8.50-8.54 (m, 1H, Ind H-4); $^{13}$C-NMR (125 MHz, MeOD): δ 16.74 (Fuc C-6), 19.25 (Me), 26.54, 26.69, 27.27 (3C, Cy), 33.11, 34.17 (2C, Cy), 35.05 (C-2), 35.09 (C-1'), 35.32 (Cy), 37.51 (C-6), 39.31 (C-5), 42.81 (Lac C-3), 42.91 (C-1), 47.53 (C-2"), 51.43 (C-1"), 62.74 (Gal C-6), 67.72 (2C, Gal C-4, Fuc C-5), 70.32 (Fuc C-2), 71.41 (Fuc C-3), 72.99 (Gal C-2), 73.97 (Fuc C-4), 75.95 (Gal C-5), 78.09 (Lac C-2), 79.78 (C-3), 83.01 (C-4), 83.73 (Gal C-3), 100.46 (Fuc C-1), 100.52 (Gal C-1), 105.73 (Ind C-3), 110.25 (Ind C-7), 117.99 (Ind C-6), 118.71 (Ind C-4), 124.91 (C-3'), 129.18 (Ind C-9), 129.70 (C$_6$H$_5$), 130.88 (C$_6$H$_5$), 131.54 (C$_6$H$_5$), 132.55 (Ind C-2), 134.32 (C$_6$H$_5$), 140.46 (Ind C-8), 142.89 (Ind C-5), 146.55 (C-2'), 166.84 (O(C=O)Ph), 176.74 (CONH), 179.18 (COOH); HR-MS: m/z calcd for C$_{49}$H$_{64}$N$_6$O$_{17}$ [M+Na]$^+$: 1031.4220. found: 1031.4222. HPLC (µ=350 nm): purity=97%, t$_R$=14.483 min; [a]$_D^{20}$=−53.0 (c=1.09, MeOH); IR (KBr): ν=3435 (vs, OH), 2927 (m), 2852 (w), 1721 (m, C=O), 1643 (m, C=O), 1583 (w), 1516 (w), 1449 (w), 1402 (w), 1383 (w), 1335 (s, NO$_2$), 1272 (m). 1215 (vw), 1166 (w), 1111 (m), 1095 (m), 1073 (s), 1032 (m), 966 (vw), 897 (vw), 804 (vw), 776 (vw), 765 (vw), 744 (w), 713 (w) cm$^{-1}$.

Synthesis of Product 58

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[3-(5-nitro-1H-indol-1-yl)propyl]-1H-1,2,3-triazol-4-yl}methyl)cyclohexanecarboxamide Following general procedure III, alkyne 20 (12.0 mg, 15.4 µmol), azide 28 (5.7 mg, 23.2 µmol), Na-L-ascorbate (77 µL, 7.70 µmol), and CuSO$_4$.5H$_2$O (39 µL, 3.90 µmol) were dissolved in $^t$BuOH/H$_2$O/THF 1:1:1 (1 mL). After 3 h, triazole 58 (13.5 mg, 85%) was isolated by preparative HPLC-MS.

$^1$H-NMR (500 MHz, MeOD): δ 0.50-0.72 (m, 4H, Cy), 0.85-0.95 (m, 1H, Cy), 1.08 (d, J=6.4 Hz, 3H, Me), 1.13-1.25 (m, 3H, H, Cy, H-6$_a$, H-2$_a$), 1.24-1.37 (m, 7H, 4Cy, Fuc H-6), 1.37-1.44 (m, 1H, Lac H-3$_a$), 1.45-1.58 (m, 2H, Lac H-3$_b$, Cy), 1.58-1.71 (m, 2H, H-6$_b$, H-5), 2.13-2.19 (m, 1H, H-2$_b$), 2.25-2.33 (m, 1H, H-1), 2.47 (p, J=6.8 Hz, 2H, H-2"), 3.13 (t, J=9.5 Hz, 1H, H-4), 3.56 (t, J=5.8 Hz, 1H, Gal H-5), 3.61 (dd, J=2.5, 9.7 Hz, 1H, Gal H-3), 3.73 (qdd, J=5.7, 10.3, 11.7 Hz, 5H, H-3, Fuc H-2, Fuc H-4, 2Gal H-6), 3.86 (dd, J=3.3, 10.3 Hz, 1H, Fuc H-3), 3.95 (s, 1H, Gal H-4), 4.01 (d, J=7.9 Hz, 1H, Lac H-2), 4.31 (t, J=7.0 Hz, 2H, H-3"), 4.33 (s, 2H, H-1'), 4.39 (t, J=6.7 Hz, 2H, H-1"), 4.67 (d, J=8.0 Hz, 1H, Gal H-1), 4.93-4.99 (m, 2H, Fuc H-1, Fuc H-5), 5.40-5.45 (m, 1H, Gal H-2), 6.72-6.75 (m, 1H, Ind H-3), 7.38-7.45 (m, 3H, Ind H-7, C$_6$H$_5$), 7.46-7.50 (m, 1H, Ind H-2), 7.53-7.58 (m, 1H, C$_6$H$_5$), 7.75 (s, 1H, H-3'), 7.99-8.02 (m, 2H, C$_6$H$_5$), 8.05-8.09 (m, 1H, Ind H-6), 8.20-8.24 (m, 1H, CONH), 8.55-8.57 (m, 1H, Ind H-4); $^{13}$C-NMR (125 MHz, MeOD): δ 16.73 (Fuc C-6), 19.24 (Me), 26.53, 26.68, 27.26 (3C, Cy), 31.48 (C-2"), 33.12, 34.18 (2C, Cy), 35.04, 35.09 (2C, Cy, C-2), 35.64 (C-1'), 37.51 (C-6), 39.34 (C-5), 42.77 (Lac C-3), 43.03 (C-1), 44.50 (C-3"), 49.85 (C-1"), 62.76 (Gal C-6), 67.72, 67.75 (2C, Gal C-4, Fuc C-5), 70.31 (Fuc C-2), 71.41 (Fuc C-3), 72.98 (Gal C-2), 73.95 (Fuc C-4), 75.99 (Gal C-5), 77.98 (Lac C-2)‡, 79.75 (C-3), 83.03 (C-4), 83.71 (Gal C-3), 100.43 (Fuc C-1), 100.47 (Gal C-1), 105.24 (Ind C-3), 110.69 (Ind C-7), 117.94 (Ind C-6), 118.84 (Ind C-4), 124.44 (C-3'), 129.36 (Ind C-9), 129.68 ($C_6H_5$), 130.87 ($C_6H_5$), 131.55 ($C_6H_5$), 132.79 (Ind C-2), 134.30 ($C_6H_5$), 140.24 (Ind C-8), 142.85 (Ind C-5), 166.82 (O(C=O)Ph), 176.96 (CONH); HR-MS: m/z calcd for $C_{50}H_{66}N_6O_{17}$ [M+H]$^+$: 1023.4557. found: 1023.4561. $[α]_D^{20}$=−51.9 (c=1.15, MeOH); HPLC (λ=350 nm): purity=96%, $t_R$=14.317 min; IR (KBr): ν=3429 (vs, OH), 2928 (m), 2852 (w), 1723 (m, C=O), 1643 (m, CO), 1580 (vw), 1516 (m), 1479 (w), 1449 (w), 1402 (w), 1380 (w), 1335 (s, $NO_2$), 1269 (m), 1210 (w), 1163 (w), 1111 (m), 1070 (s), 1032 (m), 963 (w), 894 (vw), 768 (vw), 745 (w), 712 (w), 672 (w) cm$^{-1}$.

Synthesis of Product 59

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[4-(5-nitro-1H-indol-1-yl)butyl]-1H-1,2,3-triazol-4-yl}methyl)cyclohexanecarboxamide Following general procedure III, alkyne 20 (9.7 mg, 12.5 μmol), azide 29 (4.2 mg, 162 μmol), Na-L-ascorbate (124 μL, 12.4 μmol), and $CuSO_4·5H_2O$ (62 μL, 6.20 μmol) were dissolved in $^t$BuOH/$H_2O$/THF 1:1:1 (1 mL). After 1 h, triazole 59 (6.4 mg, 49%) was isolated by preparative HPLC-MS.

$^1$H-NMR (500 MHz, MeOD): δ 0.50-0.73 (m, 4H, Cy), 0.86-0.96 (m, 1H, Cy), 1.07 (d, J=6.4 Hz, 3H, Me), 1.17 (dt, J=12.5, 35.3 Hz, 3H, Cy, H-6$_a$, H-2$_a$), 1.32 (dd, J=8.9, 15.8 Hz, 7H, 4Cy, Fuc H-6), 1.38-1.45 (m, 1H, Lac H-3$_a$), 1.50 (ddd, J=3.9, 10.0, 13.8 Hz, 1H, Lac H-3), 1.54-1.69 (m, 3H, Cy, H-6, H-5), 1.77-1.93 (m, 4H, H-3", H-2"), 2.11-2.18 (m, 1H, H-2), 2.22-2.30 (m, 1H, H-1), 3.12 (t, J=9.5 Hz, 1H, H-4), 3.55 (t, J=5.8 Hz, 1H, Gal H-5), 3.62 (dd, J=2.9, 9.7 Hz, 1H, Gal H-3), 3.64-3.82 (m, 5H, H-3, Fuc H-2, Fuc H-4, 2Gal H-6), 3.86 (dd, J=3.3, 10.3 Hz, 1H, Fuc H-3), 3.95-3.97 (m, 1H, Gal H-4), 4.01 (dd, J=2.5, 9.6 Hz, 1H, Lac H-2), 4.26 (t, J=6.8 Hz, 2H, H-4"), 4.31 (s, 2H, H-1'), 4.39 (t, J=6.6 Hz, 2H, H-1"), 4.67 (d, J=8.1 Hz, 1H, Gal H-1), 4.94-4.99 (m, 2H, Fuc H-1, Fuc H-5), 5.40-5.45 (m, 1H, Gal H-2), 6.71 (d, J=3.2 Hz, 1H, Ind H-3), 7.41-7.47 (m, 3H, Ind H-7, $C_6H_5$), 7.50-7.54 (m, 1H, Ind H-2), 7.56-7.60 (m, 1H, $C_6H_5$), 7.72 (s, 1H, H-3'), 8.02-8.05 (m, 2H, $C_6H_5$), 8.05-8.09 (m, 1H, Ind H-6), 8.53-8.58 (m, 1H, Ind H-4); $^{13}$C-NMR (125 MHz, MeOD): δ 16.73 (Fuc C-6), 19.23 (Me), 26.54, 26.70, 27.28 (3C, Cy), 28.16, 28.48 (2C, C-2", C-3"), 33.13 (Cy), 34.20 (Cy), 35.06, 35.10 (2C, Cy, C-2), 35.58 (C-1'), 37.44 (C-6), 39.31 (C-5), 42.83 (Lac C-3), 42.97 (C-1), 46.81 (C-4"), 50.70 (C-1"), 62.78 (Gal C-6), 67.72, 67.76 (2C, Gal C-4, Fuc C-5), 70.31 (Fuc C-2), 71.41 (Fuc C-3), 73.00 (Gal C-2), 73.96 (Fuc C-4), 75.99 (Gal C-5), 78.29 (Lac C-2), 79.76 (C-3), 83.00 (C-4), 83.72 (Gal C-3), 100.43 (Fuc C-1), 100.50 (Gal C-1), 104.94 (Ind C-3), 110.76 (Ind C-7), 117.80 (Ind C-6), 118.81 (Ind C-4), 124.19 (C-3'), 129.27 (Ind C-9), 129.71 ($C_6H_5$), 130.89 ($C_6H_5$), 131.59 ($C_6H_5$), 132.79 (Ind C-2), 134.33 ($C_6H_5$), 140.77 (Ind C-8), 142.72 (Ind C-5), 146.16 (C-2'), 166.85 (O(C=O)Ph), 176.90 (CONH), 179.31 (COOH); HR-MS: m/z calcd for $C_{51}H_{68}N_6O_{17}$ [M−H+2Na]$^+$: 1081.4353. found: 1081.4342. $[α]_D^{20}$=−57.0 (c=0.62, MeOH); HPLC (λ=350 nm): purity=95%, $t_R$=14.633 min; IR (KBr): ν=3431 (vs, OH), 2927 (m), 2852 (m), 1725 (m, C=O), 1639 (m, C=O), 1580 (w), 1516 (m), 1479 (w), 1448 (w), 1402 (w), 1383 (w), 1334 (s, $NO_2$), 1271 (m), 1111 (m), 1071 (s), 1032 (m), 999 (vw), 966 (vw), 933 (vw), 897 (vw), 837 (vw), 804 (vw), 768 (vw), 746 (vw), 713 (w), 667 (vw), 593 (vw) cm$^{-1}$.

Synthesis of Product 60

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[(6-nitro-1H-indol-3-yl)methyl]-1H-1,2,3-triazol-4-yl}ethyl)cyclohexanecarboxamide Following general procedure III, alkyne 21 (10.4 mg, 13.1 μmol), azide 31 (4.3 mg, 19.8 μmol), Na-L-ascorbate (66 μL, 6.60μmol) and $CuSO_4·5H_2O$ (33 μL, 3.30 μmol) were dissolved in $^t$BuOH/$H_2O$/THF 1:1:1 (1 mL; no prior degassing). After 4 h, 8.8 mg (66%) of triazole 60 was isolated by preparative HPLC-MS.

$^1$H-NMR (500 MHz, MeOD): δ 0.49-0.59 (m, 1H, Cy), 0.59-0.71 (m, 3H, Cy), 0.85-0.99 (m, 2H, Cy, H-6$_a$), 1.02 (d, J=6.5 Hz, 3H, Me), 1.04-1.13 (m, 1H, H-2$_a$), 1.17-1.37 (m, 8H, Fuc H-6, 5Cy), 1.37-1.45 (m, 2H, Lac H-3$_a$, H-6), 1.46-1.62 (m, 3H, Lac H-3$_b$, H-5, Cy), 2.06-2.12 (m, 2H, H-2, H-1), 2.76 (t, J=7.0 Hz, 2H, H-2'), 3.08 (t, J=9.5 Hz, 1H, H-4), 3.55 (t, J=5.8 Hz, 1H, Gal H-5), 3.59-3.66 (m, 2H, Gal H-3, H-3), 3.69-3.81 (m, 4H, Fuc H-2, Fuc H-4, 2Gal H-6), 3.86 (dd, J=3.2, 10.3 Hz, 1H, Fuc H-3), 3.94-3.97 (m, 1H, Gal H-4), 3.98-4.03 (m, 1H, Lac H-2), 4.66 (d, I=8.0 Hz, 1H, Gal H-1), 4.93-5.01 (m, 2H, Fuc H-1, Fuc H-5), 5.43 (t, J=8.9 Hz, 1H, Gal H-2), 6.78 (d, J=14.8 Hz, 1H, H-1"$_a$), 6.80-6.82 (m, 1H, Ind H-3), 6.85 (d, J=14.7 Hz, 1H, H-1"$_b$), 7.41-7.46 (m, 2H, $C_6H_5$), 7.50-7.55 (m, 1H, $C_6H_5$), 7.65-7.68 (m, 1H, Ind H-2), 7.82-7.85 (m, 1H, H-4'), 7.87-7.90 (m, 1H, Ind H-7), 8.03-8.07 (m, 2H, $C_6H_5$), 8.14-8.18 (m, 1H, Ind H-6), 8.56-8.59 (m, 1H, Ind H-4); $^{13}$C-NMR (125 MHz, MeOD): δ 16.74 (Fuc C-6), 19.18 (Me), 26.41, 26.54, 26.72 (3C, 2Cy, C-2'), 27.28 (Cy), 33.11, 34.21 35.10 (Cy), 35.35 (C-2'), 37.26 (C-6), 39.24 (C-5), 39.66 (C-1'), 42.88, 43.08 (2C, Lac C-3, C-1), 59.63 (C-1"), 62.78 (Gal C-6), 67.71 (2C, Gal C-4, Fuc C-5), 70.31 (Fuc C-2), 71.42 (Fuc C-3), 73.05 (Gal C-2), 73.98 (Fuc C-4), 76.00 (Gal C-5), 78.33 (Lac C-2)‡, 79.87 (C-3), 82.91 (C-4), 83.69 (Gal C-3), 100.44 (Fuc C-1), 100.62 (Gal C-1), 106.92 (Ind C-3), 111.49 (Ind C-7), 118.78 (Ind C-6), 118.84 (Ind C-4), 123.30 (C-4'), 129.73 ($C_6H_5$), 130.06 (Ind C-9), 130.93 ($C_6H_5$), 131.62 ($C_6H_5$), 132.52 (Ind C-2), 134.36 ($C_6H_5$), 140.09 (Ind C-8), 143.89 (Ind C-5), 147.06 (C-3'), 166.81 (O(C=O)Ph), 176.99 (CONH), 179.82 (COOH)§; $[α]_D^{20}$=−67.5 (c=0.23, MeOH); HPLC (λ=350 nm): purity=95%, $t_R$=14.000 min; IR (KBr): ν=3429 (vs, OH), 2927 (s), 2853 (w), 1722 (s, C=O), 1648 (m, C=O), 1616 (w), 1584 (vw), 1520 (m), 1476 (vw), 1450 (m), 1403 (w), 1337 (vs, $NO_2$), 1317 (s), 1273 (s), 1224 (w), 1169 (w), 1114 (s), 1095 (s), 1073 (vs), 1034 (s), 1000 (vw), 966 (vw), 760 (vw), 746 (w), 713 (m) cm$^{-1}$.

Synthesis of Product 61

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[2-(5-nitro-1H-indol-1-yl)ethyl]-1H-1,2,3-triazol-4-yl}ethyl)cyclohexanecarboxamide Alkyne 21 (15.3 mg, 19.3 μmol), azide 27 (5.8 mg, 2.51μmol), Na-L-ascorbate (2.3 mg, 11.6 μmol), and CuSO$_4$.5H$_2$O (1.3 mg, 5.21μmol) were dissolved in $^t$BuOH/H$_2$O 1:1 (1 mL) under argon (no degassing). After 4 h, triazole 61 (15.7 mg, 79%) was isolated according to general procedure III.

$^1$H-NMR (500 MHz, MeOD): δ 0.49-0.61 (m, 1H, Cy), 0.61-0.73 (m, 3H, Cy), 0.83-0.96 (m, 1H, Cy), 1.09 (d, J=6.5 Hz, 3H, Me), 1.11-1.26 (m, 3H, H-2$_a$, H-6$_a$, Cy), 1.26-1.37 (m, 8H, 5Cy, 3Fuc H-6), 1.37-1.46 (m, 1H, Lac H-3$_a$), 1.45-1.61 (m, 3H Lac H-3$_b$, H-6, Cy), 1.60-1.70 (m, 1H, H-5), 2.06-2.13 (m, 1H, H-2), 2.13-2.22 (m, 1H, H-1), 2.61 (t, J=7.4 Hz, 2H, H-2'), 3.09-3.19 (m, 3H, H-1', H-4), 3.53-3.59 (m, 1H, Gal H-5), 3.59-3.83 (m, 6H, Gal H-3, H-3, Fuc H-2, Fuc H-4, 2Gal H-6), 3.87 (dd, J=3.3, 10.3 Hz, 1H, Fuc H-3), 3.91-4.00 (m, 2H, Gal H-4, Lac H-2), 4.68 (d, J=8.0 Hz, 1H, Gal H-1), 4.73-4.78 (m, 2H, H-2"), 4.78-4.82 (m, 2H, H-1"), 4.92-5.01 (m, 2H, Fuc H-1, Fuc H-5), 5.39-5.46 (m, 1H, Gal H-2), 6.70 (d, J=3.2 Hz, 1H, Ind H-3), 7.24-7.28 (m, 2H, Ind H-2, Ind H-7), 7.29 (s, 1H, H-4'), 7.40-7.46 (m, 2H, C$_6$H$_5$), 7.51-7.55 (m, 1H, C$_6$H$_5$), 7.67 (t, J=5.8 Hz, 1H, CONH), 7.97-8.01 (m, 1H, Ind H-6), 8.02-8.06 (m, 2H, C$_6$H$_5$), 8.49-8.54 (m, 1H, Ind H-4); $^{13}$C-NMR (125 MHz, MeOD): δ 16.72 (Fuc C-6), 19.25 (Me), 26.35 (C-2'), 26.53, 26.70 (2C, Cy), 27.27 (Cy), 33.15 (Cy), 34.22 (Cy), 35.07 (Cy), 35.31 (C-2), 37.38 (C-6), 39.29 (C-5), 40.03 (C-1'), 42.82 (Lac C-3), 43.20 (C-1), 47.50 (C-2"), 51.30 (C-1"), 62.78 (Gal C-6), 67.71, 67.77 (2C, Gal C-4, Fuc C-5), 70.33 (Fuc C-2), 71.43 (Fuc C-3), 73.04 (Gal C-2), 73.96 (Fuc C-4), 76.00 (Gal C-5), 79.84 (C-3), 82.99 (C-4), 83.66 (Gal C-3), 100.41 (Fuc C-1), 100.57 (Gal C-1), 105.73 (Ind C-3), 110.26 (Ind C-7), 117.96 (Ind C-6), 118.74 (Ind C-4), 124.34 (C-4'), 129.20 (Ind C-9), 129.69 (C$_6$H$_5$), 129.74 (C$_6$H$_5$), 130.89 (C$_6$H$_5$), 132.54 (Ind C-2), 134.32 (C$_6$H$_5$), 140.44 (Ind C-8), 142.97 (Ind C-5), 146.47 (C-3'), 166.82 (O(C=O)Ph), 176.94 (CONH); HR-MS: m/z calcd for C$_{50}$H$_{66}$N$_6$O$_{17}$ [M−H+2Na]$^+$: 1067.4202. found: 1067.4207. HPLC (λ=350 nm): purity=96%, t$_R$=14.500 min; [a]$_D^{20}$=−88.2 (c=0.29, MeOH); IR (KBr): v=3418 (s, OH), 2926 (s), 2853 (m), 1722 (s, C=O), 1648 (m, C=O), 1619 (m), 1583 (w), 1517 (s), 1479 (w), 1451 (m), 1404 (w), 1334 (vs, NO$_2$), 1290 (m), 1271 (w), 1223 (w), 1166 (m), 1112 (s), 1095 (s), 1071 (vs), 1032 (s), 967 (w), 999 (m), 935 (vw), 897 (vw), 809 (vw), 778 (w), 766 (w), 747 (m), 712 (s), 677 (w), 593 (w) cm$^{-1}$.

Synthesis of Product 62

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[3-(5-nitro-1H-indol-1-yl)propyl]-1H-1,2,3-triazol-4-yl}ethyl)cyclohexanecarboxamide Alkyne 21 (17.3 mg, 21.8μmol) and azide 28 (7.0 mg, 28.5 μmol) were dissolved in $^t$BuOH/H$_2$O/THF 1:1:1 (1 mL). The solution was degassed by 3 pump-freeze cycles, and the Na-L-ascorbate (110 μL, 11.0 μmol) and CuSO$_4$.5H$_2$O (55 μL, 5.50 μmol) solutions were added under argon. After 3 h, triazole 62 (14.4 mg, 63%) was isolated according to general procedure III.

$^1$H-NMR (500 MHz, MeOD): δ 0.49-0.74 (m, 4H, Cy), 0.83-0.97 (m, 1H, Cy), 1.05 (d, J=6.5 Hz, 3H, Me), 1.07-1.25 (m, 3H, H-2$_a$, H-6$_a$, Cy), 1.26-1.37 (m, 7H, Fuc H-6, 4Cy), 1.36-1.45 (m, 1H, Lac H-3$_a$), 1.45-1.58 (m, 3H, Lac H-3$_b$, H-6$_b$, Cy), 1.58-1.69 (m, 1H, H-5), 2.07-2.15 (m, 1H, H-2$_b$), 2.17-2.26 (m, 1H, H-1), 2.46 (p, J=6.6 Hz, 2H, H-2"), 2.79 (t, J=7.1 Hz, 2H, H-2'), 3.11 (t, J=9.6 Hz, 1H, H-4), 3.32-3.41 (m, 2H, H-1'), 3.54 (t, J=6.1 Hz, 1H, Gal H-5), 3.61 (dd, J=2.8, 9.8 Hz, 1H, Gal H-3), 3.63-3.82 (m, 6H, H-3, Fuc H-1, Fuc H-4, Gal H-6), 3.85 (dd, J=3.3, 10.3 Hz, 1H, Fuc H-3), 3.95 (d, J=2.5 Hz, 1H, Gal H-4), 3.97-4.03 (m, 1H, Lac H-2), 4.30 (t, J=6.9 Hz, 2H, H-3"), 4.37 (t, J=6.8 Hz, 2H, H-1"), 4.66 (d, J=8.0 Hz, 1H, Gal H-1), 4.93-5.00 (m, 2H, Fuc H-1, Fuc H-5), 5.42 (dd, J=8.2, 9.5 Hz, 1H, Gal H-2), 6.73 (d, J=3.0 Hz, 1H, Ind H-3), 7.41-7.53 (m, 4H, C$_6$H$_6$, Ind H-2, Ind H-7), 7.57 (m, 1H, C$_6$H$_6$), 7.68 (s, 1H, H-4'), 7.81 (t, J=5.3 Hz, 1H, CONH), 8.02-8.06 (m, 2H, C$_6$H$_6$), 8.06-8.10 (m, 1H, Ind H-6), 8.54-8.58 (m, 1H, Ind H-4); $^{13}$C-NMR (125 MHz, MeOD): δ 16.72 (Fuc C-6), 19.24 (Me), 26.53, 26.62, 26.71 (3C, 2 Cy, C-2'), 27.27 (Cy), 31.48 (C-2"), 33.15 (Cy), 34.22 (Cy), 35.07 (Cy), 35.26 (C-2), 37.52 (C-6), 39.31 (C-5), 39.94 (C-1'), 42.84 (Lac C-3), 43.23 (C-1), 44.60 (C-3"), [48.16 (C-1")], 62.80 (Gal C-6), 67.72, 67.77 (2C, Gal C-4, Fuc C-5), 70.33 (Fuc C-2), 71.42 (Fuc C-3), 73.04 (Gal C-2), 73.96 (Fuc C-4), 76.01 (Gal C-5), [77.78 (Lac C-1)], 79.77 (C-3), 82.98 (C-4), 83.69 (Gal C-3), 100.40 (Fuc C-1), 100.52 (Gal C-1), 105.21 (Ind C-3), 110.75 (Ind C-7), 117.92 (Ind C-6), 118.83 (Ind C-4), 123.83 (C-4'), 129.39 (Ind C-9), 129.72 (C$_6$H$_5$), 130.90 (C$_6$H$_5$), 131.62 (C$_6$H$_5$), 132.84 (Ind C-2), 134.34 (C$_6$H$_5$), 140.25 (Ind C-8), 142.90 (Ind C-5), [146.71 (C-3')], 166.81 (O(C=O)Ph), 177.01 (CONH); HR-MS: m/z calcd for C$_{51}$H$_{68}$N$_6$O$_{17}$ [−H+2Na]$^+$: 1081.4358. found: 1081.4360. HPLC (λ=350 nm): purity=95%, t$_R$=15.033 min; [a]$_D^{20}$=−60.4 (c=0.32, MeOH); IR (KBr): v=3431 (vs, OH), 2927 (s), 2852 (w), 1724 (s, C=O), 1644 (m, C=O), 1578 (w), 1516 (m), 1476 (w), 1451 (m), 1404 (w), 1334 (vs, NO$_2$), 1271 (s), 1220 (w), 1163 (m), 1109 (s), 1071 (vs), 1032 (s), 967 (w), 899 (vw), 807 (vw), 765 (w), 746 (m), 713 (m), 593 (w) cm$^{-1}$.

Synthesis of Product 63

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[4-(5-nitro-1H-indol-1-yl)butyl]-1H-1,2,3-triazol-4-yl}ethyl)cyclohexanecarboxamide Alkyne 21 (14.0 mg, 17.7 μmol), azide 29 (6.1 mg, 23.5 μmol), Na-L-ascorbate (approx. 5 mg, 25.2μmol), and CuSO$_4$.5H$_2$O (3.1 mg, 12.5 μmol) were dissolved in $^t$BuOH/H$_2$O/THF 1:1:1 (1 mL). After 4 h, triazole 63 (9.3 mg, 50%) was isolated according to general procedure III.

$^1$H-NMR (500 MHz, MeOD): δ 0.49-0.72 (m, 4H, Cy), 0.84-0.95 (m, 1H, Cy), 1.06 (d, J=6.5 Hz, 3H, Me), 1.08-1.26 (m, 3H, Cy, H-6$_a$, H-2$_a$), 1.26-1.36 (m, 7H, 4 Cy, H-6), 1.36-1.44 (m, 1H, Lac H-3), 1.46-1.59 (m, 3H, Lac H-3, H-6$_b$, Cy), 1.59-1.66 (m, 1H, H-5), 1.77-1.91 (m, 4H, H-3", H-2"), 2.09-2.15 (m, 1H, H-2$_b$), 2.19 (tt, J=3.1, 12.6 Hz, 1H, H-1), 2.76 (t, J=7.2 Hz, 2H, H-2'), 3.11 (t, J=9.6 Hz, 1H, H-4), 3.32 (m, 1H, H-1') 3.53-3.58 (m, 1H, Gal H-5), 3.61-3.81 (m, 6H, Gal H-3, H-3, Fuc H-2, Fuc H-4, 2 Gal H-6), 3.86 (dd, J=3.3, 10.3 Hz, 1H, Fuc H-3), 3.95 (d, J=2.3 Hz, 1H, Gal H-4), 4.03 (dd, J=2.8, 9.8 Hz, 1H, Lac H-1), 4.27 (t, J=6.7 Hz, 2H, H-1"), 4.36 (t, J=6.4 Hz, 2H, H-1"), 4.68 (d, J=8.1 Hz, 1H, Gal H-1), 4.94 (d, J=4.0 Hz, 1H, Fuc H-1), 4.98 (q, J=6.6 Hz, 1H, Fuc H-5), 5.43 (dd, J=8.3, 9.5 Hz, 1H, Gal H-2), 6.71 (dd, J=0.5, 3.2 Hz, 1H, Ind H—), 7.43-7.47 (m, 3H, C$_6$H$_5$, Ind H-2), 7.52-7.58 (m, 2H, Ind H-7, C$_6$H$_5$), 7.64 (s, 1H, H-4'), 8.03-8.09 (m, 2H, 2 C$_6$H$_5$, Ind H-6), 8.56 (m, 1H, Ind H-4); $^{13}$C-NMR (125 MHz, MeOD): δ 16.74 (Fuc C-6), 19.24 (Me), 26.53, 26.59, 26.70 (3C, 2 Cy, C-2', 27.27 (Cy), 28.11 (C-3"), 28.50 (C-2"), 33.12 (Cy), 34.18 (Cy), 35.05 (Cy), 35.27 (C-2), 37.46 (C-6), 39.31 (C-5), 39.97 (C-1'), 42.80 (Lac C-3), 43.22 (C-1), 46.85 (C-2"), 50.61 (C-1"), 62.75 (Gal C-6), 67.70, 67.74 (2C, Gal C-4, Fuc C-5), 70.31 (Fuc C-2), 71.42 (Fuc C-3), 73.02 (Gal C-2), 73.96 (Fuc C-4), 75.98 (Gal C-5), 78.07 (Lac C-2), 79.79 (C-3), 83.00 (C-4), 83.68 (Gal C-3), 100.43 (Fuc C-1), 100.51 (Gal C-1), 104.93 (Ind C-3), 110.78 (Ind C-7), 117.79 (Ind C-6), 118.84 (Ind C-4), 123.58 (C-4'), 129.29 (Ind C-9), 129.73 ($C_6H_5$), 130.91 ($C_6H_5$), 131.58 ($C_6H_5$), 132.88 (Ind C-2), 134.36 ($C_6H_5$), 140.24 (Ind C-8), 142.72 (Ind C-5), 146.35 (C-3'), 166.81 (O(C=O)Ph), 176.99 (CONH), 179.14 (COOH); HR-MS: m/z calcd for $C_{52}H_{70}N_6O_{17}$ [M+H]$^+$: 1051.4870. found: 1051.4868. HPLC ($\lambda$=350 nm): purity=97%, $t_R$=15.283 min; $[a]_D^{20}$=−60.1 (c=0.86, MeOH); IR (KBr): v=3414 (vs, OH), 2927 (s), 2852 (m), 1722 (s, C=O), 1648 (m, C=O), 1610 (w), 1580 (w), 1515 (m), 1479 (w), 1450 (m), 1404 (w), 1334 (vs), 1272 (s), 1215 (w), 1163 (m), 1112 (s), 1072 (vs), 1032 (s, $NO_2$), 967 (w), 897 (vw), 807 (vw), 768 (w), 747 (m), 713 (m), 675 (w), 628 (w), 593 (w) cm$^{-1}$.

Synthesis of Product 64

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[(5-nitro-1H-indol-1-yl)methyl]-1H-1,2,3-triazol-4-yl}propyl)cyclohexanecarboxamide Following general procedure III, alkyne 22 (9.7 mg, 12.0 μmol), azide 31 (3.9 mg, 18.0 μmol), Na-L-ascorbate (60 μL, 6.00 μmol) and $CuSO_4.5H_2O$ (30 μL, 3.00 μmol) were dissolved in $^tBuOH/H_2O/THF$ 1:1:1 (1 mL; no prior degassing). After 3 h, 7.5 mg (61%) of triazole 64 was isolated by preparative HPLC-MS.

$^1$H-NMR (500 MHz, MeOD): δ 0.49-0.59 (m, 1H, Cy), 0.59-0.71 (m, 4H, Cy), 0.85-0.95 (m, 1H, Cy), 1.09 (d, J=6.5 Hz, 3H, Me), 1.11-1.25 (m, 3H, Cy, H-$6_a$, H-$2_a$), 1.25-1.36 (m, 7H, Cy, Fuc H-6), 1.36-1.45 (m, 1H, Lac H-$3_a$), 1.45-1.60 (m, 3H, Lac H-$3_b$, Cy, H-$6_b$), 1.60-1.67 (m, 1H, H-5), 1.67-1.74 (m, 2H, H-2'), 2.07-2.13 (m, 1H, H-$2_b$), 2.17-2.25 (m, 1H, H-1), 2.60 (t, J=7.5 Hz, 2H, H-3'), 3.04-3.10 (m, 2H, H-1'), 3.13 (t, J=9.6 Hz, 1H, H-4), 3.56 (t, J=5.9 Hz, 1H, Gal H-5), 3.62-3.81 (m, 6H, Gal H-3, H-3, Fuc H-2, Fuc H-4, Gal H-6), 3.86 (dd, J=3.2, 10.3 Hz, 1H, Fuc H-3), 3.96 (d, J=2.5 Hz, 1H, Gal H-4), 4.02 (d, J=6.9 Hz, 1H, Lac H-2), 4.66 (d, J=8.0 Hz, 1H, Gal H-1), 4.95-5.00 (m, 2H, Fuc H-1, Fuc H-5), 5.39-5.44 (m, 1H, Gal H-2), 6.79-6.82 (m, 1H, Ind H-3), 6.85 (s, 2H, H-1"), 7.24-7.29 (m, 2H, $C_6H_5$), 7.30-7.35 (m, 1H, $C_6H_5$), 7.69-7.76 (m, 2H, CONH, Ind H-2), 7.88-7.92 (m, 1H, Ind H-7), 7.94 (s, 1H, H-5'), 7.96-7.99 (m, 2H, $C_6H_5$), 8.13-8.17 (m, 1H, Ind H-6), 8.55-8.56 (m, 1H, Ind H-4); $^{13}$C-NMR (125 MHz, MeOD): δ 16.70 (Fuc C-6), 19.24 (Me), 23.46 (C-3'), 26.52 (Cy), 26.70 (Cy), 27.26 (Cy), 30.12 (C-2'), 33.12 (Cy), 34.19 (Cy), 35.05 (Cy), 35.52 (C-2), 37.38 (C-6), 39.30, 39.42 (2C, C-5, C-1'), 42.78 (Lac C-3), 43.37 (C-1), 59.70 (C-1"), 62.77 (Gal C-6), 67.71, 67.76 (2C, Gal C-4, Fuc C-5), 70.33 (Fuc C-2), 71.42 (Fuc C-3), 73.04 (Gal C-2), 73.97 (Fuc C-4), 75.99 (Gal C-5), 78.28 (Lac C-2)‡, 79.91 (C-3), 82.98 (C-4), 83.61 (Gal C-3), 100.45 (Fuc C-1), 100.63 (Gal C-1), 106.81 (Ind C-3), 111.47 (Ind C-7), 118.80, 118.81 (2C, Ind C-4, Ind C-6), 123.10 (C-5'), 129.58 (Ind C-9), 130.11 ($C_6H_5$), 130.76 ($C_6H_5$), 131.48 ($C_6H_5$), 132.58 (Ind C-2), 134.21 ($C_6H_5$), 140.11 (Ind C-8), 143.89 (Ind C-5), 149.16 (C-4'), 166.76 (O(C=O)Ph), 177.05 (CONH); HR-MS: m/z calcd for $C_{50}H_{66}N_6O_{17}$ [M+Na]$^+$: 1045.4377. found: 1045.4376; $[a]_D^{20}$=−42.3 (c=0.72, MeOH).

Synthesis of Product 65

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[2-(5-nitro-1H-indol-1-yl)ethyl]-1H-1,2,3-triazol-4-yl}propyl)cyclohexanecarboxamide Following general procedure III, alkyne 22 (14.6 mg, 18.1 μmol), azide 27 (5.5 mg, 23.8 μmol), Na-L-ascorbate (91 μL, 9.10 μmol) and $CuSO_4.5H_2O$ (45 μL, 4.50 μmol) were dissolved in $^tBuOH/H_2O/MeCN$ 1:1 (0.8 mL) and MeCN (0.1 mL). As no product could be detected after 1 h, further 91 μL and 45 μL of the Na-L-ascorbate and $CuSO_4.5H_2O$ solution were added. After another 18 h, triazole 65 (12.8 mg, 68%) was isolated by preparative HPLC-MS.

$^1$H-NMR (500 MHz, MeOD): δ 0.48-0.59 (m, 1H, Cy), 0.59-0.70 (m, 3H, Cy), 0.84-0.93 (m, 1H, Cy), 1.11 (d, J=6.5 Hz, 3H, Me), 1.14-1.36 (m, 10H, Cy, H-$6_a$, H-$2_a$, 4Cy, Fuc H-6), 1.36-1.44 (m, 1H, Lac H-$3_a$), 1.44-1.54 (m, 3H, Lac H-$3_b$, H-2'), 1.54-1.62 (m, 2H, Cy, H-$6_b$), 1.62-1.72 (m, 1H, H-5), 2.12-2.18 (m, 1H, H-$2_b$), 2.19-2.27 (m, 1H, H-1), 2.47 (t, J=7.4 Hz, 2H, H-3'), 2.86-2.93 (m, 2H, H-1'), 3.15 (t, J=9.6 Hz, 1H, H-4), 3.59 (t, J=5.8 Hz, 1H, Gal H-5), 3.65 (dd, J=2.7, 9.7 Hz, 1H, Gal H-3), 3.67-3.82 (m, 5H, H-3, Fuc H-2, Fuc H-4, 2Gal H-6), 3.88 (dd, J=3.3, 10.3 Hz, 1H, Fuc H-3), 3.94-3.99 (m, 2H, Gal H-4, Lac H-2), 4.72-4.78 (m, 3H, Gal H-1, H-2"), 4.79-4.83 (m, 2H, H-1"), 4.95-5.02 (m, 2H, Fuc H-1, Fuc H-5), 5.43 (dd, J=8.4, 9.3 Hz, 1H, Gal H-2), 6.69-6.71 (m, 1H, Ind H-3), 7.15-7.19 (m, 1H, Ind H-7), 7.21 (s, 1H, H-5'), 7.31-7.34 (m, 1H, Ind H-2), 7.35-7.39 (m, 2H, $C_6H_5$), 7.49-7.54 (m, 1H, $C_6H_5$), 7.94-7.97 (m, 1H, Ind H-6), 8.01-8.04 (m, 2H, $C_6H_5$), 8.48-8.52 (m, 1H, Ind H-4); $^{13}$C-NMR (125 MHz, MeOD): δ 16.73 (Fuc C-6), 19.27 (Me), 23.28 (C-3'), 26.54, 26.71, 27.30 (3C, Cy), 30.26 (C-2'), 33.11, 34.24, 35.13 (3C, Cy), 35.38 (C-2), 37.49 (C-6), 39.31, 39.36 (2C, C-5, C-1'), 42.98 (Lac C-3), 43.32 (C-1), 47.51 (C-2"), 51.46 (C-1"), 62.87 (Gal C-6), 67.73, 67.76 (2C, Gal C-4, Fuc C-5), 70.34 (Fuc C-2), 71.42 (Fuc C-3), 73.02 (Gal C-2), 73.97 (Fuc C-4), 76.03 (Gal C-5), 78.78 (Lac C-2)$^1$, 79.85 (C-3), 83.05 (C-4), 83.72 (Gal C-3), 100.44 (Fuc C-1), 100.56 (Gal C-1), 105.87 (Ind C-3), 110.18 (Ind C-7), 117.98 (Ind C-6), 118.73 (Ind C-4), 124.12 (C-5'), 129.11 (Ind C-9), 129.65 ($C_6H_5$), 130.85 ($C_6H_5$), 131.62 ($C_6H_5$), 132.46 (Ind C-2), 134.25 ($C_6H_5$), 140.57 (Ind C-8), 142.88 (Ind C-5), 148.44 (C-4'), 166.82 (O(C=O)Ph), 176.99 (CONH), 180.71 (COOH); HR-MS: m/z calcd for $C_{51}H_{68}N_6O_{17}$ [M+H]$^+$: 1037.4714. found: 1037.4711. HPLC ($\lambda$=350 nm): purity=96%, $t_R$=14.583 min; $[\alpha]_D$=−51.0 (c=0.89, MeOH); IR (KBr): v=3421 (s, OH), 2927 (m), 2852 (w), 1718 (m, C=O), 1646 (m, C=O), 1638 (m), 1620 (m), 1580 (w), 1517 (m), 1476 (w), 1429 (w), 1402 (w), 1383 (w), 1336 (vs, $NO_2$), 1270 (m), 1218 (w), 1166 (w), 1095 (s), 1070 (s), 1029 (s), 996 (m), 966 (w), 933 (vw), 894 (vw), 826 (vw), 809 (vw), 779 (vw), 771 (vw), 746 (w), 712 (w), 675 (vw), 589 (vw) cm$^{-1}$.

Synthesis of Product 66

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[3-(5-nitro-1H-indol-1-yl)propyl]-1H-1,2,3-triazol-4-yl}propyl)cyclohexanecarboxamide Alkyne 22 (106 mg, 132 μmol) and azide 28 (48.0 mg, 196 μmol) were dissolved in $^tBuOH/H_2O/THF$ 1:1:1 (8 mL), and the 0.1 M Na-L-ascorbate (658 µL, 65.8 µmol) and CuSO$_4$.5H$_2$O (329 µL, 32.9µmol) solutions were added under argon. After 40 min, the THF was removed under reduced pressure, and the residue was subjected to RP-18 silica gel chromatography (MeOH in H$_2$O, linear gradient, 0 to 95%). The product fractions were concentrated and further purified by preparative HPLC-MS (H$_2$O/MeCN+0.1% HCOOH) to afford triazole 66 (125 mg, 91%).

$^1$H-NMR (500 MHz, MeOD): δ 0.46-0.70 (m, 4H, Cy), 0.81-0.93 (m, 1H, Cy), 1.11 (d, J=6.5 Hz, 3H, Me), 1.14-1.36 (m, 10H, H-2$_a$, H-6$_a$, 5Cy, Fuc H-6), 1.36-1.44 (m, 1H, Lac H-3$_a$), 1.44-1.50 (m, 1H, Lac H-3$_b$), 1.50-1.57 (m, 1H, Cy), 1.60 (dd, J=2.5, 13.2 Hz, 1H, H-6$_b$), 1.63-1.71 (m, 1H H-5), 1.71-1.81 (m, 2H, H-2'), 2.10-2.19 (m, 1H, H-2$_b$), 2.25 (ddd, J=3.2, 8.0, 12.7 Hz, 1H, H-1), 2.49 (p, J=6.8 Hz, 2H, H-2"), 2.65 (t, J=7.4 Hz, 2H, H-3'), 3.05-3.19 (m, 3H, H-1', H-4), 3.57 (t, J=6.1 Hz, 1H, Gal H-5), 3.64 (dd, J=3.0, 9.7 Hz, 1H, Gal H-3), 3.66-3.83 (m, 5H, H-3, Fuc H-2, Fuc H-4, Gal H-6), 3.87 (dd, J=3.3, 10.3 Hz, 1H, Fuc H-3), 3.96 (d, J=2.4 Hz, 1H, Gal H-4), 4.00 (dd, J=2.9, 9.8 Hz, 1H, Lac H-2), 4.32 (t, J=6.9 Hz, 2H, H-3"), 4.40 (t, J=6.7 Hz, 2H, H-1"), 4.70 (d, J=8.1 Hz, 1H, Gal H-1), 4.95-5.01 (m, 2H, Fuc H-1, Fuc H-5), 5.43 (dd, J=8.2, 9.6 Hz, 1H, Gal H-2), 6.71-6.73 (m, 1H, Ind H-3), 7.34-7.38 (m, 2H, C$_6$H$_5$), 7.44-7.52 (m, 3H, Ind H-7, Ind H-2, C$_6$H$_5$), 7.65 (s, 1H, H-5'), 7.98-8.02 (m, 2H, C$_6$H$_5$), 8.04-8.08 (m, 1H, Ind H-6), 8.55-8.56 (m, 1H, Ind H-4); $^{13}$C-NMR (125 MHz, MeOD): δ 16.73 (Fuc C-6), 19.26 (Me), 23.54 (C-3'), 26.50, 26.67, 27.25 (3C, Cy), 30.22 (C-2'), 31.41 (C-2"), 33.11, 34.18, 35.04 (3C, Cy), 35.42 (C-2), 37.50 (C-6), 39.35, 39.48 (2C, C-5, C-1'), 42.82 (Lac C-3), 43.35 (C-1), 44.64 (C-3"), 48.56 (C-1"), 62.79 (Gal C-6), 67.71, 67.77 (2C, Gal C-4, Fuc C-5), 70.33 (Fuc C-2), 71.42 (Fuc C-3), 73.00 (Gal C-2), 73.96 (Fuc C-4), 75.99 (Gal C-5), 78.32 (Lac C-2), 79.85 (C-3), 83.03 (C-4), 83.67 (Gal C-3), 100.45 (Fuc C-1), 100.54 (Gal C-1), 105.21 (Ind C-3), 110.70 (Ind C-7), 117.90 (Ind C-6), 118.83 (Ind C-4), 123.54 (C-5'), 129.36 (Ind C-9), 129.65 (C$_6$H$_5$), 130.83 (C$_6$H$_5$), 131.56 (C$_6$H$_5$), 132.81 (Ind C-2), 134.26 (C$_6$H$_5$), 140.24 (Ind C-8), 142.83 (Ind C-5), 148.51 (C-4'), 166.78 (O(C=O)Ph), 177.04 (CONH), 179.26 (COOH); HR-MS: m/z calcd for C$_{52}$H$_{70}$N$_6$O$_{17}$ [M+Na]$^+$: 1073.4690. found: 1073.4684. [a]$_D^{20}$=−53.1 (c=0.99, MeOH); HPLC (λ=350 nm): purity=97%, t$_R$=14.267 min; IR (KBr): ν=3433 (vs, OH), 2926 (m), 2852 (w), 1725 (m, C=O), 1638 (m, C=O), 1514 (w), 1449 (w), 1402 (w), 1383 (w), 1334 (m, NO$_2$), 1268 (m), 1213 (w), 1163 (w), 1111 (m), 1070 (s), 1032 (m), 996 (w), 963 (vw), 933 (vw), 897 (vw), 807 (vw), 777 (vw), 744 (w), 712 (w) cm$^{-1}$.

Synthesis of Product 67

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[4-(5-nitro-1H-indol -1-yl)butyl]-1H-1,2,3-triazol-4-yl}propyl)cyclohexanecarboxamide Following general procedure III, alkyne 21 (12.0 mg, 14.9 µmol) and azide 29 (5.8 mg, 22.4 µmol), Na-L-ascorbate (74 µL, 7.40 µmol), and CuSO$_4$.5H$_2$O (36 µL, 3.70 µmol) were dissolved in $^t$BuOH/H$_2$O/THF 1:1:1 (1 mL). After 2 h, triazole 67 (9.4 mg, 59%) was isolated by preparative HPLC-MS.

$^1$H-NMR (500 MHz, MeOD): δ 0.49-0.70 (m, 4H, Cy), 0.83-0.94 (m, 1H, Cy), 1.10 (d, J=6.4 Hz, 3H, Me), 1.14-1.37 (m, 10H, H-2$_a$, H-6$_a$, $_{Cy}$, 4Cy, Fuc H-6), 1.40 (dd, J=9.1, 11.8 Hz, 1H, Lac H-3$_a$), 1.45-1.62 (m, 3H, Lac H-3$_b$, Cy, H-6$_b$), 1.62-1.70 (m, 1H, H-5), 1.70-1.78 (m, 2H, H-2'), 1.78-1.93 (m, 4H, H-3", H-2"), 2.11-2.18 (m, 1H, H-2$_b$), 2.21-2.29 (m, 1H, H-1), 2.63 (t, J=7.4 Hz, 2H, H-3'), 3.03-3.19 (m, 3H, H-1', H-4), 3.57 (t, J=5.9 Hz, 1H, Gal H-5), 3.64 (dd, J=2.8, 9.7 Hz, 1H, Gal H-3), 3.66-3.83 (m, 5H, H-3, Fuc H-2, Fuc H-4, Gal H-6), 3.87 (dd, J=3.2, 10.3 Hz, 1H, Fuc H-3), 3.95-4.03 (m, 2H, Gal H-4, Lac H-2), 4.28 (t, J=6.8 Hz, 2H, H-4"), 4.38 (t, J=6.6 Hz, 2H, H-1"), 4.70 (d, J=8.0 Hz, 1H, Gal H-1), 4.95-5.02 (m, 2H, Fuc H-1, Fuc H-5), 5.40-5.45 (m, 1H, Gal H-2), 6.68-6.72 (m, J=2.8 Hz, 1H, Ind H-3), 7.33-7.40 (m, 2H, C$_6$H$_5$), 7.42-7.46 (m, 1H, Ind H-2), 7.46-7.54 (m, 2H, C$_6$H$_5$, Ind H-7), 7.63 (s, 1H, H-5'), 7.98-8.04 (m, 2H, C$_6$H$_5$), 8.04-8.08 (m, 1H, Ind H-6), 8.53-8.57 (m, 1H, Ind H-4); $^{13}$C-NMR (125 MHz, MeOD): δ 16.73 (Fuc C-6), 19.26 (Me), 23.53 (C-3'), 26.52, 26.69, 27.27 (3C, Cy), 28.11, 28.47 (2C, C-2", C-3"), 30.23 (C-2'), 33.12, 34.20, 35.07 (3C, Cy), 35.44 (C-2), 37.48 (C-6), 39.34, 39.45 (2C, C-5, C-1'), 42.86 (2C, C-5, C-1'), 43.34 (C-1), 46.87 (C-2"), 50.61 (C-1"), 62.81 (Gal C-6), 67.71, 67.76 (2C, Gal C-4, Fuc C-5), 70.33 (Fuc C-2), 71.42 (Fuc C-3), 73.02 (Gal C-2), 73.97 (Fuc C-4), 76.00 (Gal C-5), 78.36 (Lac C-2), 79.87 (C-3), 83.01 (C-4), 83.67 (Gal C-3), 100.44 (Fuc C-1), 100.58 (Gal C-1), 104.90 (Ind C-3), 110.78 (Ind C-7), 117.78 (Ind C-6), 118.82 (Ind C-4), 123.35 (C-5'), 129.31 (Ind C-9), 129.65 (C$_6$H$_5$), 130.83 (C$_6$H$_5$), 131.57 (C$_6$H$_5$), 132.89 (Ind C-2), 134.26 (C$_6$H$_5$), 140.26 (Ind C-8), 142.71 (Ind C-5), 148.45 (C-4'), 166.78 (O(C=O)Ph), 177.03 (CONH), 179.61 (COOH); HR-MS: m/z calcd for C$_{53}$H$_{72}$N$_6$O$_{17}$ [M+Na]$^+$: 1087.4846. found: 1087.4848. [a]$_D^{20}$=−53.1° (c=0.82, MeOH); HPLC (λ=350 nm): purity=99%, t$_R$=14.517 min; IR (KBr): ν=3436 (vs, OH), 2926 (w), 2852 (vw), 1723 (w, C=O), 1632 (m, C=O), 1512 (w), 1451 (w), 1383 (w), 1334 (m, NO$_2$), 1270 (m), 1210 (vw), 1166 (vw), 1111 (m), 1070 (m), 1032 (m), 996 (vw), 966 (vw), 744 (w), 711 (w) cm$^{-1}$.

Synthesis of Product 68

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(4-{1-[(6-nitro-1H-indol -3-yl)methyl]-1H-1,2,3-triazol-4-yl}butyl)cyclohexanecarboxamide Following general procedure III, alkyne 23 (10.6 mg, 13.4µmol), azide 31 (4.4 mg, 20.3 µmol), Na-L-ascorbate (67 µL, 6.70 µmol) and CuSO$_4$.5H$_2$O (34 µL, 3.40 µmol) were dissolved in $^t$BuOH/H$_2$O/THF 1:1:1 (1 mL; no prior degassing). After 2 h, 11.3 mg (81%) of triazole 68 was isolated by preparative HPLC-MS.

$^1$H-NMR (500 MHz, MeOD): δ 0.47-0.70 (m, 4H, Cy), 0.83-0.94 (m, 1H, Cy), 1.08 (d, J=6.4 Hz, 3H, Me), 1.11-1.24 (m, 3H, Cy, H-6$_a$, H-2$_a$), 1.25-1.32 (m, 4H, Cy), 1.34 (d, J=6.5 Hz, 3H, Fuc H-6), 1.37-1.68 (m, 9H, Lac H-3$_a$, Lac H-3$_b$, H-2', H-6, H-3', H-5, Cy), 2.06-2.13 (m, 1H, H-2$_b$), 2.16-2.24 (m, 1H, H-1), 2.66 (t, J=7.5 Hz, 2H, H-4'), 3.06 (t, J=7.0 Hz, 2H, H-1'), 3.13 (t, J=9.6 Hz, 1H, H-4), 3.58 (t, J=5.9 Hz, 1H, Gal H-5), 3.63-3.70 (m, 2H, Gal H-3, H-3), 3.75 (s, 4H, Fuc H-2, Fuc H-4, 2Gal H-6), 3.86 (dd, J=3.2, 10.3 Hz, 1H, Fuc H-3), 3.96 (d, J=2.0 Hz, 1H, Gal H-4), 4.02 (dd, J=2.5, 9.7 Hz, 1H, Lac H-2), 4.69 (d, J=8.0 Hz, 1H, Gal H-1), 4.95-5.02 (m, 3H, Fuc H-1, Fuc H-5), 5.43 (t, J=8.9 Hz, 1H, Gal H-2), 6.78-6.81 (m, 1H, Ind H-3), 6.83 (s, 2H, H-1"), 7.36-7.41 (m, 2H, C$_6$H$_5$), 7.51-7.56 (m, 1H, C$_6$H$_5$), 7.70-7.74 (m, 1H, Ind H-2), 7.86-7.90 (m, 1H, Ind H-7), 7.95 (s, 1H, H-6'), 7.99-8.03 (m, 2H, C$_6$H$_5$), 8.12-8.17 (m, 1H, Ind H-6), 8.54-8.57 (m, 1H, Ind H-4); $^{13}$C (125 MHz, MeOD): δ 16.74 (Fuc C-6), 19.24 (Me), 25.67 (C-4'), 26.51, 26.67, 27.24 (3C, Cy), 27.43 (C-3'), 29.67 (C-2'), 33.08 (Cy), 34.13 (Cy), 35.03 (Cy), 35.38 (C-2), 37.46 (C-6), 39.32 (C-5), 39.75 (C-1'), 42.75 (Lac C-3), 43.31 (C-1), 59.65 (C-1"), 62.73 (Gal C-6), 67.70, 67.75 (2C, Gal C-4, Fuc C-5), 70.30 (Fuc C-2), 71.41 (Fuc C-3), 73.00 (Gal C-2), 73.96 (Fuc C-4), 75.95 (Gal C-5), 77.96 (Lac C-2), 79.82 (C-3), 83.02 (C-4), 83.63 (Gal C-3), 100.45 (Fuc C-1), 100.50 (Gal C-1), 106.78 (Ind C-3), 111.43 (Ind C-7), 118.77 (Ind C-6), 118.82 (Ind C-4), 122.98 (C-6'), 129.65 ($C_6H_5$), 130.07 (Ind C-9), 130.84 ($C_6H_5$), 131.52 ($C_6H_5$), 132.59 (Ind C-2), 134.34 ($C_6H_5$), 140.07 (Ind C-8), 143.83 (Ind C-5), 149.56 (C-5'), 166.79 (O(C=O)Ph), 176.95 (CONH), 178.88 (COOH); $[a]_D^{20}$= −53.2 (c=1.13, MeOH); HPLC (λ=350 nm): purity=96%, $t_R$=14.367 min; IR (KBr): ν=3436 (vs, OH), 2927 (s), 2852 (w), 1725 (m, C=O), 1647 (m, C=O), 1616 (w), 1583 (vw), 1520 (m), 1476 (vw), 1450 (m), 1402 (w), 1384 (w), 1336 (s, $NO_2$), 1315 (m), 1271 (m), 1223 (w), 1167 (w), 1114 (m), 1072 (s), 1040 (s), 999 (w), 966 (vw), 763 (vw), 746 (w), 712 (w) $cm^{-1}$.

Synthesis of Product 69

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(4-{1-[2-(6-nitro-1H-indol -3-yl)ethyl]-1H-1,2,3-triazol-4-yl}butyl)cyclohexanecarboxamide Following general procedure III, alkyne 23 (10.2 mg, 12.9 µmol), azide 27 (4.5 mg, 19.5 µmol), Na-L-ascorbate (64 µL, 6.40 µmol) and $CuSO_4.5H_2O$ (32 µL, 3.20 µmol) were dissolved in $^tBuOH/H_2O/THF$ 1:1:1 (1 mL; no prior degassing). After 2.5 h, 11.5 mg (85%) of triazole 69 was isolated by preparative HPLC-MS.

$^1H$-NMR (500 MHz, MeOD): δ 0.49-0.59 (m, 1H, Cy), 0.59-0.71 (m, 3H, Cy), 0.85-0.95 (m, 1H, Cy), 1.10 (d, J=6.5 Hz, 3H, Me), 1.14-1.24 (m, 3H, Cy, H-$6_a$, H-$2_a$), 1.24-1.36 (m, 9H, Fuc H-6, 4Cy, H-2'), 1.36-1.61 (m, 6H, H-3', Lac H-$3_b$, H-$6_b$, Cy), 1.61-1.71 (m, 1H, H-5), 2.10-2.16 (m, 1H, H-2), 2.20-2.28 (m, 1H, H-1), 2.50 (t, J=7.3 Hz, 2H, H-4'), 2.96-3.07 (m, 2H, H-1'), 3.14 (t, J=9.6 Hz, 1H, H-4), 3.57 (t, J=5.7 Hz, 1H, Gal H-5), 3.64 (dd, J=2.5, 9.7 Hz, 1H, Gal H-3), 3.66-3.82 (m, 5H, H-3, Fuc H-2, Fuc H-4, Gal H-6), 3.87 (dd, J=3.2, 10.3 Hz, 1H, Fuc H-3), 3.94-3.97 (m, 1H, Gal H-4), 4.00-4.05 (m, 1H, Lac H-2), 4.71 (d, J=8.0 Hz, 1H, Gal H-1), 4.74-4.78 (m, 2H, H-2"), 4.79-4.83 (m, 2H, H-1"'), 4.95-5.01 (m, 2H, Fuc H-1, Fuc H-5), 5.40-5.46 (m, 1H, Gal H-2), 6.69-6.72 (m, 1H, Ind H-3), 7.19-7.22 (m, 1H, Ind H-7), 7.22 (s, 1H, H-6'), 7.27-7.30 (m, 1H, Ind H-2), 7.41-7.46 (m, 2H, $C_6H_5$), 7.55-7.60 (m, 1H, $C_6H_5$), 7.95-7.99 (m, 1H, Ind H-6), 8.01-8.04 (m, 2H, $C_6H_5$), 8.52 (s, 1H, Ind H-4); $^{13}C$-NMR (125 MHz, MeOD): δ 16.72 (Fuc C-6), 19.24 (Me), 25.46 (C-4'), 26.49 (Cy), 26.66 (Cy), 27.24 (Cy), 27.59 (C-3'), 29.51 (C-2'), 33.08 (Cy), 34.13 (Cy), 35.02 (Cy), 35.32 (C-2), 37.52 (C-6), 39.34 (C-5), 39.79 (C-1'), 42.76 (Lac C-3), 43.27 (C-1), 47.49 (C-2"), 51.34 (C-1"), 62.72 (Gal C-6), 67.68 (Gal C-4), 67.73 (Fuc C-5), 70.29 (Fuc C-2), 71.39 (Fuc C-3), 72.95 (Gal C-2), 73.94 (Fuc C-4), 75.94 (Gal C-5), 77.98 (Lac C-2), 79.81 (C-3), 83.03 (C-4), 83.65 (Gal C-3), 100.44 (Fuc C-1), 100.47 (Gal C-1), 105.76 (Ind C-3), 110.21 (Ind C-7), 117.97 (Ind C-6), 118.69 82 (Ind C-4), 123.96 (C-6'), 129.12 (Ind C-9), 129.68 ($C_6H_5$), 130.84 ($C_6H_5$), 131.51 ($C_6H_5$), 132.46 (Ind C-2), 134.34 ($C_6H_5$), 140.49 (Ind C-8), 142.87 (Ind C-5), 148.89 (C-5'), 166.79 (O(C=O)Ph), 176.92 (CONH), 178.93 (COOH); $[a]_D^{20}$=−47.8 (c=1.10, MeOH); HPLC (λ=350 nm): purity=97%, $t_R$=14.000 min; IR (KBr): ν=3436 (vs, OH), 2927 (m), 2852 (w), 1725 (m, C=O), 1638 (m, C=O), 1584 (vw), 1516 (w), 1479 (vw), 1450 (w), 1383 (vw), 1335 (s, $NO_2$), 1269 (s), 1218 (w), 1166 (w), 1114 (m), 1071 (s), 1032 (m), 998 (w), 966 (vw), 746 (vw), 712 (w) $cm^{-1}$.

Synthesis of Product 70

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[2-(6-nitro-1H-indol -3-yl)ethyl]-1H-1,2,3-triazol-4-yl}methyl)cyclohexanecarboxamide Following general procedure III, alkyne 20 (9.2 mg, 11.8 µmol), azide 53 (3.6 mg, 15.6 µmol), Na-L-ascorbate (118 µL, 11.8 µmol), and $CuSO_4.5H_2O$ (59 µL, 5.90 µmol) were dissolved in $^tBuOH/H_2O/THF$ 1:1:1 (1 mL). After 1 h, the solvent was removed and the residue was purified by three preparative HPLC-MS runs ($H_2O/MeCN$+0.1% HCOOH). After the first purification, 5.7 mg (48%; purity<90%) of triazole 70 were obtained, after the third purification, 2.5 mg (21%; purity=99%) were isolated.

$^1H$-NMR (500 MHz, MeOD): δ 0.48-0.71 (m, 4H, 4 Cy), 0.84-0.95 (m, 1H, Cy), 1.10 (t, J=7.0 Hz, 3H, Me), 1.13-1.24 (m, 3H, H-$2_a$, H-$6_a$, Cy), 1.24-1.36 (m, 7H, 4Cy, Fuc H-6), 1.36-1.45 (m, 1H, Lac H-$3_a$), 1.45-1.53 (m, 1H, Lac H-$3_b$), 1.53-1.61 (m, 2H, Cy, H-$6_b$), 1.60-1.70 (m, 1H, H-5), 2.11-2.18 (m, 1H, H-$2_b$), 2.20-2.29 (m, 1H, H-1), 3.14 (t, J=9.6 Hz, 1H, H-4), 3.41 (t, J=6.7 Hz, 2H, H-2"), 3.57 (t, J=5.9 Hz, 1H, Gal H-5), 3.61 (dd, J=2.9, 9.7 Hz, 1H, Gal H-3), 3.65-3.82 (m, 5H, H-3, Fuc H-2, Fuc H-4, Gal H-6), 3.87 (dd, J=3.3, 10.3 Hz, 1H, Fuc H-3), 3.93-3.98 (m, 2H, Gal H-4, Lac H-2), 4.27 (s, 2H, H-1'), 4.66-4.71 (m, 3H, H-1", Gal H-1), 4.94-5.00 (m, 2H, Fuc H-1, Fuc H-5), 5.42 (dd, J=8.2, 9.6 Hz, 1H, Gal H-2), 7.21 (s, 1H, Ind H-2), 7.41-7.46 (m, 3H, $C_6H_5$, Ind H-7), 7.55-7.59 (m, 1H, $C_6H_5$), 7.66 (s, 1H, H-3'), 8.01-8.05 (m, 3H, Ind H-6, $C_6H_5$), 8.29-8.31 (m, 1H, Ind H-4); $^{13}C$-NMR (125 MHz, MeOD): δ 16.72 (Fuc C-6), 19.26 (Me), 26.54, 26.72, 27.09 (3C, Cy), 27.30 (C-2"), 33.12 (Cy), 34.24 (Cy), 35.12, 35.16 (2C, Cy, C-2), 35.54 (C-1'), 37.39 (C-6), 39.32 (C-5), 42.95, 42.98 (2C, C-1, Lac C-3), 52.36 (C-1"), 62.85 (Gal C-6), 67.74, 67.75 (2C, Gal C-4, Fuc C-5), 70.33 (Fuc C-2), 71.41 (Fuc C-3), 73.02 (Gal C-2), 73.96 (Fuc C-4), 76.03 (Gal C-5), 79.11 (Lac C-2)‡, 79.79 (C-3), 83.03 (C-4), 83.75 (Gal C-3), 100.44 (Fuc C-1), 100.54 (Gal C-1), 112.57 (Ind C-7), 114.78 (Ind C-3), 116.40 (Ind C-4), 117.99 (Ind C-6), 124.51 (C-3'), 127.90, 127.98 (2C, Ind C-2, Ind C-9), 129.69 ($C_6H_5$), 130.89 ($C_6H_5$), 131.60 ($C_6H_5$), 134.30 ($C_6H_5$), 141.03 (Ind C-8), 142.51 (Ind C-5), 146.17 (C-2')‡, 166.86 (O(C=O)Ph), 176.85 (CONH); HR-MS: m/z calcd for $C_{49}H_{64}N_6O_{17}$ [M+Na]$^+$: 1031.4220. found: 1031.4223. $[a]_D^{20}$=−62.7 (c=0.26, MeOH); HPLC (λ=350 nm): purity=99%, $t_R$=13.517 min; IR (KBr): ν=3435 (vs, OH), 2925 (w), 2852 (vw), 1720 (w, C=O), 1632 (m, C=O), 1517 (vw), 1451 (vw), 1383 (w), 1333 (m), 1268 (w), 1163 (w), 1076 (m), 1032 (m, $NO_2$), 966 (vw), 711 (vw), 675 (vw), 587 (vw) $cm^{-1}$.

Synthesis of Product 71

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-({1-[3-(6-nitro-1H-indol -3-yl)propyl]-1H-1,2,3-triazol-4-yl}methyl)cyclohexanecarboxamide Following general procedure III, alkyne 20 (14.4 mg, 18.5 µmol), azide 54 (6.8 mg, 27.7 µmol), Na-L-ascorbate (186 µL, 18.6 µmol) and CuSO$_4$.5H$_2$O (92 µL, 9.20 µmol) were dissolved in $^t$BuOH/H$_2$O/THF 1:1:1 (1 mL). After 1.5 h, triazole 71 (12.9 mg, 68%) was isolated by preparative HPLC-MS.

$^1$H-NMR (500 MHz, MeOD): δ 0.47-0.71 (m, 4H, Cy), 0.82-0.94 (m, 1H, Cy), 1.09 (d, J=6.4 Hz, 3H, Me), 1.12-1.44 (m, 11H, H-2$_a$, H-6$_a$, 5Cy, Lac H-3$_a$), 1.49 (ddd, J=3.6, 10.3, 13.6 Hz, 1H, Lac H-3$_b$), 1.52-1.70 (m, 4H, Cy, H-6$_b$, H-5), 2.12-2.20 (m, 1H, H-2$_b$), 2.26-2.36 (m, 3H, H-1, H-2"), 2.82 (t, J=7.5 Hz, 2H, H-3"), 3.13 (t, J=9.5 Hz, 1H, H-4), 3.53-3.58 (m, 2H, Gal H-5, Gal H-3), 3.65-3.81 (m, 5H, H-3, Fuc H-2, Fuc H-4, Gal H-6), 3.84-3.90 (m, 2H, Fuc H-3, Gal H-4), 3.94 (s, 1H, Lac H-2), 4.31-4.41 (m, 2H, H-1'), 4.46 (t, J=6.8 Hz, 2H, H-1"), 4.65 (d, J=8.1 Hz, 1H, Gal H-1), 4.93-4.98 (m, 2H, Fuc H-1, Fuc H-5), 5.41 (dd, J=8.5, 9.3 Hz, 1H, Gal H-2), 7.30 (s, 1H, Ind H-2), 7.38-7.44 (m, 2H, C$_6$H$_5$), 7.44-7.48 (m, 1H, Ind H-7), 7.55 (t, 1H, C$_6$H$_5$), 7.82 (s, 1H, H-3'), 7.98-8.02 (m, 2H, C$_6$H$_5$), 8.02-8.07 (m, 1H, Ind H-6), 8.45-8.48 (m, 1H, Ind H-4); $^{13}$C-NMR (125 MHz, MeOD): δ 16.72 (Fuc C-6), 19.24 (Me), 22.56 (C3"), 26.53, 26.74, 27.33 (3C, Cy), 31.89 (C-2"), 33.10, 34.29 (2C, Cy), 35.14, 35.20 (Cy, C-2), 35.63 (C-1'), 37.49 (C-6), 39.33 (C-5), 43.04 (Lac C-3), 43.14 (C-1), 50.86 (C-1"), 62.92 (Gal C-6), 67.71, 67.74 (2C, Gal C-4, Fuc C-5), 70.33 (Fuc C-2), 71.40 (Fuc C-3), 72.99 (Gal C-2), 73.96 (Fuc C-4), 76.01 (Gal C-5), 79.76 (C-3), 83.02 (C-4), 83.76 (Gal C-3), 100.41 (Fuc C-1), 100.55 (Gal C-1), 112.53 (Ind C-7), 116.55 (Ind C-4), 117.68 (Ind C-3), 117.93 (Ind C-6), 124.35 (C-3'), 127.11 (Ind C-2), 127.95 (Ind C-9), 129.66 (C$_6$H$_5$), 130.87 (C$_6$H$_5$), 131.65 (C$_6$H$_5$), 134.24 (C$_6$H$_5$), 141.25 (Ind C-8), 142.29 (Ind C-5), 166.84 (O(C=O)Ph), 176.98 (CONH); HR-MS: m/z calcd for C$_{50}$H$_{66}$N$_6$O$_{17}$ [M+Na]$^+$: 1045.4377. found: 1045.4381. [α]$_D^{20}$=−54.1 (c=0.3, MeOH); HPLC (λ=350 nm): purity=95%, t$_R$=13.883 min; IR (KBr): ν=3433 (vs, OH), 2925 (m), 2852 (w), 1722 (m, C=O), 1631 (m, C=O), 1520 (w), 1468 (w), 1451 (w), 1383 (w), 1333 (m, NO$_2$), 1270 (m), 1210 (w), 1163 (m), 1108 (m), 1074 (m), 1029 (m), 966 (vw), 892 (vw), 807 (vw), 776 (vw), 738 (vw), 712 (w), 672 (vw) cm$^{-1}$.

Synthesis of Product 72

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[2-(6-nitro-1H-indol-3-yl)ethyl]-1H-1,2,3-triazol-4-yl}ethyl)cyclohexanecarboxamide Following general procedure III, alkyne 21 (15.2 mg, 19.2 µmol), azide 53 (5.9 mg, 25.5 µmol), Na-L-ascorbate (96 µL, 9.60 µmol), and CuSO$_4$.5H$_2$O (48 µL, 4.80 µmol) were dissolved in $^t$BuOH/H$_2$O/THF 1:1:1 (1 mL). After 3 h, triazole 72 (13.7 mg, 70%) was isolated by preparative HPLC-MS.

$^1$H-NMR (500 MHz, MeOD): δ 0.50-0.73 (m, 4H, Cy), 0.84-0.96 (m, 1H, Cy), 1.08 (d, J=6.5 Hz, 3H, Me), 1.10-1.26 (m, 3H, H-6$_a$, H-2$_a$, $_{Cy)}$, 1.26-1.37 (m, 8H, 5Cy, Fuc H-6), 1.37-1.44 (m, 1H, Lac H-3$_a$), 1.46-1.58 (m, 3H, Lac H-3$_b$, Cy, H-6$_b$), 1.59-1.68 (m, 1H, H-5), 2.08-2.14 (m, 1H, H-2), 2.16-2.24 (m, 1H, H-1), 2.72 (t, J=7.2 Hz, 2H, H-2'), 3.12 (t, J=9.6 Hz, 1H, H-4), 3.24-3.29 (m, 2H, H-1'), 3.41 (t, J=6.7 Hz, 2H, H-2"), 3.54 (t, J=5.9 Hz, 1H, Gal H-5), 3.61 (dd, J=3.0, 9.7 Hz, 1H, Gal H-3), 3.67 (ddd, J=4.7, 9.3, 11.6 Hz, 1H, H-3), 3.70-3.81 (m, 4H, Fuc H-2, Fuc H-4, 2Gal H-6), 3.86 (dd, J=3.3, 10.3 Hz, 1H, Fuc H-3), 3.94 (d, J=2.4 Hz, 1H, Gal H-4), 4.01 (dd, J=3.1, 9.7 Hz, 1H, Lac H-2), 4.64-4.69 (m, 3H, Gal H-1, H-1"), 4.93-4.99 (m, 2H, Fuc H-1, Fuc H-5), 5.42 (dd, J=8.2, 9.6 Hz, 1H, Gal H-2), 7.22 (s, 1H, Ind H-2), 7.41-7.48 (m, 3H, Ind H-7, C$_6$H$_5$), 7.51-7.57 (m, 1H, C$_6$H$_5$), 7.60 (s, 1H, H-4'), 7.99-8.05 (m, 3H, Ind H-6, C$_6$H$_5$), 8.09 (s, 1H, NH), 8.28-8.32 (m, 1H, Ind H-4); $^{13}$C-NMR (125 MHz, MeOD): δ 16.71 (Fuc C-6), 19.24 (Me), 26.47, 26.53, 26.70 (3C, 2Cy, C-2'), 27.12, 27.26 (2C, Cy, C-2"), 33.14 (Cy), 34.18 (Cy), 35.04 (Cy), 35.29 (C-2), 37.43 (C-6), 39.31 (C-5), 39.96 (C-1'), 42.77 (Lac C-3), 43.22 (C-1), 52.34 (C-1"), 62.76 (Gal C-6), 67.71, 67.77 (2C, Gal C-4 Fuc C-5), 70.32 (Fuc C-2), 71.42 (Fuc C-3), 73.02 (Gal C-2), 73.96 (Fuc C-4), 75.97 (Gal C-5), 78.06 (Lac C-2), 79.83 (C-3), 83.01 (C-4), 83.67 (Gal C-3), 100.42 (Fuc C-1), 100.53 (Gal C-1), 112.58 (Ind C-7), 114.82 (Ind C-3), 116.36 (Ind C-4), 117.99 (Ind C-6), 124.01 (C-4'), 127.93, 127.95 (2C, Ind C-2, Ind C-9), 129.73 (C$_6$H$_5$), 130.88 (C$_6$H$_5$), 131.55 (C$_6$H$_5$), 134.37 (C$_6$H$_5$), 140.99 (Ind C-8), 142.53 (Ind C-5), 146.19 (C-3'), 166.83 (O(C=O)Ph), 176.99 (CONH), 178.96 (COOH); HR-MS: m/z calcd for C$_{50}$H$_{66}$N$_6$O$_{17}$ [M+Na]$^+$: 1045.4377. found: 1045.4375. [α]$_D^{20}$=−53.9 (c=1.04, MeOH); HPLC (λ=350 nm): purity=100%, t$_R$=13.550 min; IR (KBr): ν=3431 (vs, OH), 2927 (m), 2852 (w), 1721 (m, C=O), 1647 (m, C=O), 1545 (w), 1522 (w), 1471 (w), 1450 (w), 1380 (w), 1334 (s, NO$_2$), 1272 (m), 1221 (w), 1163 (w), 1097 (s), 1079 (s), 1029 (m), 999 (w), 963 (vw), 809 (vw), 785 (vw), 741 (vw), 712 (w), 678 (w) cm$^{-1}$.

Synthesis of Product 73

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(2-{1-[3-(6-nitro-1H-indol -3-yl)propyl]-1H-1,2,3-triazol-4-yl}ethyl)cyclohexanecarboxamide Following general procedure III, alkyne 21 (15.8 mg, 20.0 µmol), azide 54 (6.9 mg, 28.1 µmol), Na-L-ascorbate (100 µL, 10.0 µmol), and CuSO$_4$.5H$_2$O (50 µL, 5.00 µmol) were dissolved in $^t$BuOH/H$_2$O/THF 1:1:1 (1 mL). After 3 h, triazole 73 (14.1 mg, 68%) was isolated by preparative HPLC-MS.

$^1$H-NMR (500 MHz, MeOD): δ 0.50-0.72 (m, 4H, Cy), 0.83-0.95 (m, 1H, Cy), 1.00 (d, J=6.5 Hz, 3H, Me), 1.04-1.25 (m, 3H, H-2$_a$, H-6$_a$, Cy), 1.26-1.36 (m, 7H, 4Cy, Fuc H-6), 1.36-1.44 (m, 1H, Lac H-3$_a$), 1.45-1.62 (m, 4H, Lac H-3$_b$, Cy, H-6$_b$, H-5), 2.08-2.15 (m, 1H, H-2$_b$), 2.20 (tt, J=3.2, 12.7 Hz, 1H, H-1), 2.24-2.34 (m, 2H, H-2"), 2.77-2.85 (m, 4H, H-2', H-3"), 3.06 (t, J=9.6 Hz, 1H, H-4), 3.39 (t, J=7.0 Hz, 2H, H-1'), 3.52 (t, J=6.0 Hz, 1H, Gal H-5), 3.59 (dd, J=2.8, 9.7 Hz, 1H, Gal H-3), 3.64 (ddd, J=4.6, 9.1, 11.6 Hz, 1H, H-3), 3.69-3.81 (m, 4H, Fuc H-2, Fuc H-4, Gal H-6), 3.85 (dd, J=3.3, 10.3 Hz, 1H, Fuc H-3), 3.93 (d, J=2.1 Hz, 1H, Gal H-4), 3.98 (dd, J=2.5, 9.6 Hz, 1H, Lac H-2), 4.36-4.47 (m, 2H, H-1"), 4.64 (d, J=8.1 Hz, 1H, Gal H-1), 4.90-4.93 (m, 1H, Fuc H-1), 4.96 (q, J=6.4 Hz, 1H, Fuc H-5), 5.42 (dd, J=8.2, 9.6 Hz, 1H, Gal H-2), 7.30 (s, 1H, Ind H-2), 7.43-7.50 (m, 3H, Ind H-7, C$_6$H$_6$), 7.55-7.61 (m, 1H, C$_6$H$_6$), 7.70 (s, 1H, H-4'), 8.01-8.09 (m, 3H, C$_6$H$_6$, Ind H-6), 8.47-8.51 (m, 1H, Ind H-4); $^{13}$C-NMR (125 MHz, MeOD): δ 16.73 (Fuc C-6), 19.17 (Me), 22.58 (C-3"), 26.53, 26.55, 26.71 (3C, 2Cy, C-2'), 27.29 (Cy), 31.85 (C-2"), 33.12 (Cy), 34.24 (Cy), 35.12 (Cy), 35.30 (C-2), 37.43 (C-6), 39.25 (C-5), 39.87 (C-1'), 42.95 (Lac C-3), 43.17 (C-1), 50.75 (C-1"), 62.84 (Gal C-6), 67.72, 67.73 (2C, Gal C-4, Fuc C-5), 70.31 (Fuc C-2), 71.41 (Fuc C-3), 73.03 (Gal C-2), 73.95 (Fuc C-4), 75.97 (Gal C-5), 78.36 (Lac C-2)‡, 79.77 (C-3), 83.01 (C-4), 83.72 (Gal C-3), 100.39 (Fuc C-1), 100.54 (Gal C-1), 112.53 (Ind C-7), 116.59 (Ind C-4), 117.69 (Ind C-3), 117.93 (Ind C-6), 123.79 (C-4'), 127.12 (Ind C-2), 127.94 (Ind C-9), 129.74 (C$_6$H$_5$), 130.91 (C$_6$H$_5$), 131.63 (C$_6$H$_5$), 134.36 (C$_6$H$_5$), 141.23 (Ind C-8), 142.30 (Ind C-5), 146.29 (C-3'), 166.84 (O(C=O)Ph), 177.00 (CONH); HR-MS: m/z calcd for $C_{51}H_{68}N_6O_{17}$ [M+H]$^+$: 1037.4714. found: 1037.4714. [a]$_D^{20}$=−59.7 (c=1.22, MeOH); HPLC (λ=350 nm): purity=100%, $t_R$=13.717 min; IR (KBr): ν=3430 (vs, OH), 2927 (m), 2852 (w), 1720 (m, C=O), 1647 (m, C=O), 1547 (w), 1520 (w), 1471 (w), 1450 (w), 1333 (s, NO$_2$), 1272 (m), 1221 (w), 1163 (w), 1097 (s), 1078 (s), 1029 (m), 999 (w), 966 (vw), 809 (vw), 778 (vw), 738 (vw), 712 (w), 678 (vw) cm$^{-1}$.

Synthesis of Product 74

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[2-(6-nitro-1H-indol-3-yl)ethyl]-1H-1,2,3-triazol-4-yl}propyl)cyclohexanecarboxamide Following general procedure III, alkyne 22 (14.5 mg, 18.0 μmol), azide 53 (6.3 mg, 27.2 μmol), Na-L-ascorbate (90 μL, 9.00 μmol), and CuSO$_4$.5H$_2$O (45 μL, 4.50 μmol) were dissolved in $^t$BuOH/H$_2$O/MeCN 1:1:1 (1 mL). After 15 h, triazole 74 (10.3 mg, 55%) was isolated by preparative HPLC-MS.

$^1$H-NMR (500 MHz, MeOD): δ 0.46-0.71 (m, 4H, Cy), 0.81-0.94 (m, 1H, Cy), 1.11 (d, J=6.5 Hz, 3H, Me), 1.14-1.37 (m, 10H, H-2$_a$, H-6$_a$, 5Cy, Fuc H-6), 1.36-1.45 (m, 1H, Lac H-3$_a$), 1.45-1.56 (m, 2H, Lac H-3$_{b, Cy}$), 1.56-1.63 (m, 1H, H-6$_b$), 1.62-1.74 (m, 3H, H-5, H-2'), 2.11-2.19 (m, 1H, H-2$_b$), 2.20-2.30 (m, 1H, H-1), 2.53-2.64 (m, 2H, H-3'), 2.95-3.11 (m, 2H, H-1'), 3.15 (t, J=9.4 Hz, 1H, H-4), 3.41 (t, J=6.5 Hz, 2H, H-2"), 3.55-3.65 (m, 2H, Gal H-3, Gal H-5), 3.66-3.83 (m, 5H, H-3, Fuc H-2, Fuc H-4, Gal H-6), 3.87 (dd, J=2.8, 10.3 Hz, 1H, Fuc H-3), 3.90-4.04 (m, 2H, Gal H-4 Lac H-2)), 4.61-4.74 (m, 3H, Gal H-1, H-1"), 4.95-5.01 (m, 2H, Fuc H-1, Fuc H-5), 5.38-5.48 (m, 1H, Gal H-2), 7.23 (s, 1H Ind H-2,), 7.35-7.45 (m, 3H, Ind H-7, C$_6$H$_5$), 7.48-7.53 (m, 1H, C$_6$H$_5$), 7.58 (s, 1H, H-5'), 7.99-8.05 (m, 3H, Ind H-6, C$_6$H$_5$), 8.21-8.25 (m, 1H, Ind H-4); $^{13}$C-NMR (125 MHz, MeOD): δ 16.72 (Fuc C-6), 19.28 (Me), 23.50 (C-3'), 26.50, 26.71 (2C, Cy), 27.09 (C-2"), 27.28 (Cy), 30.12 (C-2'), 33.12, 34.38, 35.13 (3C, Cy), 35.41 (C-2), 37.45 (C-6), 39.34, 39.40 (2C, C-1', C-5), 43.33 (2C, Lac C-3, C-1), 52.54 (C-1"), 62.88 (Gal C-5)), 67.73 (2C, Fuc C-5, Gal C-4), 70.33 (Fuc C-2), 71.41 (Fuc C-3), 73.08 (Gal C-2), 73.97 (Fuc C-4), 76.26 (Lac C-2), 79.84 (C-3), 83.03 (C-4), 83.70 (Gal C-3), 100.43 (Fuc C-1), 100.59 (Gal C-1), 112.55 (Ind C-7), 114.91 (Ind C-3), 116.35 (Ind C-4), 117.93 (Ind C-6), 123.98 (C-5')‡, 127.99 (2C, Ind C-2, Ind C-9), 129.66 (C$_6$H$_5$), 130.85 (C$_6$H$_5$), 131.55 (C$_6$H$_5$), 134.27 (C$_6$H$_5$), 140.96 (Ind C-8), 142.49 (Ind C-5), 148.09 (C-4')§, 166.82 (O(C=O)Ph), 177.03 (CONH); HR-MS: m/z calcd for $C_{51}H_{68}N_6O_{17}$ [M+Na]$^+$: 1059.4533. found: 1059.4528. [a]$_D^{20}$=−32.3 (c=0.31, MeOH); HPLC (λ=350 nm): purity=95%, $t_R$=13.617 min; IR (KBr): ν=3434 (vs, OH), 2926 (m), 282 (w), 1720 (w, C=O), 1631 (m, C=O), 1547 (w), 1520 (w), 1468 (w), 1449 (w), 1380 (w), 1333 (m, NO$_2$), 1268 (m), 1169 (w), 1161 (w), 1097 (m), 1074 (m), 1032 (m), 999 (w), 712 (w) cm$^{-1}$.

Synthesis of Product 75

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[3-(6-nitro-1H-indol-3-yl)propyl]-1H-1,2,3-triazol-4-yl}propyl)cyclohexanecarboxamide Following general procedure III, alkyne 22 (11.6 mg, 14.4 μmol), azide 54 (5.3 mg, 21.6), Na-L-ascorbate (72 μL, 7.20 μmol), and CuSO$_4$.5H$_2$O (36 μL, 3.60 μmol) were dissolved in $^t$BuOH/H$_2$O/THF 1:1:1 (1 mL). After 2 h, triazole 75 (9.5 mg, 63%) was isolated by preparative HPLC-MS.

$^1$H-NMR (500 MHz, MeOD): δ 0.46-0.67 (m, 4H, Cy), 0.85 (d, J=11.4 Hz, 1H, Cy), 1.10 (d, J=6.4 Hz, 3H, Me), 1.13-1.44 (m, 11H, H-2$_a$, H-6$_a$, 5Cy, Fuc H-6, Lac H-3$_a$), 1.44-1.55 (m, 2H, Lac H-3$_b$), 1.53-1.62 (m, 1H, H-6), 1.63 (d, J=16.3 Hz, 1H, H-5), 1.75-1.84 (m, 2H, H-2'), 2.11-2.19 (m, 1H, H-2), 2.25 (tt, J=3.5, 13.0 Hz, 1H, H-1), 2.29-2.39 (m, 2H, H-2"), 2.66-2.72 (m, 2H, H-3'), 2.82 (t, J=7.4 Hz, 2H, H-3"), 3.06-3.23 (m, 3H, H-1', H-4), 3.60 (dt, J=8.4, 11.3 Hz, 2H, Gal H-5, Gal H-3), 3.65-3.84 (m, 5H, H-3, Fuc H-3, Fuc H-4, Gal H-6), 3.87 (dd, J=3.2, 10.3 Hz, 1H, Fuc H-3), 3.96 (s, 2H, Lac H-2, Gal H-4), 4.45 (t, J=6.8 Hz, 2H, H-1"), 4.69 (d, J=8.0 Hz, 1H, Gal H-1), 4.97 (ddd, J=4.9, 14.3, 19.5 Hz, 2H, Fuc H-1, Fuc H-5), 5.38-5.45 (m, 1H, Gal H-2), 7.30 (s, 1H, Ind H-2), 7.34-7.38 (m, 2H, C$_6$H$_5$), 7.44-7.46 (m, 1H, Ind H-7), 7.48-7.52 (m, 1H, C$_6$H$_5$), 7.74 (s, 1H, H-5'), 7.98-8.02 (m, 2H, C$_6$H$_5$), 8.02-8.05 (m, 1H, Ind H-6), 8.45-8.48 (m, 1H, Ind H-4); $^{13}$C-NMR (125 MHz, MeOD): δ 16.72 (Fuc C-6), 19.25 (Me), 22.55 (C-3"), 23.63 (C-3'), 26.46, 26.67, 27.25 (3C, Cy), 30.31 (C-2'), 31.86 (C-2"), 33.08, 34.19, 35.07 (3C, Cy), 35.47 (C-2), 37.41 (C-6), 39.32 (C-5), 39.54 (C-1'), 42.88 (Lac C-3), 43.36 (C-1), 50.80 (C-1"), 62.82 (Gal C-6), 67.71, 67.73 (2C, Gal C-4, Fuc C-5), 70.34 (Fuc C-2), 71.42 (Fuc C-3), 72.99 (Gal C-2), 73.97 (Fuc C-4), 75.99 (Gal C-5), 78, 69 (Lac C-2)‡, 79.89 (C-3), 83.03 (C-4), 83.70 (Gal C-3), 100.44 (Fuc C-1), 100.58 (Gal C-1), 112.51 (Ind C-7), 116.55 (Ind C-4), 117.69 (Ind C-3), 117.89 (Ind C-6), 123.54 (C-5'), 127.11 (Ind C-2), 127.96 (Ind C-9), 129.64 (C$_6$H$_5$), 130.83 (C$_6$H$_5$), 131.55 (C$_6$H$_5$), 134.27 (C$_6$H$_5$), 141.22 (Ind C-8), 142.25 (Ind C-5), 148.53 (C-4')§, 166.79 (O(C=O)Ph), 177.05 (CONH); HR-MS: m/z calcd for $C_{52}H_{70}N_6O_{17}$ [M+H]$^+$: 1051.4870. found: 1051.4870. [a]$_D^{20}$=−47.6 (c=0.87, MeOH); HPLC (λ=350 nm): purity=98%, $t_R$=13.767 min; IR (KBr): ν=3431 (vs, OH), 2927 (m), 2852 (w), 1720 (s, C=O), 1631 (m, C=O), 1547 (w), 1517 (w), 1471 (w), 1450 (w), 1383 (w), 1332 (s, NO$_2$), 1270 (m), 1213 (w), 1166 (w), 1106 (s), 1073 (s), 1032 (m), 996 (w), 963 (vw), 807 (vw), 774 (vw), 741 (vw), 712 (w), 669 (vw) cm$^{-1}$.

Synthesis of Product 76

(1R,3R,4R,5S)—N-(3-{1-[3-(5-Amino-1H-indol-1-yl)propyl]-1H-1,2,3-triazol-4-yl}propyl)-3-[2-O-benzoyl-3-O-((1S)-1-carboxy-2-cyclohexyl-ethyl)-(β-D-galactopyranosyl)oxy]-4-[(α-L-fucopyranosyl)oxy]-5-methylcyclohexanecarboxamide A mixture of nitroindole 66 (8.5 mg, 8.09 μmol), PtO$_2$ (2 mg, cat.), morpholine (5 μL) in MeOH was stirred at r.t. under an H$_2$ atmosphere (atm. pressure). Completion of the reaction was indicated by discoloration of the solution and confirmed by MS after 30 min. The catalyst was removed via filtration through a PTFE membrane filter, and the solution was concentrated in vacuo. Purification by preparative HPLC-MS (H$_2$O/MeCN+0.1% HCOOH) gave the amine 76 as a colorless solid (4.5 mg, 54%).

$^1$H-NMR (500 MHz, MeOD): δ 0.39-0.65 (m, 4H, Cy), 0.77-0.87 (m, 1H, Cy), 1.04 (d, J=5.8 Hz, 3H, Me), 1.09-1.36 (m, 11H, H-2$_a$, H-6$_a$, 5Cy, Fuc H-6, Lac H-3), 1.43 (t, J=11.9 Hz, 1H, Lac H-3), 1.47-1.55 (m, 2H, H-6, Cy), 1.55-1.64 (m, 1H, H-5), 1.70-1.78 (m, 2H, H-2')), 2.05-2.12 (m, 1H, H-2), 2.19 (t, J=11.8 Hz, 1H, H-1), 2.39 (p, J=6.6 Hz, 2H, H-2"), 2.62 (t, J=7.0 Hz, 2H, H-3'), 3.02-3.16 (m, 3H, H-1', H-4), 3.47-3.54 (m, 2H, Gal H-3, Gal H-3, Gal H-5), 3.60-3.80 (m, 6H, H-3, Fuc H-2, Fuc H-4, Gal H-6, Lac H-2), 3.80-3.86 (m,

1H, Fuc H-3), 3.89 (s, 1H, Gal H-4), 4.20 (t, J=6.5 Hz, 2H, H-3"), 4.30 (t, J=6.3 Hz, 2H, H-1"), 4.62 (d, J=8.1 Hz, 1H, Gal H-1), 4.89-4.97 (m, 2H, Fuc H-1, Fuc H-5), 5.37 (t, J=8.7 Hz, 1H, Gal H-2), 6.41 (s, 1H, Ind H-3), 6.92-6.98 (m, 1H, Ind H-6), 7.27 (s, 1H, Ind H-2), 7.29-7.37 (m, 4H, $C_6H_5$, Ind H-4, Ind H-7), 7.42-7.48 (m, 1H, $C_6H_5$), 7.60 (s, 1H, H-5'), 7.94-8.00 (m, 2H, $C_6H_5$); $^{13}$C-NMR (125 MHz, MeOD): δ 16.75 (Fuc C-6), 19.26 (Me), 23.54 (C-3'), 26.53, 26.77, 27.34 (3C, Cy), 30.15 (C-2'), 31.60 (C-2"), 33.05, 34.33, 35.26 (3C, Cy), 35.50 (C-2), 37.39 (C-6), 39.26 (C-5), 39.41 (C-1'), 43.27 (2C, Lac C-3, C-1), 44.28 (C-3"), [48.66 (C-1")], 63.02 (Gal C-6), 67.70, 67.78 (2C, Gal C-4, Fuc C-5), 70.28 (Fuc C-2), 71.36 (Fuc C-3), 73.07 (Gal C-2), 73.94 (Fuc C-4), 76.10 (Gal C-5), 79.74 (C-3), 79.89 (Lac C-2), 83.02 (C-4), 83.66 (Gal C-3), 100.46 (Fuc C-1), 100.62 (Gal C-1), 102.22 (Ind C-3), 111.54 (Ind C-4), 112.92 (Ind C-6), 115.87 (Ind C-7), 123.58 (C-5'), 129.63 ($C_6H_5$), 130.84, 130.87 (2C, $C_6H_5$, Ind H-2), 131.68 (Ind C-8), 134.19 ($C_6H_5$), 135.30 (Ind C-5), 148.45 (C-4'), 166.78 (O(C=O)Ph), 177.05 (CONH), 181.91 (COOH); $[α]_D^{20}$=−59.1 (c=0.45, MeOH); HPLC (λ=350 nm): purity=97%, $t_R$=11.167 min; IR (KBr): ν=3431 (vs, OH), 2926 (m), 2853 (w), 1722 (w), 1643 (m), 1603 (m), 1584 (m), 1555 (w), 1492 (w), 1451 (m), 1406 (w), 1384 (w), 1365 (w), 1348 (w), 1316 (m), 1273 (m), 1222 (vw), 1167 (w), 1118 (m), 1096 (m), 1079 (s), 1031 (m), 1000 (w), 967 (vw), 804 (vw), 768 (vw), 713 (m) cm$^{-1}$.

Synthesis of Product 77

(1R,3R,4R,5S)—N-(3-{1-[3-(5-Acetamido-1H-indol-1-yl)propyl]-1H-1,2,3-triazol-4-yl}propyl)-3-[2-O-benzoyl-3-O-((1S)-1-carboxy-2-cyclohexyl-ethyl)-(β-D-galactopyranosyl)oxy]-4-[(α-L-fucopyranosyl)oxy]-5-methylcyclohexanecarboxamide Following general procedure III, alkyne 22 (11.6 mg, 14.4 µmol), azide 38 (13 mg, 22.3 µmol), Na-L-ascorbate (72 µL, 7.20 µmol) and CuSO$_4$.5H$_2$O (36 µL, 3.60 µmol) were stirred in $^t$BuOH/H$_2$O/THF 1:1:1 (1 mL; no prior degassing). After removal of the solvent under reduced pressure, the crude product was redissolved in MeOH, and centrifuged. The supernatant was subjected to preparative HPLC-MS to afford 77 as a colorless solid (11.0 mg, 73%).

$^1$H-NMR (500 MHz, MeOD): δ 0.47-0.57 (m, 1H, Cy), 0.57-0.70 (m, 3H, Cy), 0.82-0.94 (m, 1H, Cy), 1.10 (d, J=6.4 Hz, 3H, Me), 1.13-1.36 (m, 8H, H-2$_a$, H-6$_a$, 5Cy, Fuc H-6), 1.35-1.44 (m, 1H, Lac H-3$_a$), 1.44-1.51 (m, 1H, Lac H-3$_b$), 1.51-1.61 (m, 2H, H-6$_b$, Cy), 1.61-1.70 (m, 1H, H-5), 1.73-1.80 (m, 2H, H-2'), 2.10-2.15 (m, 4H, H-2$_b$, NHAc-Me), 2.21-2.29 (m, 1H, H-1), 2.42 (p, J=6.7 Hz, 2H, H-2"), 2.65 (t, J=7.5 Hz, 2H, H-3'), 3.06-3.18 (m, 3H, H-1', H-4), 3.53-3.57 (m, 1H, Gal H-5), 3.60 (dd, J=2.8, 9.7 Hz, 1H, Gal H-3), 3.65-3.81 (m, 5H, H-3, Fuc H-2, Fuc H-4, Gal H-6), 3.86 (dd, J=3.2, 10.3 Hz, 1H, Fuc H-3), 3.94 (d, J=2.1 Hz, 1H, Gal H-4), 4.00 (dd, J=2.3, 9.6 Hz, 1H, Lac H-2), 4.20 (t, J=6.7 Hz, 2H, H-3"), 4.32 (t, J=6.8 Hz, 2H, H-1"), 4.67 (d, J=8.0 Hz, 1H, Gal H-1), 4.94-5.01 (m, 2H, Fuc H-1, Fuc H-5), 5.40-5.44 (m, 1H, Gal H-2), 6.40-6.43 (m, 1H, Ind H-3), 7.18-7.28 (m, 3H, Ind H-2, Ind H-6, Ind H-7), 7.33-7.41 (m, 2H, $C_6H_5$), 7.47-7.52 (m, 1H, $C_6H_5$), 7.60 (s, 1H, H-5'), 7.75-7.79 (m, 1H, Ind H-4), 7.99-8.03 (m, 2H, $C_6H_5$); $^{13}$C-NMR (125 MHz, MeOD): δ 16.74 (Fuc C-6), 19.25 (Me), 23.54 (Ac-Me), 23.67 (C-3'), 26.50, 26.68, 27.25 (3C, Cy), 30.23 (C-2'), 31.61 (C-2"), 33.07, 34.14, 35.05 (3C, Cy), 35.43 (C-2), 37.43 (C-6), 39.33, 39.47 (2C, C-5, C-1'), 42.81 (Lac C-3), 43.30 (C-1), 44.14 (C-3"), 48.66 (C-1")‡, 62.76 (Gal C-6), 67.70 (2C, Gal C-4, Fuc C-5), 70.28 (Fuc C-2), 71.39 (Fuc C-3), 72.95 (Gal C-2), 73.96 (Fuc C-4), 75.95 (Gal C-5), 78.15 (Lac C-2), 79.80 (C-3), 83.03 (C-4), 83.65 (Gal C-3), 100.47 (Fuc C-1), 100.50 (Gal C-1), 102.48 (Ind C-3), 110.34 (Ind C-7), 114.12 (Ind C-4), 117.20 (Ind C-6), 123.59 (C-5'), 129.68 ($C_6H_5$), 129.97 (Ind C-9), 130.11 (Ind C-2), 130.83 ($C_6H_5$), 131.52, 131.94 (2C, Ind C-5, $C_6H_5$), 134.32 ($C_6H_5$), 134.78 (Ind C-8), 147.95 (C-4'), 166.76 (O(C=O)Ph), 171.50 (MeCONH), 177.04 (CONH), 178.70 (COOH). $[α]_D^{20}$=−49.4 (c=0.83, MeOH); HPLC (λ=350 nm): purity=95%, $t_R$=12.483 min; IR (KBr): ν=3422 (vs, OH), 2927 (s), 2853 (m), 1725 (s, C=O), 1651 (s, C=O), 1603 (m), 1587 (m), 1548 (m), 1488 (m), 1450 (m), 1401 (w), 1373 (m), 1337 (m), 1316 (m), 1271 (vs), 1113 (vs), 1076 (vs), 1033 (s), 1000 (w), 874 (vw), 804 (w), 762 (w), 762 (w), 713 (m), 675 (w) cm$^{-1}$.

Synthesis of Product 78

(1R,3R,4R,5S)—N-(3-{1-[3-(5-{2-[2-(2-Aminoethoxy)ethoxy]acetamido}-1H-indol-1-yl)propyl]-1H-1,2,3-triazol-4-yl}propyl)-3-[2-O-benzoyl-3-O-((1S)-1-carboxy-2-cyclohexyl-ethyl)-(β-D-galactopyranosyl)oxy]-4-[(α-L-fucopyranosyl)oxy]-5-methylcyclohexanecarboxamide Following general procedure III, alkyne 22 (12.0 mg, 14.9 µmol), azide 40 (13 mg, 22.3 µmol), Na-L-ascorbate (75 µL, 7.50 µmol) and CuSO$_4$.5H$_2$O (38 µL, 3.80 µmol) were stirred in $^t$BuOH/H$_2$O/THF 1:1:1 (1 mL; no prior degassing) for 2 h, followed by the addition of piperidine (4.4 µL). After another hour, further 10 µL of piperidine was added, and stirring was continued for 2 h. Following removal of the solvent in vacuo, the residue was dissolved in MeOH, filtrated through a PTFE membrane filter, and the solution was centrifuged. The supernatant was subjected to preparative HPLC-MS to afford 78 as a colorless solid (11.4 mg, 66%).

$^1$H-NMR (500 MHz, MeOD): δ 0.39-0.69 (m, 4H, Cy), 0.79-0.93 (m, 1H, Cy), 1.09 (d, J=6.4 Hz, 3H, Me), 1.12-1.41 (m, 11H, H-2$_a$, H-6$_a$, 4Cy, Fuc H-6, Lac H-3$_a$), 1.41-1.51 (m, 1H, Lac H-3), 1.51-1.61 (m, 2H, H-6$_b$, Cy), 1.61-1.73 (m, 1H, H-5), 1.73-1.84 (m, 2H, H-2'), 2.10-2.15 (m, 1H, H-2$_b$), 2.21-2.29 (m, 1H, H-1), 2.44 (p, J=6.6 Hz, 2H, H-2"), 2.62-2.69 (m, 2H, H-3'), 3.05-3.20 (m, 5H, H-1', H-4, H-6), 3.49 (d, J=9.2 Hz, 1H, Gal H-3), 3.52-3.57 (m, 1H, Gal H-5), 3.65-3.83 (m, 12H, H-3, Fuc H-2, Fuc H-4, Gal H-6, H-3*, H-4*, H-5*, Lac H-2), 3.86 (dd, J=3.2, 10.3 Hz, 1H, Fuc H-3), 3.89-3.94 (m, 1H, Gal H-4), 4.18-4.25 (m, 4H, H-2*, H-3"), 4.34 (t, J=6.7 Hz, 2H, H-1"), 4.64 (d, J=8.1 Hz, 1H, Gal H-1), 4.94-5.00 (m, 3H, Fuc H-1, Fuc H-5), 5.39 (t, J=8.8 Hz, 1H, Gal H-2), 6.43-6.46 (m, 1H, Ind H-3), 7.24-7.27 (m, 1H, Ind H-2), 7.28 (s, 2H, Ind H-6, Ind H-7), 7.31-7.36 (m, 2H, $C_6H_5$), 7.43-7.49 (m, 1H, $C_6H_5$), 7.61 (s, 1H, H-5'), 7.83 (s, 1H, Ind H-4), 7.95-8.01 (m, 2H, $C_6H_5$); $^{13}$C-NMR (125 MHz, MeOD): δ 16.79 (Fuc C-6), 19.29 (Me), 23.54 (C-3'), 26.52, 26.77, 27.36 (3C, Cy), 30.19 (C-2'), 31.60 (C-2"), 33.03, 34.37, 35.33 (3C, Cy), 35.53 (C-2), 37.40 (C-6), 39.25, 39.42 (2C, C-5, C-1'), 40.57 (C-6*), 43.23 (C-1), 43.43 (Lac C-3), 44.20 (C-3"), 48.69 (C-1")‡, 63.06 (Gal C-6), 67.59, 67.74 (2C, Gal C-4, Fuc C-5), 68.00 (C-5*), 70.27 (Fuc C-2) 70.33, 71.36 (2C, Fuc C-3, C-2), 71.48 (2C, C-3*, C-4), 73.00 (Gal C-2), 73.94 (Fuc C-4), 76.06 (Gal C-5), 79.75 (C-3), 83.02 (C-4), 83.69 (Gal C-3), 100.39 (Fuc C-1), 100.62 (Gal C-1), 102.57 (Ind C-3), 110.52 (Ind C-7), 114.43 (Ind C-), 117.31 (Ind C-6), 123.66 (C-5'), 129.62 ($C_6H_5$), 130.13, 130.18 (2C, Ind C-2, Ind C-9), 130.82 ($C_6H_5$), 130.96, 131.66 (2C, Ind C-5, $C_6H_5$), 134.16 ($C_6H_5$), 135.01 (Ind C-8), 148.82 (C-4'), 166.78 (O(C=O)Ph), 170.59 (C-1*), 177.03 (CONH); HPLC (λ=350 nm): purity=95%, $t_R$=12.483 min; $[a]_D^{20}$= −44.4 (c=0.67, MeOH); IR (KBr): ν=3430 (vs, OH), 3137 (m, NH$_2$), 2925 (vs), 2855 (m), 1724 (m), 1720 (m), 1654 (s), 1649 (s), 1586 (s), 1542 (m), 1489 (m), 1450 (m), 1401 (w), 1385 (w), 1340 (w), 1293 (w), 1272 (s), 1219 (vw), 1163 (w), 1117 (vs), 1098 (vs), 1079 (vs), 1032 (s), 997 (w), 967 (vw), 802 (vw), 763 (vw), 714 (w) cm$^{-1}$.

Example 4

Figure 7:
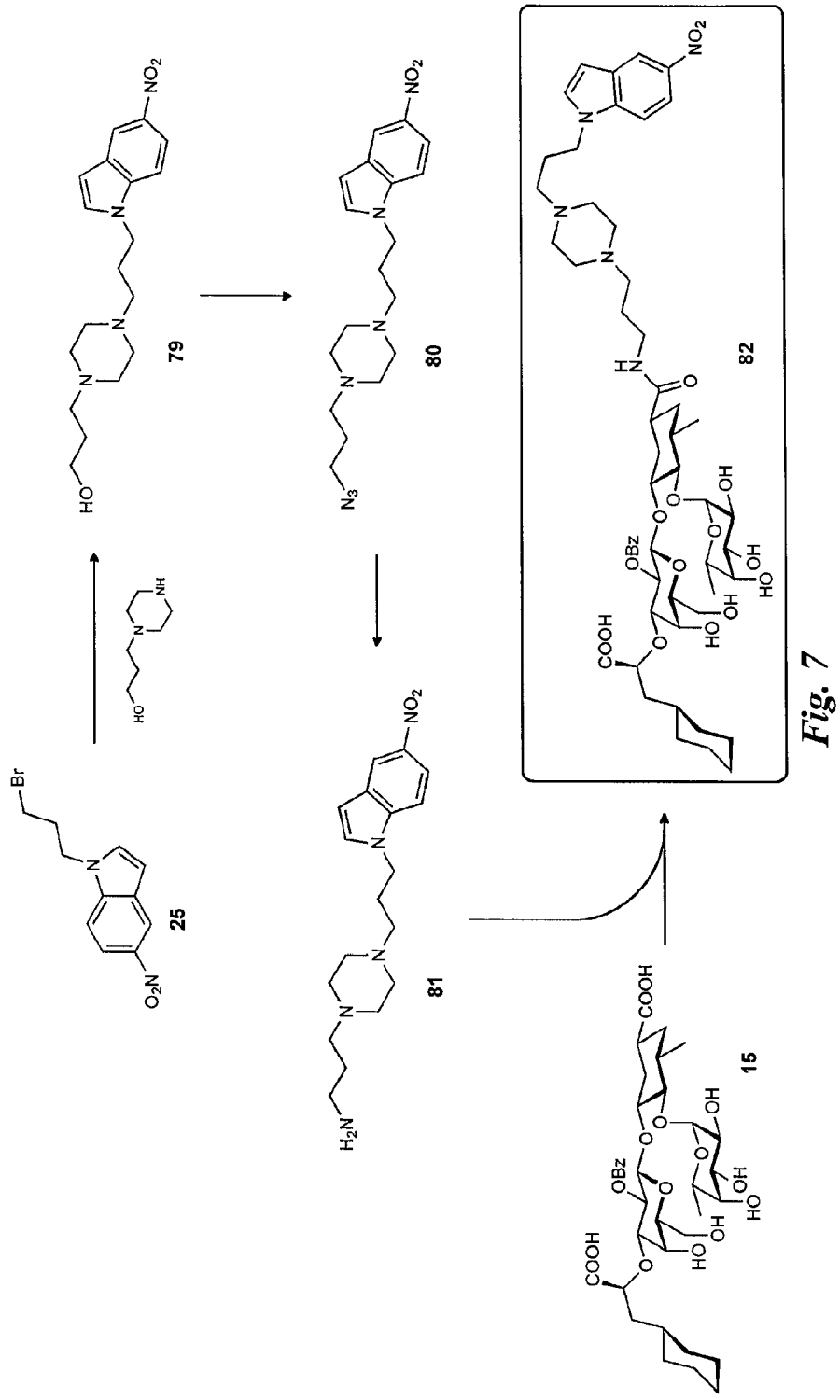
FIG. 7 is a diagram illustrating the synthesis of the selectin antagonists with piperazine linker.

Synthesis of the Selectin Antagonist with Piperazine Linker (FIG. 7)

Synthesis of Intermediate 79

3-{4-[3-(5-Nitro-1H-indol-1-yl)propyl]piperazin-1-yl}propan-1-ol

Bromide 25 (176 mg, 0.622 mmol), 3-(piperazin-1-yl)propan-1-ol (278 mg, 1.93 mmol), and Et$_3$N (259 μL, 1.87 mmol) were dissolved in anhydrous DMF and stirred at r.t. for 2 h. After removal of the solvent in vacuo, the crude product was subjected to silica gel chromatography (MeOH in CH$_2$Cl$_2$, gradient 0 to 20 to 80%) to afford alcohol 79 (215 mg, quant.) as yellow crystals.

$^1$H-NMR (500 MHz, CDCl$_3$): δ 1.70-1.76 (m, 2H, H-2''), 1.99 (p, J=6.7 Hz, 2H, H-2'), 2.04-3.07 (bs, 8H, Pip-H), 2.23 (t, J=6.7 Hz, 2H, H-3'), 2.61-2.66 (m, 2H, H-1''), 3.77-3.81 (m, 2H, H-3''), 4.25 (t, J=6.6 Hz, 2H, H-1'), 6.64-6.68 (m, 1H, H-3), 7.26-7.28 (m, 1H, H-2), 7.39-7.44 (m, 1H, H-7), 8.06-8.10 (m, 1H, H-6), 8.54-8.57 (m, 1H, H-4); $^{13}$C-NMR (125 MHz, CDCl$_3$): δ 27.06 (C-2''), 27.12 (C-2'), 44.10 (C-1'), 52.92 (2C, C-a, C-a'), 53.28 (2C, C-b, C-b'), 54.24 (C-3'), 58.61 (C-1''), 64.38 (C-3''), 103.99 (C-3), 109.44 (C-7), 117.01 (C-6), 118.18 (C-4), 127.58 (C-9), 131.23 (C-2), 138.98 (C-8), 141.39 (C-5); IR (KBr): ν=3435 (s, OH), 2947 (m), 2922 (m), 2826 (m), 1634 (vw), 1610 (w), 1578 (vw), 1513 (s), 1479 (m), 1464 (m), 1404 (w), 1369 (w), 1328 (vs, NO$_2$), 1306 (s), 1274 (m), 1186 (w), 1157 (m), 1130 (m), 1067 (s), 1006 (m) 899 (vw), 779 (w), 751 (m), 718 (w) cm$^{-1}$.

Synthesis of Intermediate 80

1-{3-[4-(3-Azidopropyl)piperazin-1-yl]propyl}-5-nitro-1H-indole

Alcohol 79 (181 mg, 0.522 mmol) and diphenyl phosphoryl azide (DPPA; 134 μL, 0.626 mmol) were dissolved in anhydrous THF (2 mL). The solution was cooled to −15° C. in a salt-ice bath, and diazobicyclo undecene (DBU; 93.6 μL, 0.626 mmol) was added dropwise, and the solution was allowed to warm to r.t. After 2 h, NaN$_3$ (71 mg, 1.09 mmol) was added to the reaction mixture as there was no reaction progress according to TLC(CH$_2$Cl$_2$, MeOH 10:1). After 12 h of stirring, additional 0.5 eq. of DPPA (56 μL, 0.261 mmol) and DBU (39 μL, 0.261 mmol) were added, and stirring was continued for 2 h. The solvent was removed under reduced pressure, the crude mixture was dissolved in EtOAc (30 mL), washed with satd. aq. NaHCO$_3$ (20 mL) and brine (20 mL). The aqueous layers were extracted with EtOAc (2×30 mL), and the organic phase was dried over Na$_2$SO$_4$. After removal of the solvent in vacuo, the mixture was purified using silica gel chromatography (MeOH in CH$_2$Cl$_2$, gradient 0 to 70%) to afford a mixture of azide 80 and its diphenyl phosphoryl ester (note: in TLC, azide and ester were not separable using CH$_2$Cl$_2$, MeOH 10:1). The mixture of azide and ester was dissolved in anhydrous DMF, and NaN$_3$ (171 mg, 2.63 mmol) was added. The mixture was stirred at 60° C. for 25 h until TLC (on deactivated TLC plates; petroleum ether, EtOAc 1:1+Et$_3$N) and MS indicated full conversion of the phosphoryl ester. H$_2$O (20 mL) was added, and the aqueous phase was extracted with EtOAc (3×50 mL). The organic layers were washed with NaHCO$_3$ (20 mL) and brine (20 mL) and subsequently dried over Na$_2$SO$_4$. After removing the solvent in vacuo, the crude product was purified using silica gel chromatography (MeOH in CH$_2$Cl$_2$, gradient 0 to 10 to 70%) to give azide 80 (154 mg, 79%) as a viscous yellow oil.

$^1$H-NMR (500 MHz, CDCl$_3$): δ 1.74-1.81 (p, J=6.7 Hz, 2H, H-2''), 2.00 (p, J=6.7 Hz, 2H, H-2'), 2.23 (t, J=6.7 Hz, 2H, H-1'), 2.28-2.70 (m, 11H, Pip-H, H-1''), 3.34 (t, J=6.7 Hz, 2H, H-3''), 4.26 (t, J=6.6 Hz, 2H, H-1'), 6.65-6.68 (m, 1H, H-3), 7.25-7.29 (m, 1H, H-2), 7.41-7.45 (m, 1H, H-7), 8.07-8.11 (m, 1H, H-6), 8.56-8.59 (m, 1H, H-4); $^{13}$C-NMR (125 MHz, CDCl$_3$): δ 26.35 (C-2''), 27.27 (C-2'), 44.21 (C-1'), 49.65 (C-3''), 53.07, 53.28 (4C, a/a', b/b'), 54.40 (C-1'), 55.34 (C-1''), 104.05 (C-3), 109.53 (C-7), 117.13 (C-6), 118.28 (C-4), 127.66 (C-9), 131.30 (C-2), 139.08 (C-8), 141.52 (C-5).

Synthesis of Intermediate 81

3-{4-[3-(5-Nitro-1H-indol-1-yl)propyl]piperazin-1-yl}propan-1-amine

Azide 80 (149 mg, 0.401 mmol) and triphenyl phosphine (129 mg, 0.492 mmol) were dissolved in THF (4 mL) and H$_2$O (1 mL). The solution was stirred at 60° C. for 3 h, and the solvent was removed under reduced pressure. The mixture was redissolved in MeOH and subjected to preparative HPLC-MS (H$_2$O/MeCN+0.2% HCOOH) to afford amine 81 (108 mg, 78%) as a viscous yellow oil.

$^1$H-NMR (500 MHz, MeOD): δ 1.89 (p, J=7.0 Hz, 2H, H-2''), 2.14-2.21 (m, 2H, H-2'), 2.65-2.72 (m, 4H, H-1'', H-3'), 2.83 (d, J=50.9 Hz, 8H, Pip H-b/b', Pip H-a-/a'), 3.01 (t, J=7.2 Hz, 2H, H-3''), 4.36 (t, J=6.8 Hz, 2H, H-1'), 6.72-6.74 (m, 1H, H-3), 7.48-7.50 (m, 1H, H-2), 7.58-7.62 (m, 1H, H-7), 8.06-8.09 (m, 1H, H-6), 8.53-8.55 (m, 1H, H-4); $^{13}$C-NMR (125 MHz, MeOD): δ 24.46 (C-2''), 27.05 (C-2'), 39.21 (C-3'), 44.84 (C-1', 52.20 (C-b/b'), 52.70 (C-a/a'), 55.28 (C-3'), 55.67 (C-1''), 105.10 (C-3), 110.80 (C-7), 117.81 (C-6), 118.79 (C-4), 129.29 (C-9), 132.83 (C-2), 140.36 (C-8), 142.76 (C-5).

Synthesis of Product 82

(1R,3R,4R,5S)-3-[2-O-Benzoyl-3-O-((1S)-1-carboxy-2-cyclohexyl-ethyl)-(β-D-galactopyranosyl)oxy]-4-[(α-L-fucopyranosyl)oxy]-5-methyl-N-(3-{1-[3-(5-nitro-1H-indol-1-yl)propyl]piperazin-1-yl}propyl)cyclohexanecarboxamide Diacid 15 (30 mg, 40.5 μmol) and HOBt (17.0 mg, 126μmol) were dissolved in anhydrous DMF under argon. At r.t., HBTU (18.4 mg, 48.5 μmol) was added. After 5 min of stirring, the solution was transferred via a syringe to a flask containing amine 81 (89 mg, 258 μmol) and DIPEA (0.3 mL). The solvent was removed in vacuo after another 2.5 h of stirring, and the crude product was purified using preparative HPLC-MS (H$_2$O/MeCN+0.2% HCOOH). Product 82 (14.6 mg, 34%) was obtained as a yellow solid.

$^1$H-NMR (500 MHz, MeOD): δ 0.41-0.72 (m, 4H, Cy), 0.80-0.94 (m, 1H, Cy), 1.10 (d, J=6.3 Hz, 3H, Me), 1.14-1.42 (m, 11H, H-6$_a$, H-2$_a$, 5Cy, Fuc H-6, Lac H-3$_a$), 1.45-1.53 (m, 1H, Lac H-3$_b$), 1.55-1.72 (m, 5H, Cy, H-6, H-2', H-5), 2.00-

2.09 (m, 2H, H-2"), 2.11-2.20 (m, 1H, H-2), 2.20-2.70 (m, 12H, H-1, H-1", H-3', Pip-H), 3.13 (t, J=6.7 Hz, 2H, H-1'), 3.17 (t, J=9.6 Hz, 1H, H-4), 3.51-3.61 (m, 2H, Gal H-3, Gal H-5), 3.67-3.83 (m, 6H, H-3, Lac H-2, Gal H-6, Fuc H-4, Fuc H-2), 3.89 (dd, J=3.1, 10.2 Hz, 1H, Fuc H-3), 3.91-3.96 (m, 1H, Gal H-4), 4.33 (t, J=6.6 Hz, 2H, H-3"), 4.69 (d, J=8.1 Hz, 1H, Gal H-1), 4.94-5.04 (m, 2H, Fuc H-1, Fuc H-5), 5.42 (t, J=8.9 Hz, 1H, Gal H-2), 6.66-6.77 (m, 1H, Ind H-3), 7.43-7.54 (m, 3H, $C_6H_5$, Ind H-2), 7.55-7.66 (m, 2H, $C_6H_5$, Ind H-7), 8.00-8.13 (m, 3H, $C_6H_5$, Ind H-6), 8.52-8.59 (m, 1H, Ind H-4); $^{13}$C-NMR (125 MHz, MeOD): δ 16.77 (Fuc C-6), 19.31 (Me), 26.55, 26.80, 26.92 (4C, Cy, C-2'), 27.39 (C-1"), 28.17 (C-2"), 33.03, 34.42, 35.38 (3C, Cy), 35.48 (C-2), 37.67 (C-6), 39.06, 39.31 (2C, C-5, C-1'), 43.45 (C-1), 43.54 (Lac C-3), 45.30 (C-3"), 53.83, 53.92 (4C, Pip-C), 56.06 (C-1"), 57.37 (C-3'), 63.15 (Gal C-6), 67.63, 67.75 (2C, Gal C-4, Fuc C-5), 70.28 (Fuc C-2), 71.34 (Fuc C-3), 73.03 (Gal C-2), 73.93 (Fuc C-4), 76.04 (Gal C-5), 79.69 (C-3), 80.65 (Lac C-2), 82.94 C-4), 83.79 (Gal C-3), 100.36 (Fuc C-1), 100.64 (Gal C-1), 104.83 (Ind C-3), 110.94 (Ind C-7), 117.64 (Ind C-6), 118.74 (Ind C-4), 129.20 (Ind C-9), 129.68 ($C_6H_5$), 130.89 ($C_6H_5$), 131.81 ($C_6H_5$), 132.97 (Ind C-2), 134.21 ($C_6H_5$), 140.47 (Ind C-8), 142.63 (Ind C-5), 166.81 (O(C=O)Ph), 176.97 (CONH), 183.25 (COOH).

Example 5

Biological Evaluation

BIAcore Assay

The biological evaluation of the E-selectin antagonists was performed by surface plasmon resonance (SPR). For this purpose, an E-selectin/IgG construct was captured onto a BIAcore chip surface bearing covalently linked goat anti-human Fc specific antibody (Biacore Life Sciences, Uppsala, Sweden).

Ranking Procedure

The ranking of the antagonists was performed in order to obtain qualitative information on the binding strength of twenty indole antagonists. For the ranking, SPR signals were recorded at a single concentration (0.05 μM) and divided by the molecular weight of the compounds. The result obtained was normalized to the response obtained with an internal standard (63) in order to avoid problems related to the measurement on different chips with different surfaces. DMSO calibration and double referencing were applied to correct bulk effects and other systematic artifacts (subtraction of reference surface and blank injection).

Evaluation of E-Selectin Antagonists with Surface Plasmon Resonance (SPR)-Based Assay Ten twofold serial dilutions of the ligand were non-randomly injected. The E-selectin antagonists were diluted in running buffer (HBS-P supplemented with 20 mm calcium and DMSO 5% v/v). Antagonist dilutions were injected with a 600 s association time and 600 s dissociation time at a flow rate of 20 μL/min over the reference and the active flow cell. Saturation was reached at a concentration of 1 μm and a total of eleven twofold dilutions were injected. In addition, to prevent the presence of residual traces of compound, a blank injection was performed between each injection of ligand dilution. DMSO calibration and double referencing were applied to correct bulk effects and other systematic artifacts (subtraction of reference surface and blank injection).

The results are summarized in Table 1.

TABLE 1

| No. | Structure | $K_D$ values |
|---|---|---|
| 56 | 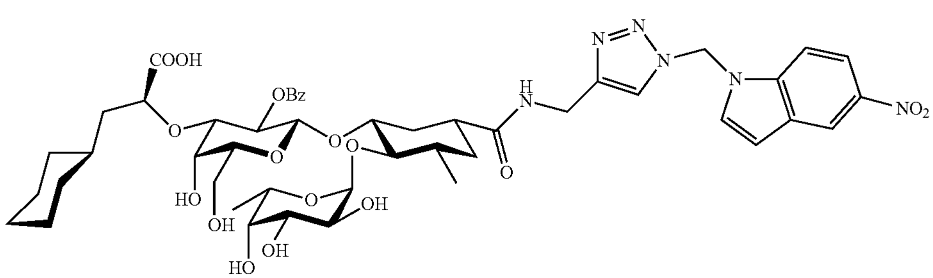 | >89 nM* |
| 57 | 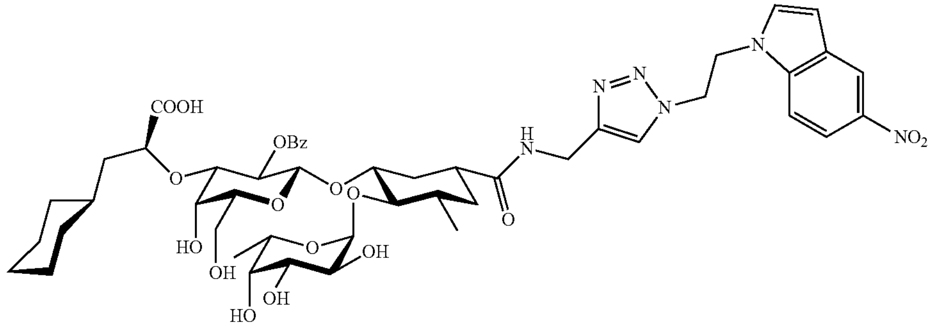 | >89 nM* |

Absolute and relative* binding affinities

TABLE 1-continued

Absolute and relative* binding affinities

| No. | Structure | $K_D$ values |
|---|---|---|
| 58 | 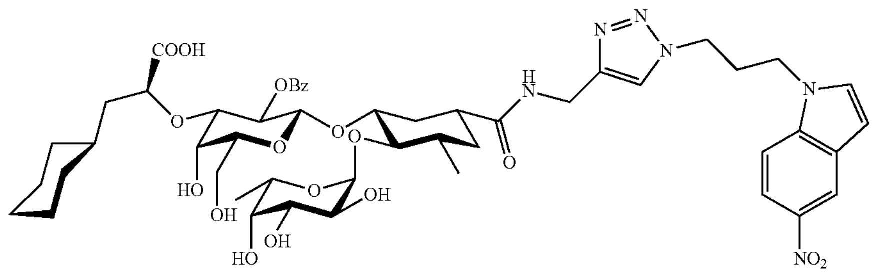 | 57 nM |
| 59 | 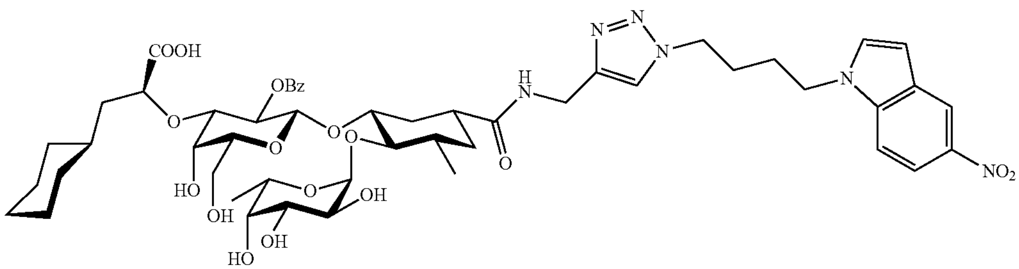 | >89 nM* |
| 60 | 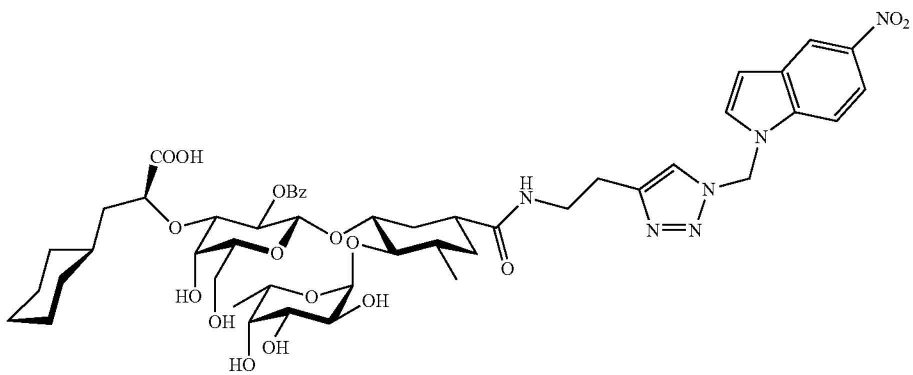 | >89 nM* |
| 61 | 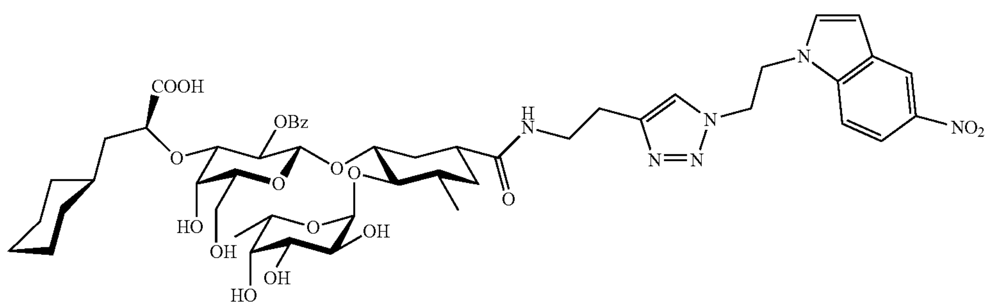 | >89 nM* |
| 62 | 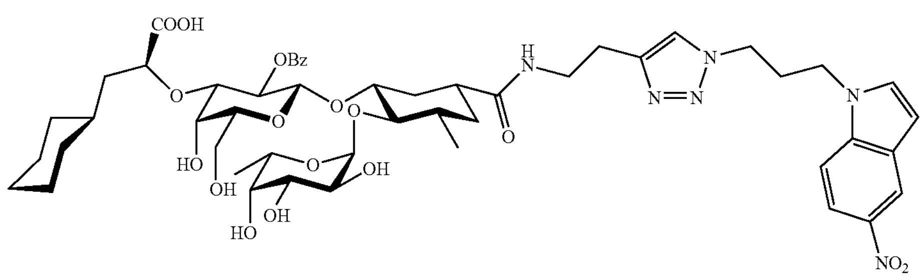 | >89 nM* |

TABLE 1-continued

Absolute and relative* binding affinities

| No. | Structure | $K_D$ values |
|---|---|---|
| 63 | 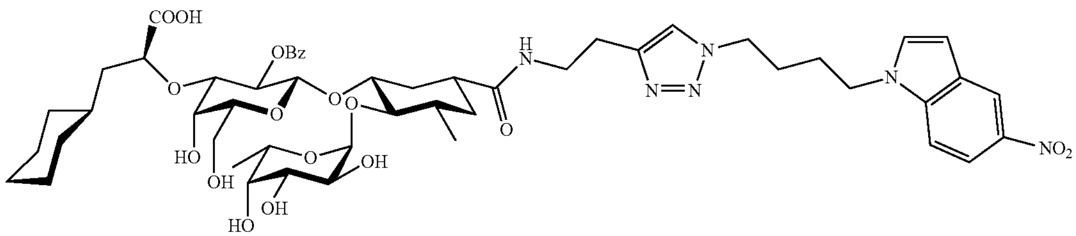 | 49 nM |
| 64 | 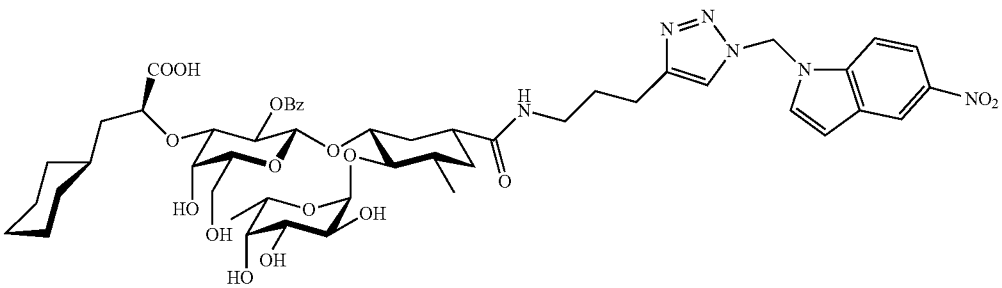 | 89 nM |
| 65 | 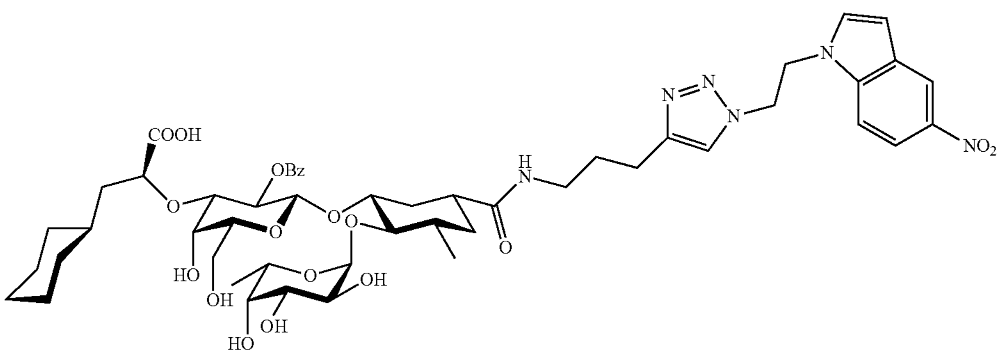 | >89 nM* |
| 66 | 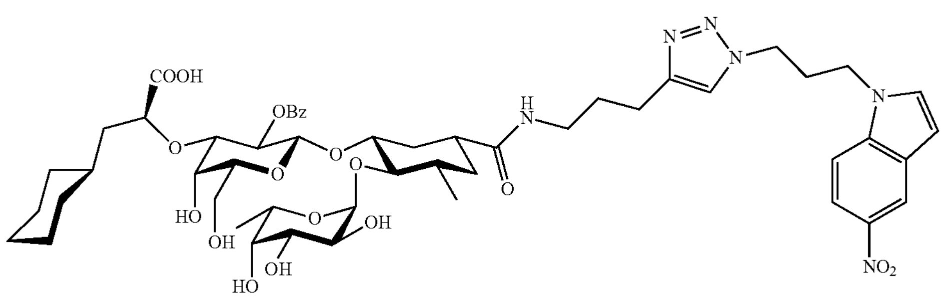 | 30 nM |
| 67 | 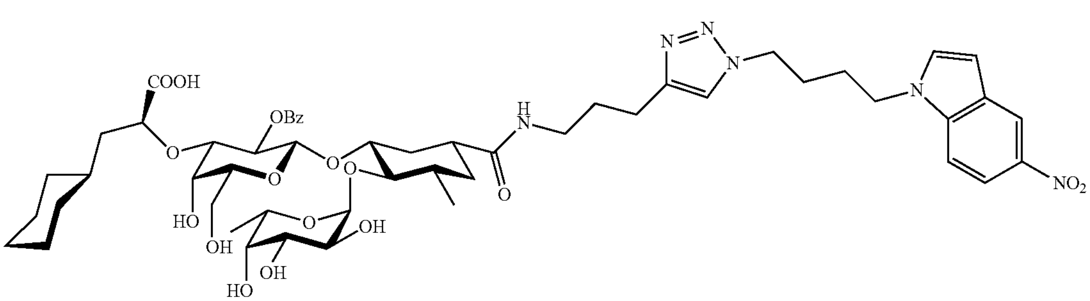 | >89 nM* |

TABLE 1-continued

Absolute and relative* binding affinities

| No. | Structure | K_D values |
|-----|-----------|------------|
| 68 | 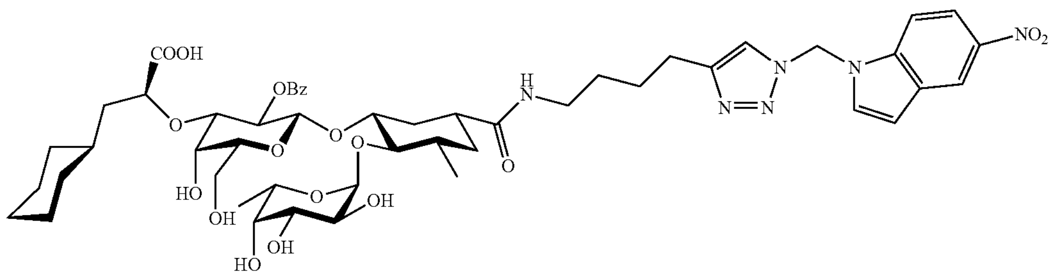 | >89 nM* |
| 69 | 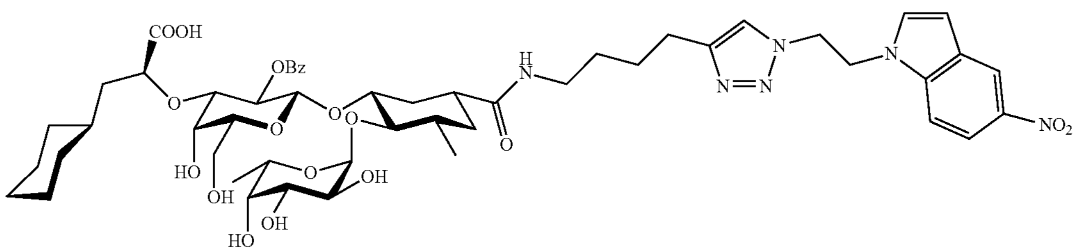 | >89 nM* |
| 70 | 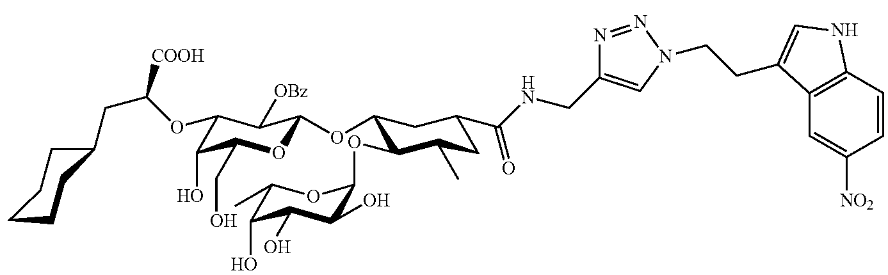 | >89 nM* |
| 71 | 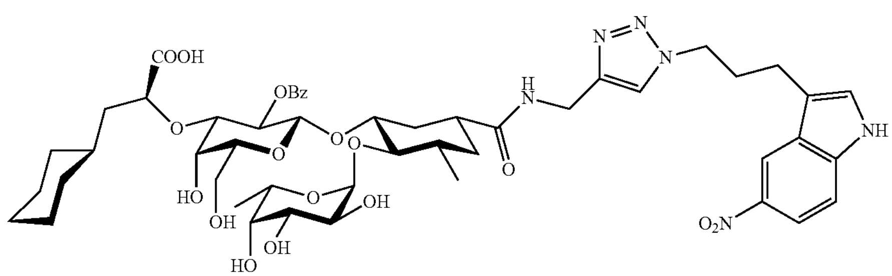 | >89 nM* |
| 72 | 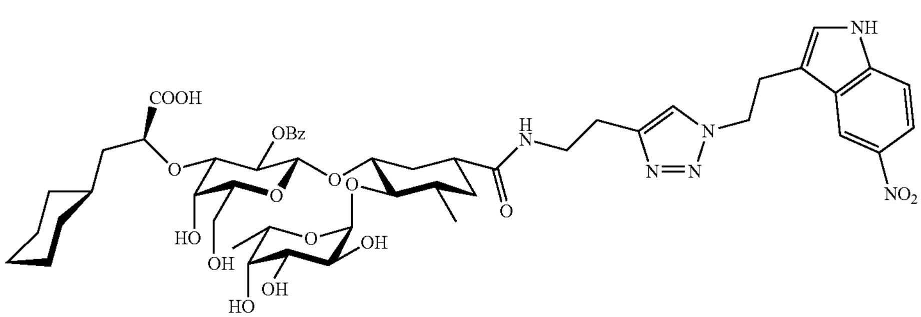 | >89 nM* |

TABLE 1-continued

Absolute and relative* binding affinities

| No. | Structure | $K_D$ values |
|---|---|---|
| 73 | 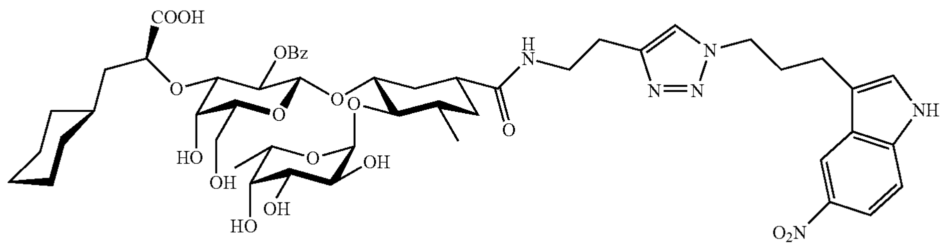 | 50 nM |
| 74 | 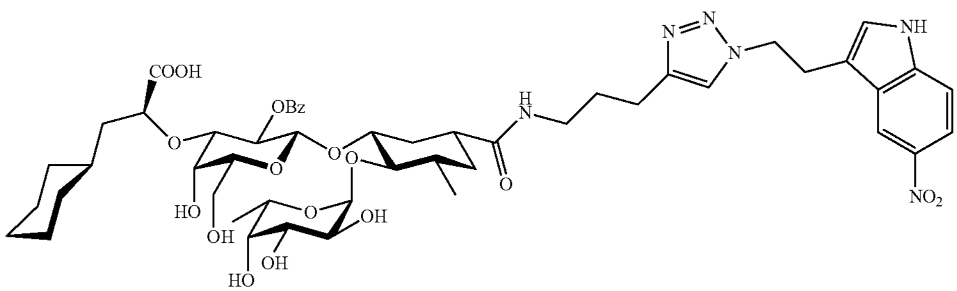 | >89 nM* |
| 75 | 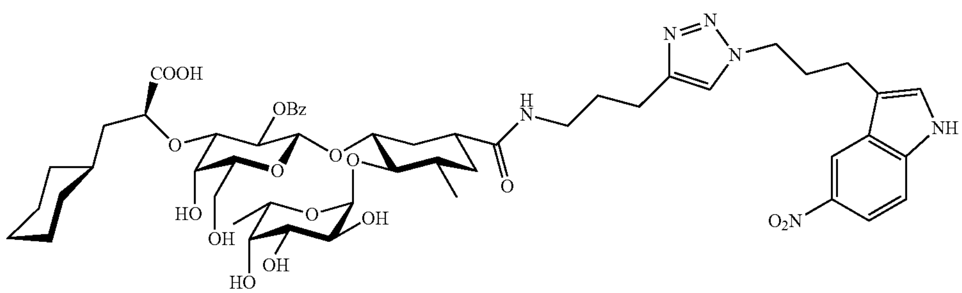 | >89 nM* |
| 76 | 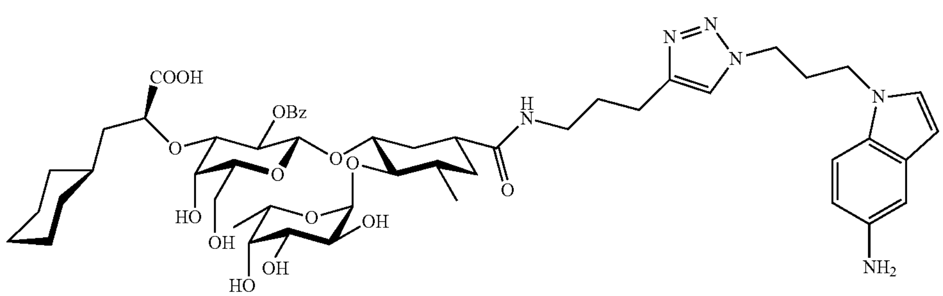 | >89 nM* |
| 77 | 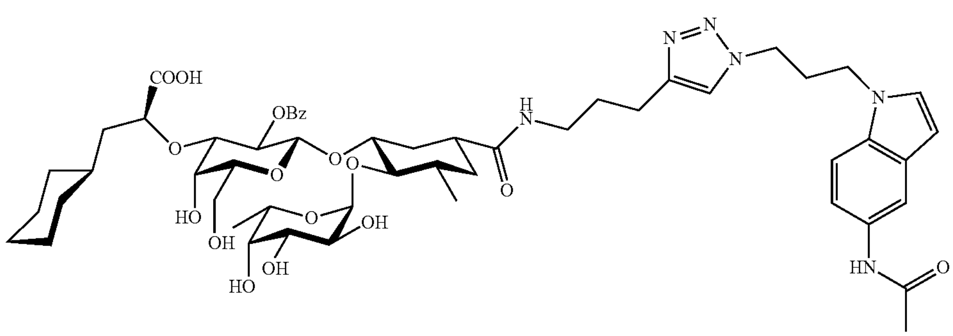 | >89 nM* |

TABLE 1-continued

Absolute and relative* binding affinities

| No. | Structure | $K_D$ values |
|---|---|---|
| 78 | 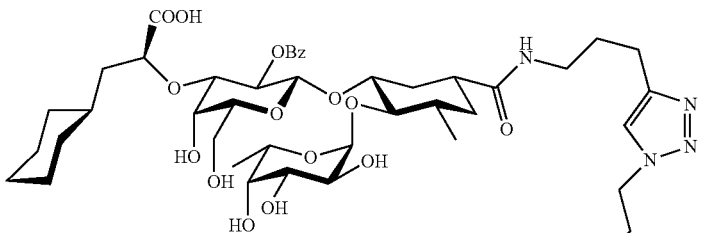 | >89 nM* |
| 82 | 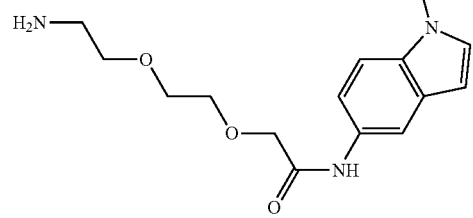 | 110 nM |

*Affinity determined in the ranking procedure described above, i.e., the $K_D$ values are larger than for reference compound 64, however below 135 nM.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A compound or physiologically acceptable salt thereof, having one of the formulae:

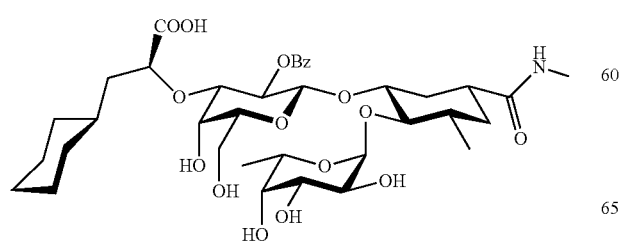

-continued

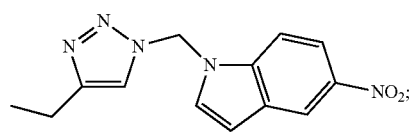

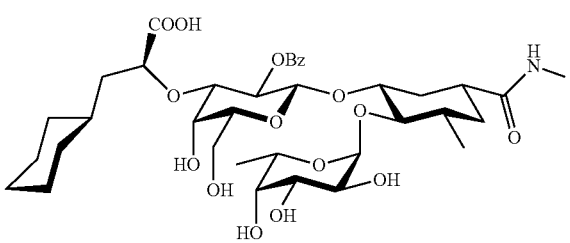

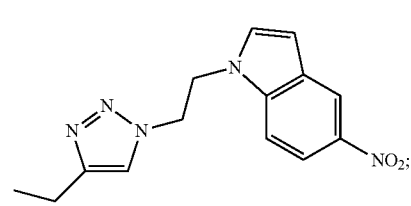

77
-continued
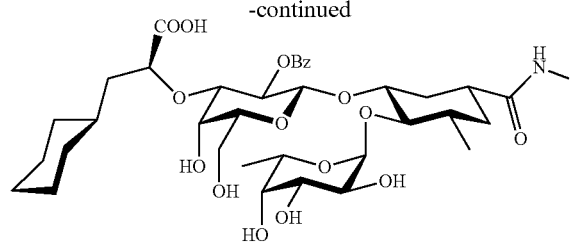
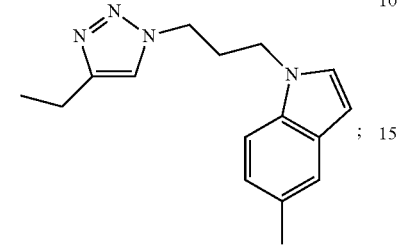
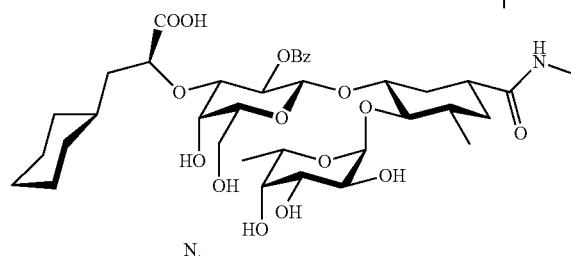
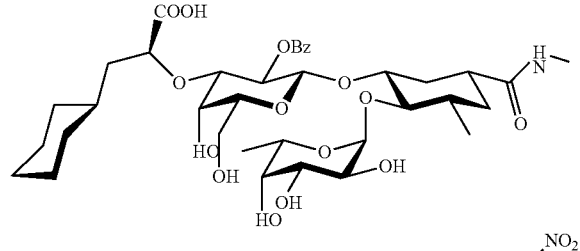
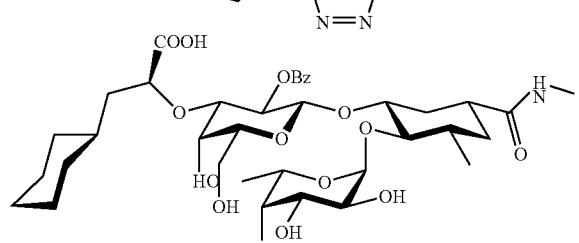
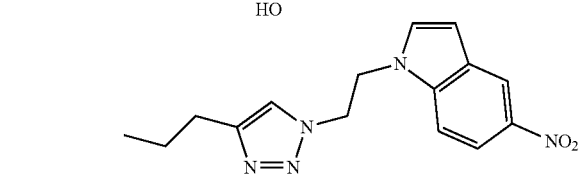
78
-continued
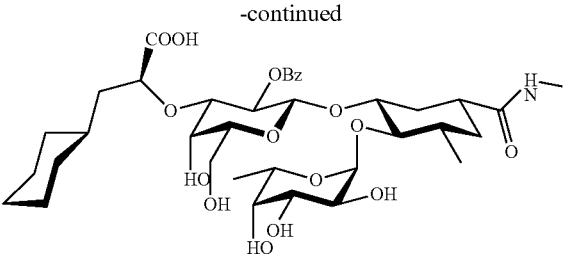
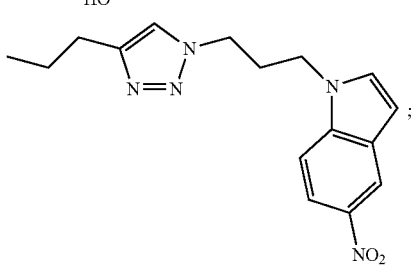
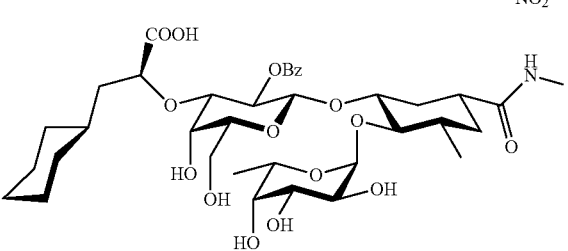
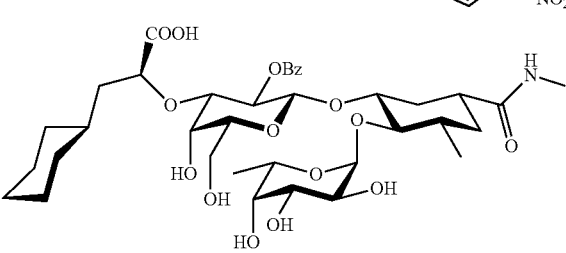
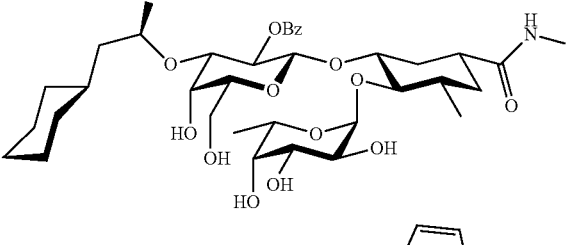
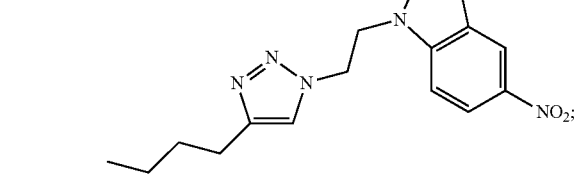

-continued
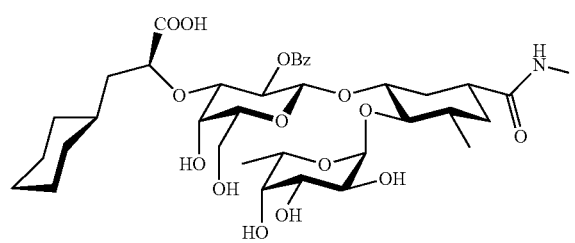
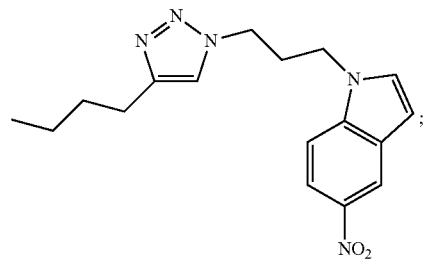
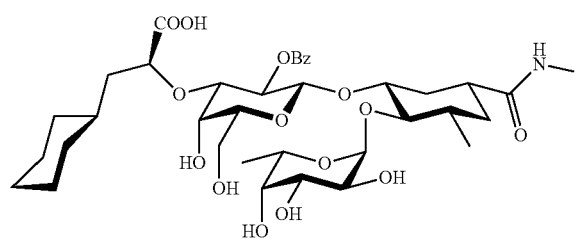
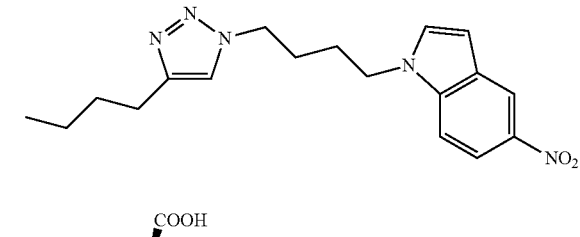
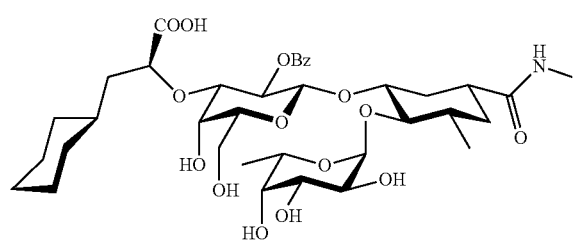
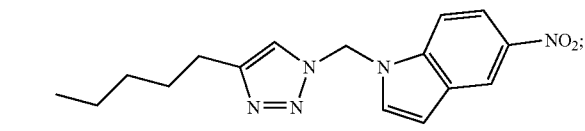
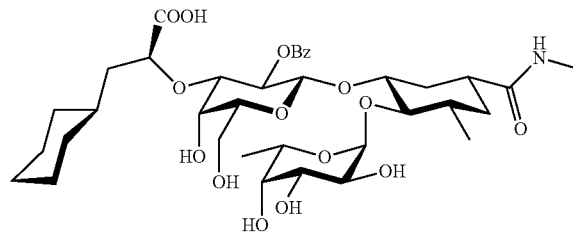
-continued
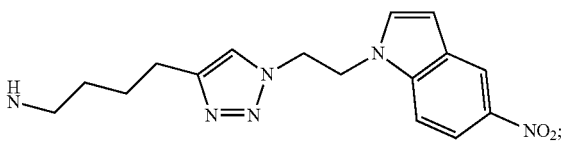
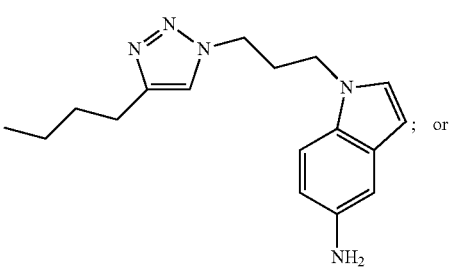
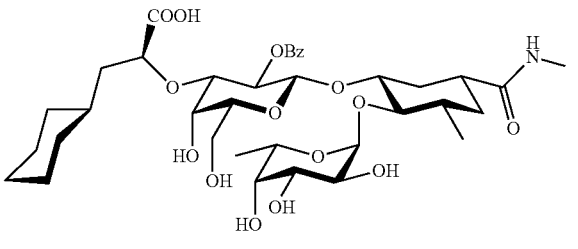
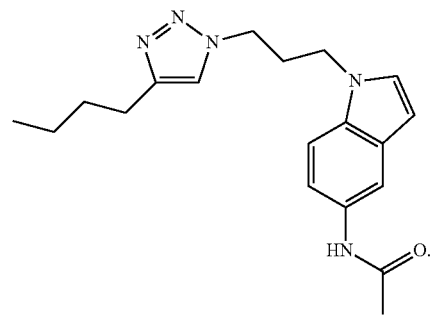
2. The compound or salt thereof according to claim 1 for inhibiting an E-selectin.
3. A composition comprising the compound or salt thereof according to claim 1 in combination with a pharmaceutically acceptable carrier or diluent.
4. A compound or physiologically acceptable salt thereof, having one of the formulae:

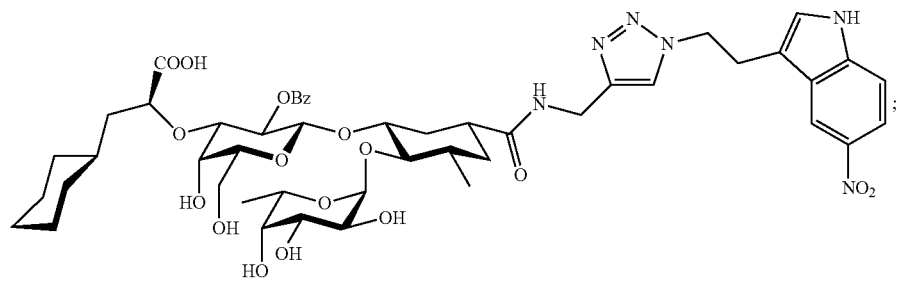
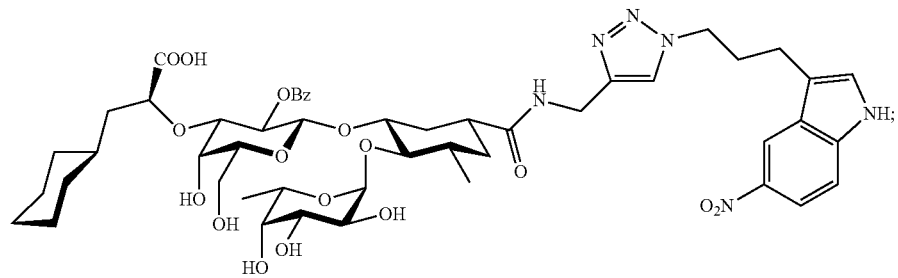
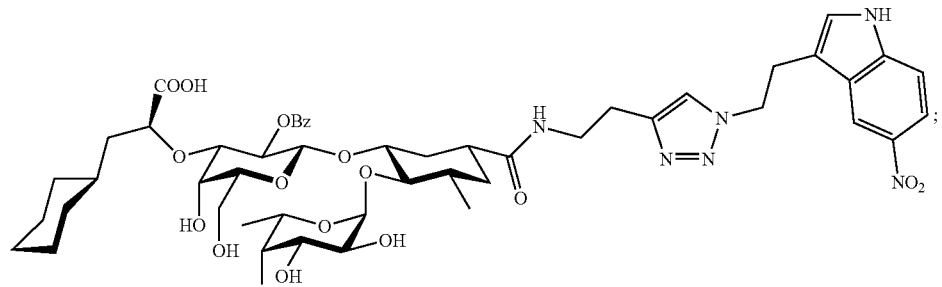
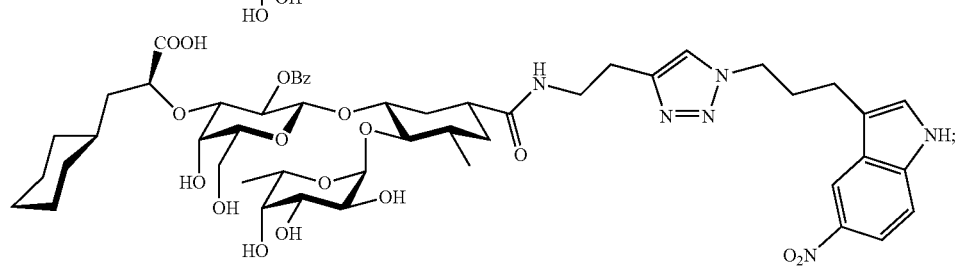
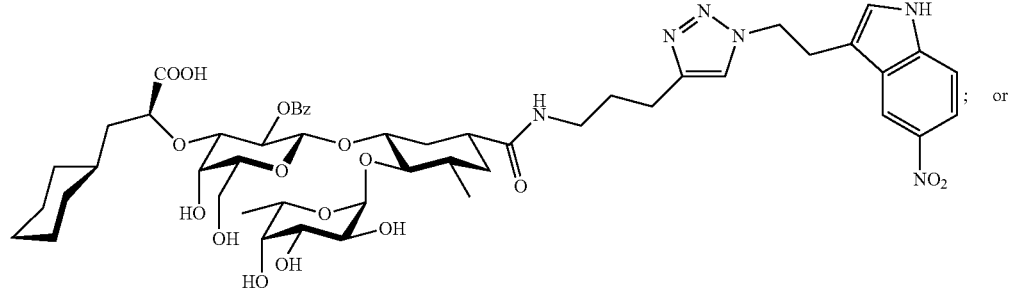 ; or
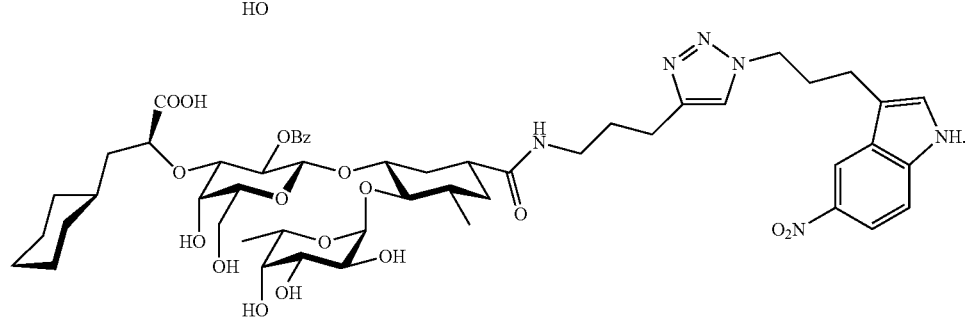

5. The compound or salt thereof according to claim 4 for inhibiting an E-selectin.

6. A composition comprising the compound or salt thereof according to claim 4 in combination with a pharmaceutically acceptable carrier or diluent.

7. A compound or physiologically acceptable salt thereof, having one of the formulae:

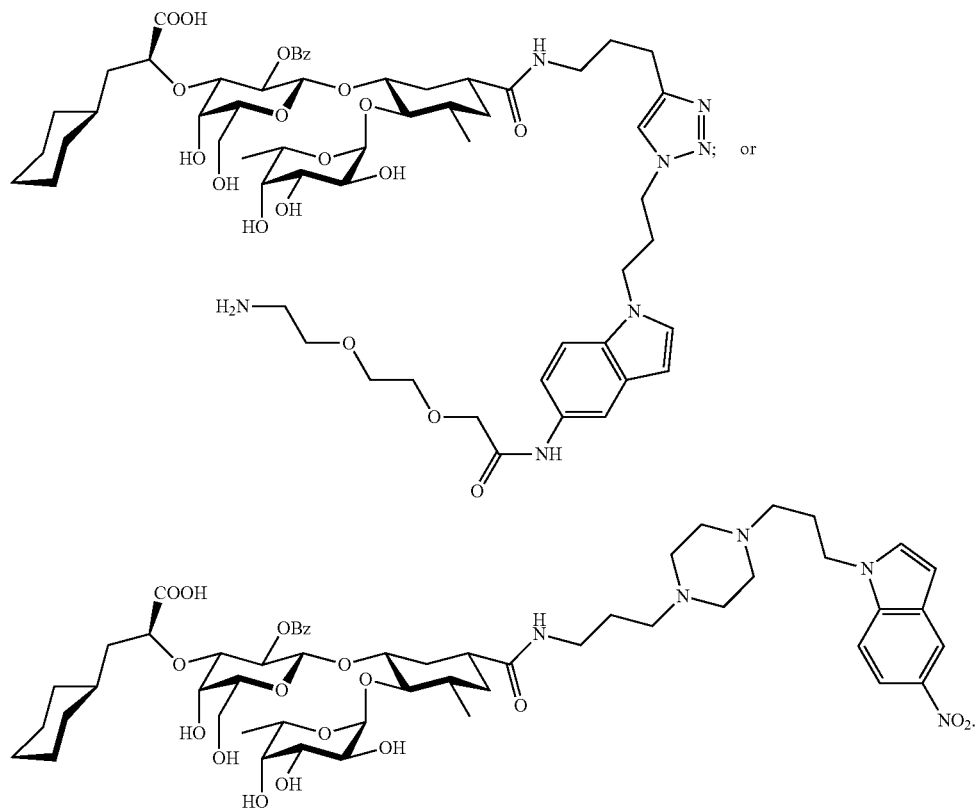

8. The compound or salt thereof according to claim 7 for inhibiting an E-selectin.

9. A composition comprising the compound or salt thereof according to claim 7 in combination with a pharmaceutically acceptable carrier or diluent.

* * * * *